(12) United States Patent
Bates et al.

(10) Patent No.: US 9,932,330 B2
(45) Date of Patent: Apr. 3, 2018

(54) PIPERAZINE DERIVATIVES FOR TREATING DISORDERS

(71) Applicants: The University of Nottingham, Nottinghamshire (GB); NewSouth Innovations PTY Limited, New South Wales (AU)

(72) Inventors: David Bates, Nottinghamshire (GB); Jonathan Morris, New South Wales (AU)

(73) Assignees: The University of Nottingham, Nottinghamshire (GB); NewSouth Innovations PTY Limited, New South Wales (AU)

( * ) Notice: Subject to any disclaimer, the term of this patent is extended or adjusted under 35 U.S.C. 154(b) by 0 days.

(21) Appl. No.: 15/708,315

(22) Filed: Sep. 19, 2017

(65) Prior Publication Data
US 2018/0044331 A1    Feb. 15, 2018

Related U.S. Application Data

(63) Continuation of application No. 15/609,596, filed on May 31, 2017, now Pat. No. 9,796,707, which is a continuation of application No. 15/304,678, filed as application No. PCT/GB2015/051172 on Apr. 17, 2015, now Pat. No. 9,695,160.

(30) Foreign Application Priority Data

Apr. 17, 2014    (GB) ................................. 1406956.1

(51) Int. Cl.
| | | |
|---|---|---|
| *A61K 31/506* | (2006.01) | |
| *A61K 31/497* | (2006.01) | |
| *A61K 31/496* | (2006.01) | |
| *C07D 413/14* | (2006.01) | |
| *C07D 405/12* | (2006.01) | |
| *C07C 271/10* | (2006.01) | |
| *C07D 307/54* | (2006.01) | |
| *C07D 413/12* | (2006.01) | |
| *C07D 405/04* | (2006.01) | |
| *C07D 401/12* | (2006.01) | |
| *C07D 233/90* | (2006.01) | |
| *C07D 333/38* | (2006.01) | |
| *C07D 405/14* | (2006.01) | |
| *C07D 307/52* | (2006.01) | |
| *C07D 271/10* | (2006.01) | |
| *C07D 269/02* | (2006.01) | |
| *C07D 241/04* | (2006.01) | |
| *C07D 309/04* | (2006.01) | |

(52) U.S. Cl.
CPC .......... *C07D 413/14* (2013.01); *A61K 31/496* (2013.01); *A61K 31/497* (2013.01); *A61K 31/506* (2013.01); *C07C 271/10* (2013.01); *C07D 233/90* (2013.01); *C07D 241/04* (2013.01); *C07D 269/02* (2013.01); *C07D 271/10* (2013.01); *C07D 307/52* (2013.01); *C07D 307/54* (2013.01); *C07D 309/04* (2013.01); *C07D 333/38* (2013.01); *C07D 401/12* (2013.01); *C07D 405/04* (2013.01); *C07D 405/12* (2013.01); *C07D 405/14* (2013.01); *C07D 413/12* (2013.01)

(58) Field of Classification Search
CPC .. C07D 413/14; C07D 233/90; C07D 333/38; C07D 401/12; C07D 405/04; C07D 405/12; C07D 405/14; C07D 413/12
USPC ....................................................... 514/252.11
See application file for complete search history.

(56) References Cited

U.S. PATENT DOCUMENTS

2015/0274668 A1* 10/2015 Harper ................. A61K 31/341
514/235.5

FOREIGN PATENT DOCUMENTS

| EP | 1712242 | 10/2006 |
|---|---|---|
| WO | 33/102105 | 11/2003 |
| WO | 2005063293 | 7/2005 |
| WO | 2008110777 | 9/2008 |
| WO | 2009106855 | 9/2009 |
| WO | 2010058227 | 5/2010 |
| WO | 2011036429 | 3/2011 |
| WO | 2011148200 | 12/2011 |
| WO | 2014060763 | 4/2014 |

OTHER PUBLICATIONS

Aubol, et al., "Processive phosphorylation of alternative splicing factor/splicing factor 2", Proceedings of the National Academy of Sciences of the United States of America, Oct. 28, 2003, vol. 100, issue 22, pp. 12601-12606.
Velazquez-Dones, et al., "Mass spectrometric and kinetic analysis of ASF/SF2 phosphorylation by SRPK1 and Clk/Sty", Journal of Biological Chemistry, Dec. 16, 2005, vol. 280, issue 50, pp. 41761-41768.
Ngo, et al., "Interplay between SRPK and Clk/Sty kinases in phosphorylation of the splicing factor ASF/SF2 is regulated by a docking motif in ASF/SF2", Molecular Cell, Oct. 7, 2005, vol. 20, issue 1, pp. 77-89.
Xu, et al., "The evolution of alternative splicing exons in vascular endothelial growth factor A", Gene, 2011, vol. 487, issue 2, pp. 143-150.
Caires, et al., "VEGFA Family Isoforms Regulate Spermatogonial Stem Cell Homeostasis in Vivo", Endocrinology, Feb. 2012, vol. 153, issue 2, pp. 887-900.
Zhao, et al. "Expression of pro- and anti-angiogenic isoforms of VEGF in the mouse model of oxygen-induced retinopathy", Experimental Eye Research, 2011, vol. 93, issue 6, pp. 921-926.

(Continued)

*Primary Examiner* — Yevgeny Valenrod
(74) *Attorney, Agent, or Firm* — Hovey Williams LLP

(57) ABSTRACT

Anti-angiogenic treatments, treatments of hyperpermeability disorders, treatments of neuropathic and neurodegenerative disorders, pain treatments, methods of reducing the risk of pre-eclampsia and compounds for use in such methods are described.

20 Claims, 27 Drawing Sheets

(56) References Cited

OTHER PUBLICATIONS

Harris, et al., "Do Anti-Angiogenic VEGF (VEGFxxxb) Isoforms Exist? A Cautionary Tale", Plos One, May 2012, vol. 7, issue 5, 14 pages.
McFee, et al., "The balance of proangiogenic and antiangiogenic VEGFA isoforms regulate follicle development", Cell and Tissue Research, Feb. 10, 2012, vol. 349, issue 3, pp. 635-647.
Ishida, et al., "VEGF(164)-mediated inflammation is required for pathological, but not physiological, ischemia-induced retinal neovascularization", Journal of Experimental Medicine, Aug. 4, 2003, vol. 198, issue 3, pp. 483-489.
Geroski, et al., "Drug delivery for posterior segment eye disease", IVOS, Apr. 2000, vol. 41, issue 5, pp. 961-964.
Keyt, et al., "Identification of vascular endothelial growth factor determinants for binding KDR and FLT-1 receptors—Generation of receptor-selective VEGF variants by site-directed mutagenesis", Journal of Biological Chemistry, Mar. 1996, vol. 271, issue 10, pp. 5638-5646.
Stalmans, et al., "Arteriolar and venular patterning in retinas of mice selectively expressing VEGF isoforms", Journal of Clinical Investigation, Feb. 2002, vol. 109, issue 3, pp. 327-336.
Koresawa, et al., "High-throughput screening with Quantitation of ATP Consumption: A Universal Non-Radioisotope, Homogeneous Assay for Protein Kinase", Assay and Drug Development Tech., 2004, vol. 2, issue 2, pp. 153-160.
Rennel, et al., "A Human Neutralizing Antibody Specific to Ang-2 Inhibits Ocular Angiogenesis", Microcirculation, 2011, vol. 18, issue 7, pp. 598-607.
International Preliminary Report on Patentability in related PCT Application Serial No. PCT/GB2015/051172, dated Oct. 18, 2016, 7 pages.
Chemical Abstracts Registry No. 923911-83-5 (Document No. XP002740604).
Chemical Abstracts Registry No. 1302431-25-9 (Document No. XP002740608).
Chemical Abstracts Registry No. 1301006-48-3 (Document No. XP002740607).
Chemical Abstracts Registry No. 514199-68-9 (Document No. XP002740603).
Chemical Abstracts Registry No. 940243-32-3 (Document No. XP002740605).
Chemical Abstracts Registry No. 1298551-87-7 (Document No. XP002740606).
Gammons, et al., "SRPK1 Inhibition Modulates VEGF Splicing to Reduce Pathological Neovascularization in a Rat Model of Retinopathy of Prematurity", Assoc. for Res. In Vision and Ophthalmology, Aug. 2013, vol. 54, issue 8, pp. 5797-5806.
Gammons, et al., "Topical Antiangiogenic SRPK1 Inhibitors Reduce Choroidal Neovascularization in Rodent Models of Exudative AMD", Assoc. for Res. in Vision and Ophthalmology, Sep. 2013, vol. 54, issue 9, pp. 6052-6062.
Bressler, et al., "Ocular risk factors for developing neovascular AMD in the fellow eyes of patients with unilateral neovascular AMD", Investigative Ophthalmology & Visual Science, 2004, vol. 45, U924-U924 (abstract).
D'Amore, et al., "differential regulation of VEGF/VPF and basic FGF by hypoxia", Faseb Journal, 1994, vol. 8, issue 4, A116-A116 (abstract).
Krogsgaard-Larsen, et al., A Textbook of Drug Design and Development, ed., Chapter 5, Design and Applications of Prodrugs pp. 113-191, 1991.
Nielsen, et al., "Glycolamide Esters as Biolabile Prodrugs of Carboxylic Acid Agents: Synthesis, Stability, Bioconversion, and Physicochemical Properties", Journal of Pharmaceutical Sciences, Apr. 1988, vol. 77, issue 4, pp. 285-298.
Kakeya, et al.,"Studies on Prodrugs of Cephalosporins. I. Synthesis and Biological Properties of Glycyloxybenzoyloxymethyl and Glycylaminobenzoyloxymethyl Esters of 7β-[2-(2-Aminothiazol-4-yl)-(Z)-2-methoxyiminoacetamido]-3-methyl-3-cephem-4-carboxylic Acid", Chem. Pharm. Bull., 1984, vol. 32, pp. 692-598.
Higuchi, "Prodrug and Drug Delivery—An Overview", vol. 14 of the a C. S. Symposium Series, and Bioreversible carriers in Drug Design, ed. American Pharmaceutical Association and Pergamon Press, 1987, 14 pages.
Ferris, et al., "Age-related macular degeneration and blindness due to neovascular maculopathy", Archives of Dphthalmology, Nov. 1984, vol. 102, issue 11, pp. 1640-1642.
Patz, et al., "Diseases of the macula: the diagnosis and management of choroidal neovascularization", Transactions 4merican Academy of 34 Ophthalmology and Otolaryngology, May-Jun. 1977, vol. 83, issue 3 pt 1 pp. 468-475 (abstract).
Fine, et al., "Drug therapy: Age-related macular degeneration", New England Journal of Medicine, Feb. 17, 2000, vol. 342, issue 7, pp. 483-492.
Campochiaro, et al., "Adenoviral vector-delivered pigment epithelium-derived factor for neovascular age-related macular degeneration: Results of a phase I clinical trial", Human Gene Therapy, Feb. 2006, vol. 17, issue 2, pp. 167-176.
Ovorak, et al., "Vascular-permeability factor vascular endothelial growth-factor, microvascular hyperpermeability, and angiogenesis", American Journal of Pathology, May 5, 1995, vol. 146, issue 5, pp. 1029-1039.
Spilsbury, et al., "Overexpression of vascular endothelial growth factor (VEGF) in the retinal pigment epithelium eads to the development of choroidal neovascularization", American Journal of Pathology, Jul. 1, 2000, vol. 157, issue 1, pp. 135-144.
Anderson, et al., "Perspective—A role for local inflammation in the formation of drusen in the aging eye", American Journal of Ophthalmology, Sep. 2002, vol. 134, issue 3, pp. 411-431.
Das, et al., "Angiopoietin/Tek interactions regulate MMP-9 expression and retinal neovascularization", Laboratory Investigation, Nov. 2003, vol. 83, issue 11, pp. 1637-1645.
Leung, et al., "Vascular endothelial growth-factor is a secreted angiogenic mitogen", Science, Dec. 8, 1989, vol. 246, issue 4935, pp. 1306-1309.
Jingjing, et al.,"Human Muller cells express VEGF183, a novel spliced variant of vascular endothelial growth factor", IOVS, Mar. 1999, vol. 40, issue 3, pp. 752-759.
Houck, et al., "The vascular endothelial growth-factor family—identification of a 4th molecular-species and characterization of alternative splicing of RNA", Molecular Endocrinology, 1991, vol. 5, issue 12, pp. 1806-1814.
Mineur, et al., "Newly identified biologically active and proteolysis-resistant VEGF-A isoform VEGF111 is induced by genotoxic agents", Journal of Cell Biology, Dec. 17, 2007, vol. 179, issue 6, pp. 1261-1273.
Tischer, et al., "Vascular endothelial growth-factor—a new member of the platelet-derived growth-factor gene family", Biochemical and Biophysical Research Communications, Dec. 29, 1989, vol. 165, issue 3, pp. 1198-1206.
Neufeld, et al., "Vascular endothelial growth factor (VEGF) and its receptors", The Faseb Journal, Jan. 1999, vol. 13, issue 1, pp. 9-22.
Bates, et al., "VEGF(165)b, an inhibitory splice variant of vascular endothelial growth factor, is down-regulated in renal cell carcinoma", Cancer Research, Jul. 15, 2002, vol. 62, issue 14, pp. 4123-4131.
Woolard, et al., "VEGF(165)b, an inhibitory vascular endothelial growth factor splice variant: Mechanism of action, in vivo effect on angiogenesis and endogenous protein expression", Cancer Research, Nov. 1, 2004, vol. 64, issue 21, pp. 7822-7835.
Perrin, et al., "Diabetic retinopathy is associated with a switch in splicing from anti- to pro-angiogenic isoforms of vascular endothelial growth factor", Diabetologia, Sep. 29, 2005, vol. 48, issue 11, pp. 2422-2427.
Varey, et al., "VEGF(165)b, an antiangiogenic VEGF-A isoform, binds and inhibits bevacizumab treatment in experimental colorectal carcinoma: balance of pro- and antiangiogenic VEGF-A isoforms has implications for therapy", British Journal of Cancer, Mar. 18, 2008, vol. 98, issue 8, pp. 1366-1379.
Pritchard-Jones, et al., "Expression of VEGF(xxx)b, the inhibitory isoforms of VEGF, in malignant melanoma", British Journal of Cancer, Jun. 26, 2007, vol. 97, issue 2, pp. 223-230.

(56) References Cited

OTHER PUBLICATIONS

Hua, et al., "Recombinant Human VEGF(165)b Inhibits Experimental Choroidal Neovascularization", Investigative Dphthalmology & Visual Science, Aug. 2010, vol. 51, issue 8, pp. 4282-4288.

Magnussen, et al., "VEGF-A(165)b Is Cytoprotective and Antiangiogenic in the Retina", Investigative Ophthalmology & Visual Science, Aug. 2010, vol. 51, issue 8, pp. 4273-4281.

Gragoudas, et al., "VEGF inhibition study in ocular neovascularization-1 (VISION-1):Efficacy results from phase II/III Macugen (TM) (Pegaptanib sodium) clinical trials", LOVS, May 2004, vol. 45, issue suppl. 1, U924, 2 pages (abstract attached).

Rosenfeld, et al., "Ranibizumab: Phase III clinical trial results", Ophthalmology Clinics of North America, 2006, vol. 19, issue 3, pp. 361-372.

Brown, et al., "Ranibizumab versus verteporfin for neovascular agerelated macular degeneration", New England Journal of Medicine, Oct. 5, 2006, issue 355, vol. 14, pp. 1432-1444 (29 total pages).

Brown, et al., "Ranibizumab versus Verteportin Photodynamic Therapy for Neovascular Age-Related Macular Degeneration: Two-Year Results of the ANCHOR Study", Ophthalmology, Jan. 2009, vol. 116, issue 1, pp. 57-65.e5.

Schmidt-Erfurth, et al., "Efficacy and Safety of Monthly versus Quarterly Ranibizumab Treatment in Neovascular Age-related Macular Degeneration: The EXCITE Study", Ophthalmology, May 2011, vol. 118, issue 5, pp. 831-839.

Good, et al., "The role of endothelin in the pathophysiology of glaucoma", Expert Opinion on Therapeutic Targets, 2010, vol. 14, issue 6, pp. 647-654.

Jager, - et al "Risks of intravitreous injection: A comprehensive review", The Journal of Retinal and Vitreous Diseases, 2004, vol. 24, issue 5, pp. 676-698.

Nowak, et al., "Regulation of Vascular Endothelial Growth Factor (VEGF) Splicing from Pro-angiogenic to Anti-angiogenic Isoforms—a novel therapeutic strategy for angiogenesis", Journal of Biological Chemistry, Fe. 19, 2010, vol. 285, issue 8, pp. 5532-5540.

Amin, et al., "WT1 Mutants Reveal SRPK1 to Be a Downstream Angiogenesis Target by Altering VEGF Splicing", cancer Cell, Dec. 13, 2011, vol. 20, issue 6, pp. 768-780.

Sanford, et al., "Reversible phosphorylation differentially affects nuclear and cytoplasmic functons of splicing factor 2/alternative splicing factor", Proceedings of the National Academy of Sciences of the United States of America, Oct. 18, 2005, vol. 102, issue 42, pp. 15042-15047.

Nowak, et al., "Expression of pro- and anti-angiogenic isoforms of VEGF is differentially regulated by splicing and growth factors", Journal of Cell Science, Jul. 7, 2008, vol. 121, issue 20, pp. 3487-3495.

Doukas, et al.,"Topical administration of a multi-targeted kinase inhibitor suppresses choroidal neovascularization and retinal edema", Journal of Cellular Physiology, Jan. 25, 2008, vol. 216, issue 1, pp. 29-37.

Fukuhara, et al., "Utilization of host SR protein kinases and RNA-splicing machinery during viral replication", Proceedings of the National Academy of Sciences of the United States of America, Jul. 25, 2006, vol. 103, issue 30, pp. 11329-11333.

* cited by examiner

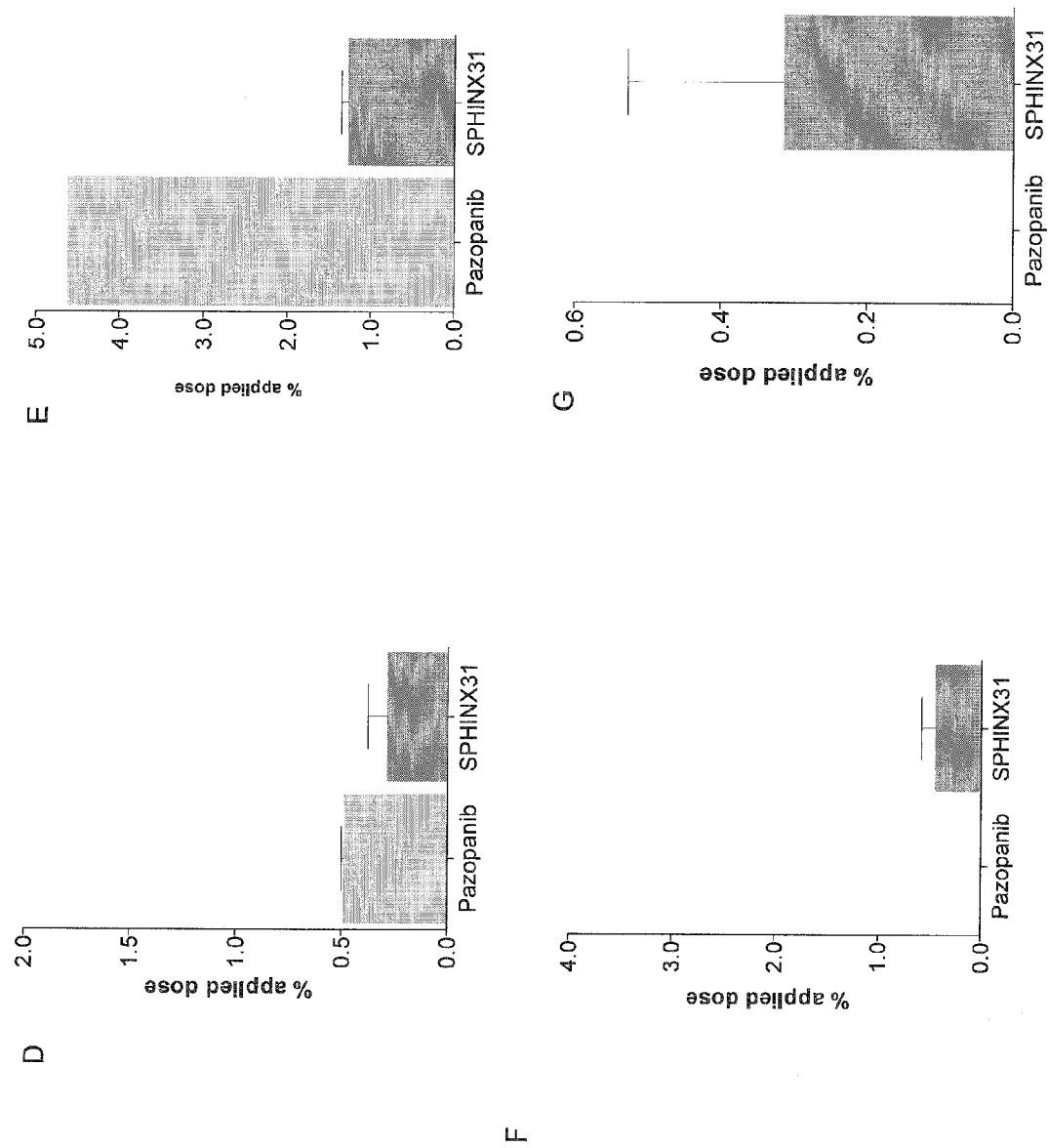
Figure 14D-G

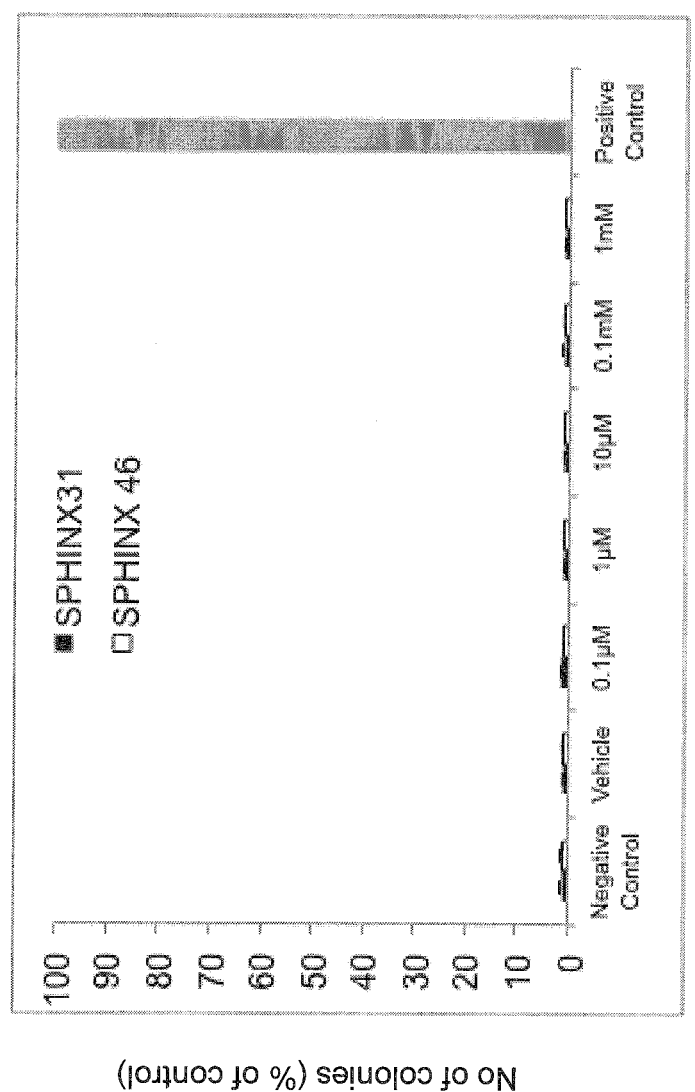
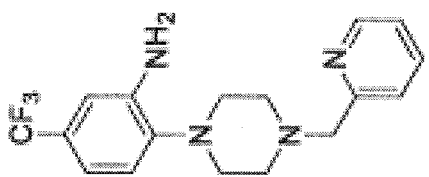
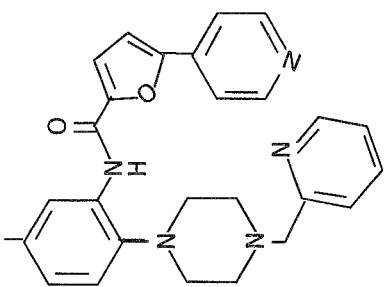
Figure 19

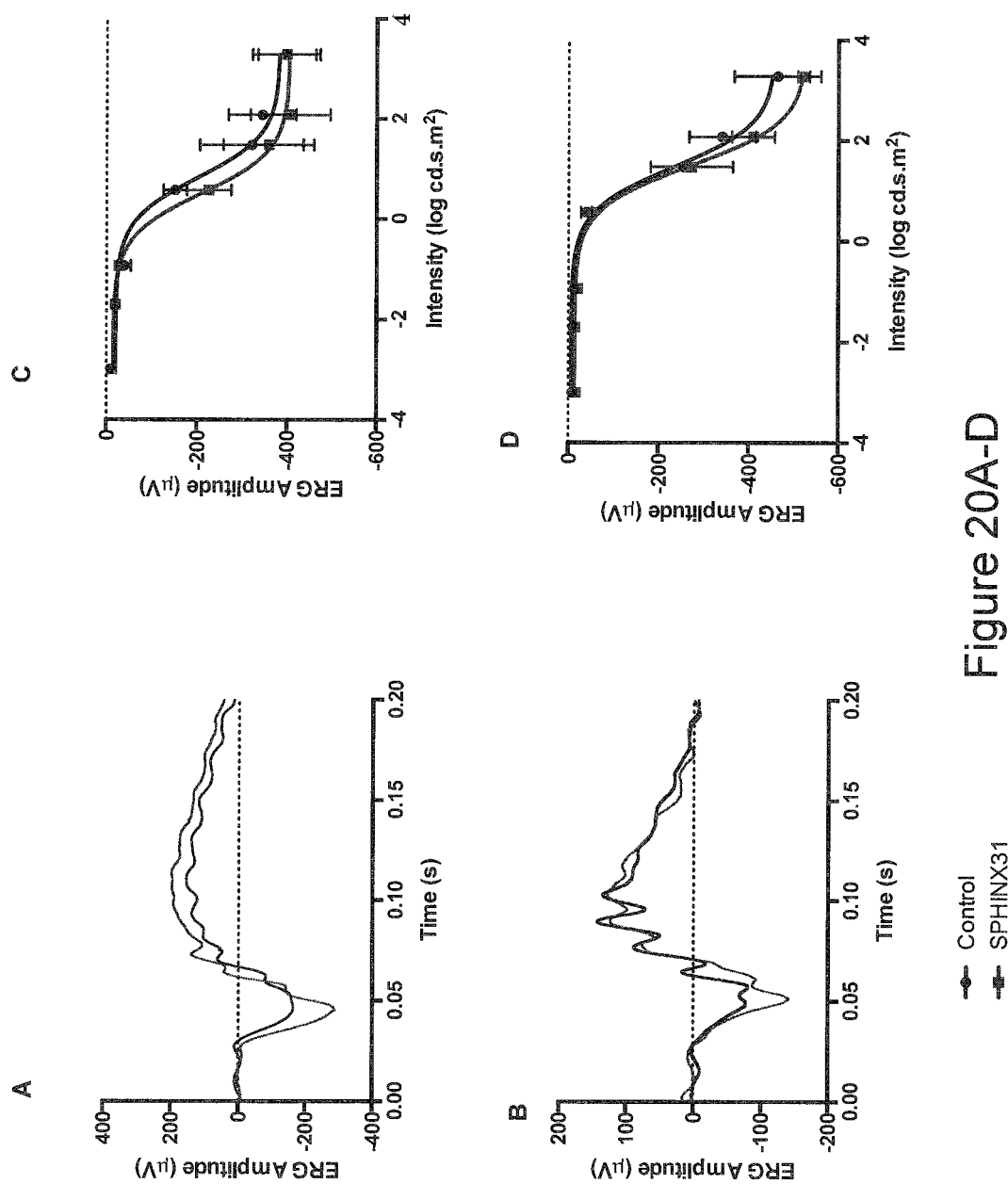
Figure 20A-D

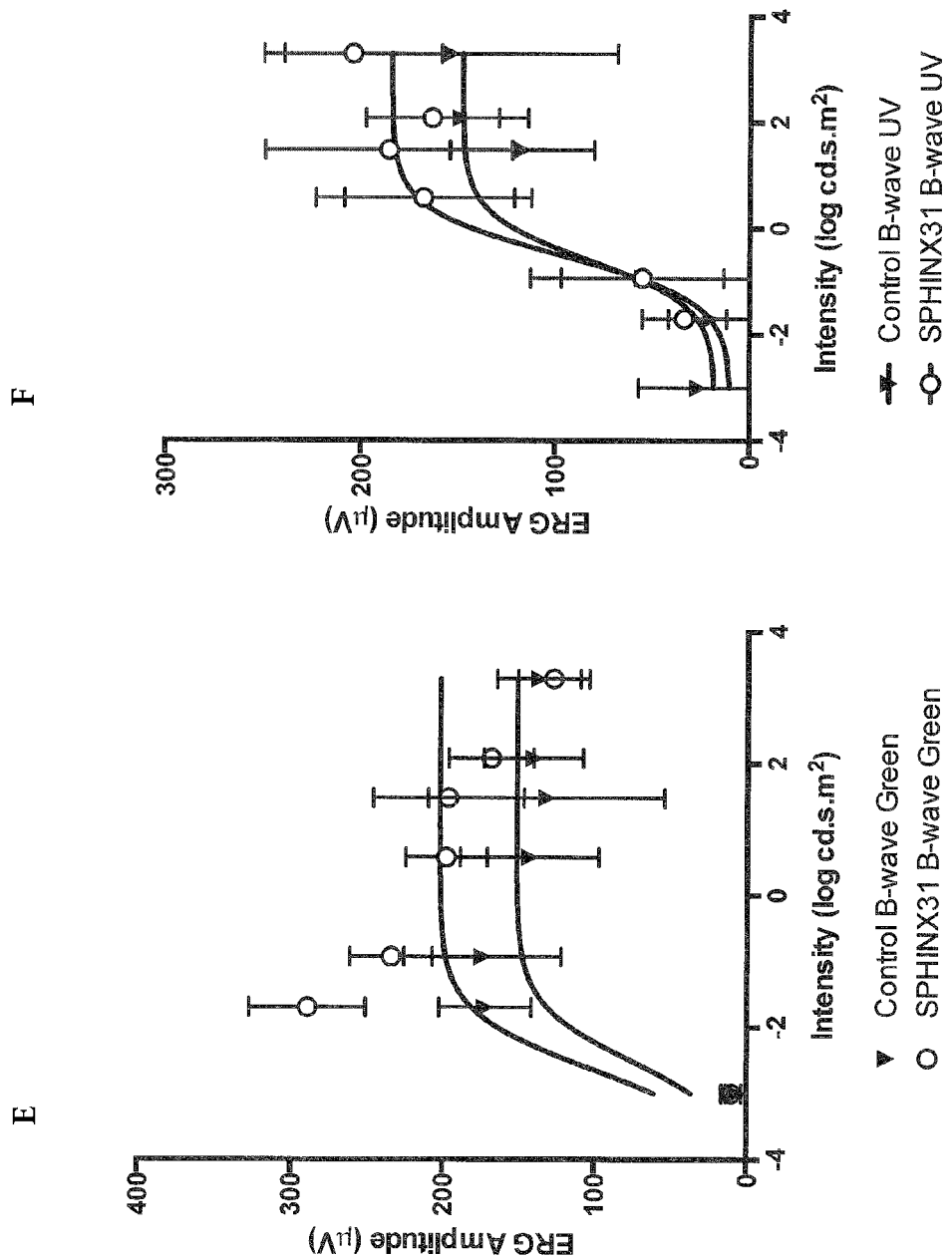
Figure 20E-F

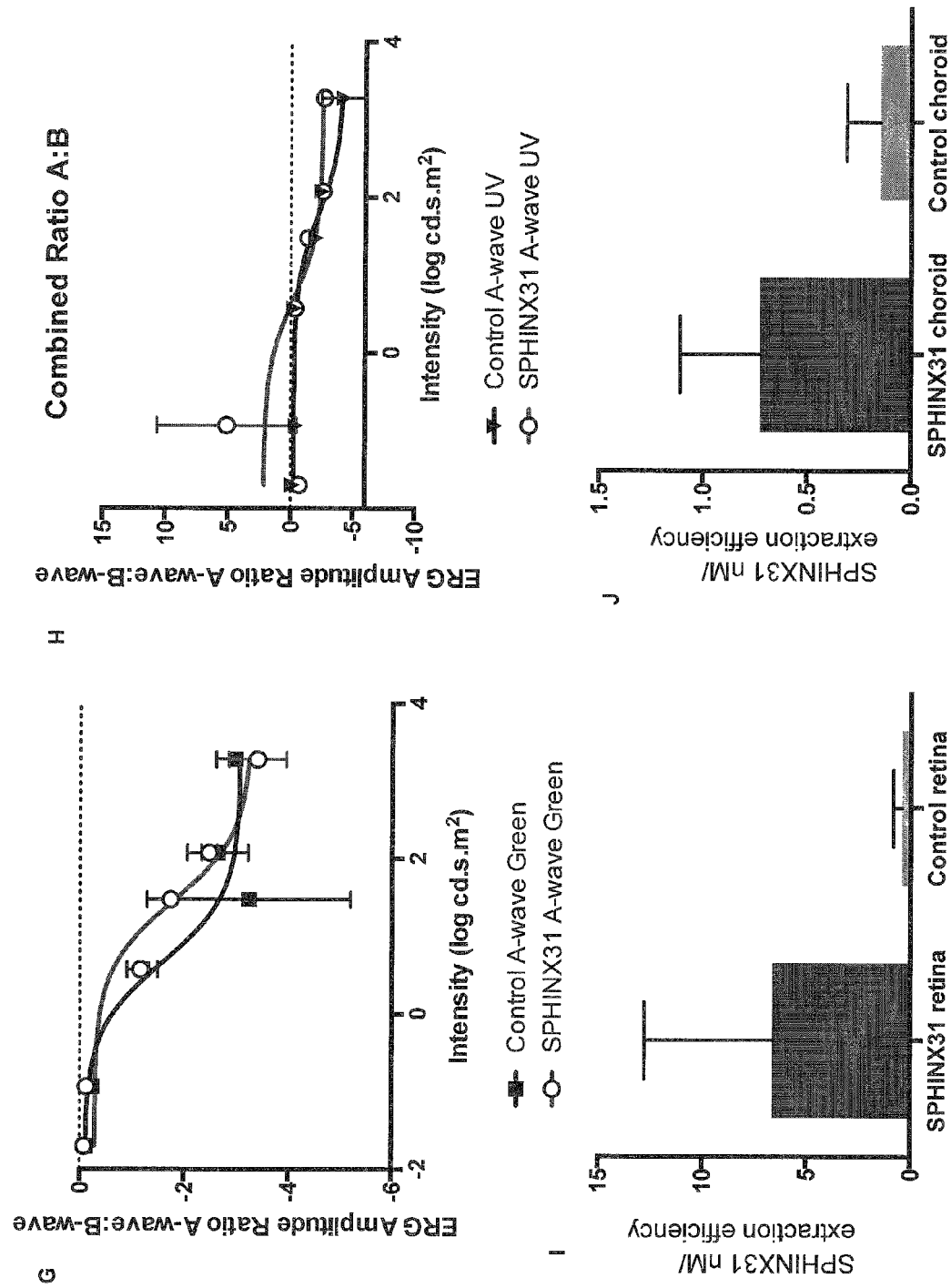
Figure 20G-J

PIPERAZINE DERIVATIVES FOR TREATING DISORDERS

RELATED APPLICATIONS

This application is a continuation of U.S. patent application Ser. No. 15/609,596, filed May 31, 2017, which is a continuation of U.S. patent application Ser. No. 15/304,678, filed Oct. 17, 2016, which is the National Stage of International Patent Application No. PCT/GB2015/051172, filed Apr. 17 2015, each of which is hereby incorporated by reference in its entirety, and claims priority to UK Patent Application No. 1406956.1 filed Apr. 17 2014.

SEQUENCE LISTING

The sequences listed in the accompanying Sequence Listing are presented in accordance with 37 C.F.R. 1.822. The Sequence Listing is submitted as an ASCII computer readable text file, which is incorporated by reference herein.

FIELD OF THE INVENTION

The present invention relates to anti-angiogenic treatments and compounds for use in anti-angiogenic treatments, particularly of conditions characterised by neovascularisation such as, for example, age-related macular degeneration.

The present invention also relates to treatments of hyperpermeability disorders and compounds for use in treating hyperpermeability disorders.

The present invention also relates to treatments of neuropathic and neurodegenerative disorders and compounds for use in treating neuropathic and neurodegenerative disorders, such as, for example, Alzheimer's disease.

The present invention also relates to pain treatments, and compounds for use in treating pain.

The present invention also relates to methods of reducing the risk of pre-eclampsia, and compounds for use in such methods.

BACKGROUND TO THE INVENTION

Age-related macular degeneration (AMD), a disease causing vision loss that affects the central area of the macula, is the leading cause of blindness in people over 50 years of age (Bressler, 2004). Exudative AMD is the most severe form of AMD (Ferris et al., 1984) primarily arising from the choroidal circulation beneath the macula and characterized by choroidal neovascularization (CNV). CNV, the abnormal growth of new vessels from the choroid into the retinal pigmented epithelium (RPE) (Patz et al., 1977), is thought to lead to visual loss due to the leakage of blood and serous fluid beneath the RPE that eventually leads to loss of photoreceptors, retinal detachment and dense macular scarring (Fine et al., 2000; Campochiaro et al., 2006). Vascular endothelial growth factor (VEGF), a key factor in angiogenesis and vascular leakage (Dvorak et al., 1995) is up-regulated during the progression of CNV (D'Amore, 1994; Spilsbury et al., 2000; Anderson et al., 2002; Das et al., 2003) and has become the lead therapeutic target for the treatment of exudative-AMD.

VEGF is a complex gene that is alternatively spliced to form a family of multiple isoforms (Leung et al., 1989; Jingjing et al., 1999), each isoform differing in biological property, activity and function (Houck et al., 1991). Most cells commonly express isoforms $VEGF_{121}$, $VEGF_{165}$, and $VEGF_{189}$, whereas $VEGF_{145}$ and $VEGF_{206}$ are comparatively rare. The majority of VEGF isoforms contain exons 1-5 (the exception being $VEGF_{111}$ (Mineur et al., 2007)) but differing portions of exons 6 and 7 that encode heparin sulphate (HS) binding domains. Alterations in the usage of these exons changes the biological properties of alternatively spliced isoforms such as their ability to bind to cell-surface heparin-sulfate proteoglycans and release angiogenic factors (Tischer et al., 1991; Neufeld et al., 1999).

In 2002 differential splicing of the eighth exon was demonstrated from a proximal splice site (PSS) to a distal splice site (DSS) 66 bases downstream (Bates et al., 2002; Woolard at al., 2004). Alternative splicing in this region generated a second family of isoforms ($VEGF_{xxx}b$), noted for their anti-angiogenic properties (Perrin et al., 2005). WO 03/102105, the contents of which are incorporated herein by reference in its entirety describes the alternatively spliced isoforms, and their therapeutic significance.

During pathological angiogenesis pro-angiogenic isoforms are selectively upregulated (Bates et al., 2002; Varey et al., 2008; Pritchard-Jones et al., 2007), suggesting $VEGF_{xxx}$ and $VEGF_{xxx}b$ may have separate regulatory pathways. These anti-angiogenic isoforms, such as $VEGF_{165}b$ and $VEGF_{121}b$ have been shown to be potently anti-angiogenic in animal models of retinal and choroidal neovascularisation, following intra-ocular injection (Hua et al 2008), and result in both endothelial and retinal epithelial cell cytoprotection (Magnussen et al 2010).

The first therapy to be FDA approved for the treatment of neovascular AMD in December 2004 was a $VEGF_{165}$, $VEGF_{189}$ and $VEGF_{206}$ specific aptamer, Pegaptanib Sodium (Macugen). During clinical trials pegaptinib dose-dependently reduced the risk of severe visual acuity loss and slowed the progression of neovascular AMD (Gragoudas et al., 2004), but did not result in significant improvement in vision. In 2006 Ranibizumab (Lucentis), a novel humanized anti-VEGF antibody fragment, was FDA approved for the treatment of neovascular AMD. Its approval was based on the results of three clinical trials where, approximately 95% of patients treated monthly with Lucentis (0.5 mg) maintained visual acuity (defined as the loss of <15 letters) and ≤40% improved vision (defined as the gain of ≥15 letters) a one year compared with 11% in the sham control treated group (Rosenfeld et al., 2006; Brown et al., 2006; Brown et al., 2009). Current treatment regimes require Lucentis administration by intra-ocular injection as often as monthly (Brown et al., 2009; Schmidt-Erfuth et al., 2011). Such intraocular injections result in increased intraocular pressure (Good et al., 2010) and a risk, albeit minor, of endopthalmitis and other severe adverse effects (Jager et al., 2004). Furthermore, bevicizumab (Avastin), an anti-VEGF antibody from which Lucentis was derived, was shown to bind $VEGF_{165}b$ with equal potency to $VEGF_{165}$, thus targeting both pro and anti-angiogenic VEGF isoforms (Varey et al 2008).

As both the anti-angiogenic and angiogenic isoforms of VEGF are derived from the same gene, the control of isoform family is a result of the control of alternative splicing. We have recently identified some of the pathways that control the splicing of VEGF at the proximal splice site, implicating the RNA binding protein SRSF1 (Nowak et al., 2008; Amin et al., 2011) and its kinase SRPK1 (Sanford et al., 2005) as key requirements for the decision by cells to use the proximal splice site, and hence generate pro-angiogenic isoforms of VEGF (Nowak et al., 2008;Nowak et al., 2010). Knockdown of SRPK1 potently reduced VEGF mediated angiogenesis in vivo in tumours and inhibition of SRPK1 and 2 reduced angiogenesis in vivo (Amin et al., 2011).

WO 2008/11077, WO 2009/106855, WO 2010/058227, WO 2011/036429 and WO 2011/148200, the disclosures of which are incorporated herein by reference, describe therapeutic and other physiological uses of agents which direct expression in favour of the VEGF$_{xxx}$b isoforms. SRPK inhibitors can in principle constitute such agents.

WO 2005/063293 describes a class of SRPK inhibitors including SRPIN340 and derivatives and analogues thereof.

WO 2014/060763 (PCT/GB2013/052716), the contents of which are incorporated herein by reference, describes SRPK inhibitors targeting SRPK1 specifically for use as anti-angiogenic agents, neuroprotective agents, agents for use in treating or preventing hyperpermeability disorders, as agents for treating pain, and as agents for reducing the risk of, or treatment of, pre-eclampsia.

The development of agents for directing expression of VEGF$_{xxx}$b isoforms represents a new era not only in the treatment of, for example, neovascular AMD, but all other diseases in which VEGF$_{xxx}$b is implicated.

The present invention is based in part on new small molecule inhibitors targeting SRPK1 specifically for use as anti-angiogenic agents, neuroprotective agents, agents for use in treating or preventing hyperpermeability disorders, as agents for treating pain, and as agents for reducing the risk of, or treatment of, pre-eclampsia.

The present invention is also based at least in part on the surprising finding that these low molecular weight compounds known to inhibit SRPK1 (e.g. SRPIN340 and derivatives and analogues thereof) could be used topically or in dose-dependent manner to inhibit CNV progression.

SUMMARY OF THE INVENTION

In a first aspect the invention provides a compound of Formula (I)

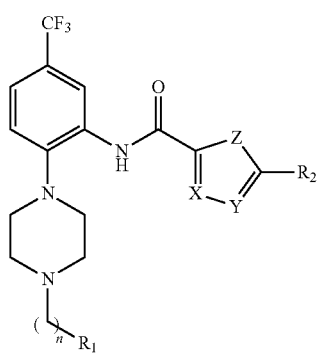

or a pharmaceutically acceptable salt, solvate, hydrate or prodrug thereof;
wherein:
n=1,2,3 or 0;
R$_1$=H; a 4- to 8-membered carbocyclic group, which may have one or more substituent; a 4- to 8-membered heterocyclic group comprising one oxygen atom, which may have one or more substituent;
a 4- to 8-membered heterocyclic group comprising one nitrogen atom, which may have one or more substituent, a 4- to 8-membered heterocyclic group comprising one nitrogen atom and one oxygen atom which may have one or more substituent; a 4- to 8-membered heterocyclic group comprising two nitrogen atoms which may have one or more substituent; a 4- to 8-membered heterocyclic group comprising three nitrogen atoms which may have one or more substituent, or a condensed aromatic heterocyclic group, which may have one or more substituent;
X=CH, O, NH or N;
Y=CH, O, NH or N;
Z=O, S, N or NH; and
R$_2$=H; a C$_{1-6}$ alkyl group; a phenyl group; a 4- to 8-membered heterocyclic group or a condensed aromatic heterocyclic group, each of which may have one or more substituent;
for use in dose-dependent treatment or prevention of ocular neovascularisation, The dose dependency is preferably a sigmoidal efficacy/dose relationship, e.g. of the type illustrated in FIG. 4C of the accompanying drawings. The expression "ocular neovascularisation" includes within its scope diseases and disorders characterised by ocular neovascularisation, including for example choroidal neovascularisation such as age-related macular degeneration. The term "ocular neovascularisation" also includes within its scope diseases and disorders characterized by retinal neovascularisation.

In a second aspect the invention provides a compound of formula (I) or a pharmaceutically acceptable salt, solvate, hydrate or prodrug thereof for use in the topical treatment or prevention of ocular neovascularisation.

The first and second aspects of the invention also provide respective methods of treatment or prevention of ocular neovascularisation by administration of the compound of formula (I) to a subject in need of such treatment, and respective uses of a compound of formula (I) in the preparation of a medicament for treatment or prevention of ocular neovascularisation, as a dose-dependent treatment and/or as a topical treatment.

It is surprising and not expected from the prior art that the compounds used in the present invention enable dose-dependent treatment or prevention of ocular neovascularisation or topical treatment or prevention of ocular neovascularisation. Dose-dependent treatment is not inherently predictable, yet is highly desirable and beneficial for effective treatment.

The specific compounds of formula (I), and preferred or exemplified sub-classes of compounds of formula (I) may be particularly mentioned for use in the present invention.

Further examples of the compounds of formula (I) that may be mentioned for use in the methods of the present invention are those in which R$_1$ is a 4- to 8-membered heterocyclic group comprising one nitrogen atom which may have one or more substituent. Examples of such compounds include those in which R$_1$ is a 6-membered heterocyclic aromatic group comprising one nitrogen atom, for example a 2- or 3- or 4-pyridyl group. Further examples of such compounds include those in which R$_1$ is a 6-membered heterocyclic aromatic ring comprising two or three nitrogen atoms, for example a pyrimidine ring, a pyridazine ring, a pyrazine ring, or a triazine ring, each of which may have one or more substituent. Further examples of such compounds include those in which R$_1$ is a 6-membered heterocyclic non-aromatic group comprising one nitrogen atom, for example a piperidine group or a piperazine group, each of which may have one or more substituent.

In one example, the compounds of Formula (I) include those in which R$_1$ is a nitrogen-containing 6-membered heteroaryl ring as described herein or a phenyl group, with any combination of n, X, Y, Z and R$_2$ as herein described.

For example, there are mentioned compounds in which $R_1$ is a nitrogen-containing 6-membered heteroaryl ring as described herein or a phenyl group; $R_2$ is H; a $C_{1-6}$ alkyl group; a phenyl group; a 4- to 8-membered heterocyclic group or a condensed aromatic heterocyclic group, each of which may have one or more substituent; X=Y=CH; Z=O and n=1.

For the avoidance of doubt,

refers to an alkyl bridging unit between the piperazine ring and $R_1$. Thus, the above mentioned moiety is a methylene ($CH_2$) bridge where n=1; an ethylene bridge ($CH_2CH_2$) where n=2; and a propylene bridge ($CH_2CH_2CH_2$) where n=3.

These compounds of formula (I) and their pharmaceutically acceptable salts, solvates, hydrates or prodrugs are new and as compounds per se (as well as their use in dose-dependent treatment or prevention of ocular neovascularisation and/or in the topical treatment or prevention of ocular neovascularisation) they constitute a further aspect of the present invention.

Pharmaceutical compositions comprising the novel compounds and the use of the novel compounds and pharmaceutical compositions comprising them in anti-angiogenic treatments (including the treatment and prevention of disorders and diseases characterised by abnormal or excessive angiogenesis), treatments of hyperpermeability disorders, treatments of neuropathic and neurodegenerative disorders, treatment of non-inflammatory pain and methods of reducing the risk of pre-eclampsia constitute further aspects of the present invention.

Thus, the present invention also provides (i) methods of treating or preventing disorders and diseases characterised by abnormal or excessive angiogenesis as defined herein; (ii) methods of treating or preventing hyperpermeability disorders as defined herein; (iii) methods of treating or preventing neuropathic and neurodegenerative disorders as defined herein; (iv) methods of treating or preventing non-inflammatory pain; and (v) methods of reducing the risk of pre-eclampsia, comprising administering a compound of Formula (I) to a patient in need thereof.

Particularly mentioned compounds of formula (I) include those in which n=1 or 2.

Particularly mentioned compounds of formula (I) include those in which X=Y=CH and Z=O; those in which one of X and Y=CH and the other of X and Y=N and Z=O; or those in which X=Y=N and Z=O.

Particularly mentioned compounds of formula (I) include those in which X=Y=CH and Z=S; those in which one of X and Y=CH and the other of X and Y=N and Z=S; or those in which X=Y=N and Z=S.

Particularly mentioned compounds of formula (I) include those in which X=Y=CH and Z=NH; those in which one of X and Y=CH and the other of X and Y=N and Z=NH; or those in which X=Y=N and Z=NH.

As preferred examples of the compounds of formula (I) there may be mentioned those in which $R_1$ is a 2- or 3- or 4-pyridyl group which may have one or more substituent, for example an unsubstituted 3-pyridyl group (namely, where the nitrogen heteroatom of the pyridyl group is meta to the 5-membered ring).

As preferred examples of the compounds of formula (I) there may be mentioned those in which $R_1$ is a phenyl group which may have one or more substituent, for example a methoxy substituent.

As preferred examples of the compounds of formula (I) there may be mentioned those in which $R_1$ is a condensed aromatic heterocyclic group which may have one or more substituent. For example, there may be mentioned those compounds in which $R_1$ is an indolyl group, an isoindolyl group, a benzimidazolyl group, a quinolyl group or an isoquinolyl group.

As preferred examples of the compounds of formula (I) there may be mentioned those in which $R_2$ is a 2- or 3- or 4-pyridyl group which may have one or more substituent, or a pyrimidinyl group. In the compounds of formula (I) in which $R_2$ is a 2- or 3- or 4-pyridyl group which may have one or more substituent, the 2- or 3- or 4-pyridyl group which may have one or more substituent may, for example, be an unsubstituted 3-pyridyl group (namely, where the nitrogen heteroatom of the pyridyl group is meta to the 5-membered ring).

As preferred examples of the compounds of formula (I) there may be mentioned those in which $R_2$ is a phenyl group which may have one or more substituent, or a condensed aromatic heterocyclic group, wherein the condensed aromatic heterocyclic group may comprise an indolyl group, an isoindolyl group, a benzimidazolyl group, a quinolyl group or an isoquinolyl group.

As preferred examples of the compounds of formula (I) there may be mentioned those in which $R_2$ is hydrogen or a $C_{1-6}$ alkyl group, for example a methyl group or an ethyl group.

For use in the first and second aspects of the present invention there may be mentioned as particularly preferred (a) the above compounds of formula (I) in which n=1; X=Y=CH and Z=O; $R_1$ is a 2- or 3- or 4-pyridyl substituent; $R_2$ is a phenyl substituent or a 2- or 3- or 4-pyridyl substituent, or a phenyl substituent or a 2- or 3- or 4-pyridyl group which may have one or more substituent; and (b) their pharmaceutically acceptable salts, solvates, hydrates or prodrugs. Examples of the compounds of formula (I) include compounds, the formulae of which are shown in Table 1 or Table 2.

The compounds of Formula (I) and their pharmaceutically acceptable salts, solvates, hydrates and prodrugs may be further characterized by one or more of the following features, which are, whether individually or in any combination, combinable with any of the examples and preferences stated herein, or in WO 2005/063293, for the compounds:

1. n=1;
2. $R_1$ may represent a phenyl group, a 2- or 3- or 4-pyridyl group, or a pyrimidinyl group;
3. Z=O;
4. X=Y=CH;
5. $R_2$ may represent a tetrahydropyranyl group, a phenyl group or a 2- or 3- or 4-pyridyl group.

The compounds represented by formula (I) include, for example:

(1) such compounds in which the above n=1 or 2;
(2) such compounds in which the above n=1;
(3) such compounds in which the above $R_1$ is a 4- to 8-membered carbocyclic group, which may have one or more substituent; a 4- to 8-membered heterocyclic group comprising one oxygen atom which may have one or more substituent or a 4- to 8-membered heterocyclic group comprising one or two nitrogen atoms which may have one or more substituent;
(4) such compounds in which the above $R_1$ is a 2- or 3- or 4-pyridyl group;
(5) such compounds in which the above X and Y are independently selected from CH or N;
(6) such compounds in which the above X and Y are both=CH
(7) such compounds in which the above Z=O or S or NH;
(8) such compounds in which the above Z=O;
(9) such compounds in which the above $R_2$ is hydrogen; a $C_{1-6}$ alkyl group; a 4- to 8-membered carbocycle which may have one or more substituent; a nitrogen-containing 4-to 8-membered heteroaryl ring which may have one or more substituent; or an oxygen-containing 4- to 8-membered heteroaryl ring which may have one or more substituent or a condensed aromatic heterocyclic group;
(10) such compounds in which the above $R_2$ is hydrogen, methyl or a nitrogen-containing 6-membered heteroaryl ring having one or more substituents;
(11) such compounds in which the above $R_2$ is a pyridyl ring or a pyrimidinyl ring which may have one or more substituent;
(12) such compounds in which the above $R_2$ is a 2- or 3- or 4-pyridyl ring.

In the compounds described above, n is preferred in the order of (1) to (2) with (2) preferred; $R_1$ is preferred in the order of (3) to (4), with (4) more preferred; X and Y are preferred in the order of (5) to (6), with (6) more preferred; Z is preferred in the order of (7) to (8), with (8) more preferred; $R_2$ is preferred in the order of (9) to (12), with (12) more preferred.

DETAILED DESCRIPTION OF THE INVENTION

The compounds of the present invention are SRPK1-specific inhibitors and may therefore be used in methods of treating or preventing any disease or condition in which SRPK1 is implicated. Such conditions and treatments will now be described.

Anti-angiogenic treatments

The compounds of the present invention may be used in anti-angiogenic treatments. The anti-angiogenic treatment preferably includes the treatment or prevention of any disease or disorder associated with abnormal angiogenesis or abnormal over-production of pro-angiogenic VEGF isoforms ($VEGF_{xxx}$). Such diseases and disorders include, for example, vascular disease (e.g. vasoconstriction and disorders characterised by vasoconstriction, and cardiovascular disease), malignant and benign neoplasia (e.g. angiogenesis-dependent cancers, for example tumorous cancers), tumor metastasis, inflammatory disorders, diabetes, diabetic retinopathy and other complications of diabetes (e.g. diabetic neovascularisation), trachoma, retrolental hyperplasia, neovascular glaucoma, age-related macular degeneration, haemangioma, immune rejection of implanted corneal tissue, corneal angiogenesis associated with ocular injury or infection, Osler-Webber Syndrome, myocardial angiogenesis, wound granulation, telangiectasia, hemophiliac joints, angiofibroma, telangiectasia psoriasis scleroderma, pyogenic granuloma, rubeosis, obesity, arthritis (e.g. rheumatoid arthritis), hematopoieses, vasculogenesis, gingivitis, atherosclerosis, endometriosis, neointimal hyperplasia, psoriasis, hirsutism and proliferative retinopathy. The anti-angiogenic treatment according to the present invention may also include non-therapeutic treatments performed on healthy subjects, for example to inhibit vascular development for cosmetic purposes. For further details on diseases and disorders associated with abnormal angiogenesis, and on anti-angiogenic treatments, see WO 2008/110777, the contents of which are incorporated herein by reference.

In particular, the compounds of the present invention may be used in the treatment or prevention of ocular neovascularisation, which may include retinal neovascularisation or choroidal neovascularisation or age-related macular degeneration. In addition, the compounds of the present invention may be used in the treatment or prevention of malignant neoplasias or cancers, for example prostate cancer and breast cancer.

Microvascular Hyperpermeability Disorders, Disorders of Epithelial Cell Survival and Disorders of Fenestrations of Epithelial Filtration Membranes The compounds of the present invention, as SRPK1 inhibitors, may also be used as therapeutic agents in treating other disorders in which the alternatively spliced $VEGF_{xxx}b$ isoform has been implicated. For example, it has been shown in WO 2010/058227, the contents of which are incorporated herein by reference, that $VEGF_{xxx}b$ is active against a range of microvascular hyperpermeability disorders, disorders of epithelial cell survival and disorders of fenestrations of epithelial filtration membranes.

Microvascular hyperpermeability, disorders of regulation of the pro-angiogenic pro-permeability properties of $VEGF_{xxx}$ isoforms, disorders of epithelial cell survival and permeability, and/or disorders in the nature (for example the number density and/or size) of fenestrations of epithelial filtration membranes underlie a number of serious medical conditions.

Examples of such conditions include, for example, proteinuria, uraemia, microalbuminuria, hypoalbuminemia, renal hyperfiltration, nephrotic syndrome, renal failure, pulmonary hypertension, capillary hyperpermeability, microaneurysms, oedema and vascular complications of diabetes.

Examples of such vascular complications of diabetes include, for example, diabetic retinopathy, both proliferative and non-proliferative, and diabetic nephropathy. Vascular complications of diabetes can be associated with either Type I or Type II diabetes.

The loss of proteins from the blood can lead to further complications, for example thromboses, especially thromboses in the brain, and susceptibility to infections. Loss of natural proteins from the blood can seriously impair the efficacy of cancer therapies.

The microvascular hyperpermeability disorder may particularly be a renal disorder, for example a permeability disorder of the GFB, for example a permeability disorder of the podocytes.

Examples of disorders where treatment to support epithelial cell survival would be effective are as follows:

acute pulmonary fibrotic disease, adult respiratory distress syndrome, adult respiratory distress syndrome, advanced cancer, allergic respiratory disease, alveolar injury, angiogenesis, arthritis, ascites, asthma, asthma or edema following burns, atherosclerosis, autoimmune diseases, bone resorption, bullous disorder associated with subepidermal blister formation including bullous pemphigoid, cardiovascular condition, certain kidney diseases associated with proliferation of glomerular or mesangial cells, chronic and allergic inflammation, chronic lung disease, chronic occlusive pulmonary disease, cirrhosis, corneal angiogenisis, corneal disease, coronary and cerebral collateral vascularization, coronary restenosis, damage following heart disease, dermatitis herpetiformis, diabetes, diabetic nephropathy, diabetic retinopathy, endotoxic shock, erythema multiforme, fibrosis, glomerular nephritis, glomerulonophritis, graft rejection, gram negative sepsis, hemangioma, hepatic cirrhosis, hepatic failure, Herpes Zoster, host-versus-graft reaction (ischemia reperfusion injury and allograft rejections of kidney, liver, heart, and skin), impaired wound healing in infection, infection by Herpes simplex, infection from human immunodeficiency virus (HIV), inflammation, cancer, inflammatory bowel disease (Crohn's disease and ulcerative colitis), inflammatory conditions, in-stent restenosis, in-stent stenosis, ischemia, ischemic retinal-vein occlusion, ischemic retinopathy, Kaposi's sarcoma, keloid, liver disease during acute inflammation, lung allograft rejection (obliterative bronchitis), lymphoid malignancy, macular degeneration retinopathy of prematurity, myelodysplastic syndromes, myocardial angiogenesis, neovascular glaucoma, non-insulin-dependent diabetes mellitus (NIDDM), obliterative bronchiolitis, ocular conditions or diseases, ocular diseases associated with retinal vessel proliferation, Osier-Weber-Rendu disease, osteoarthritis, ovarian hyperstimulation syndrome, Paget's disease, pancreatitis, pemphigoid, polycystic kidney disease, polyps, postmenopausal osteoporosis, preeclampsia, psoriasis, pulmonary edema, pulmonary fibrosis, pulmonary sarcoidosis, restenosis, restenosis, retinopathy including diabetic retinopathy, retinopathy of prematurity and age related macular degeneration; rheumatoid arthritis, rheumatoid arthritis, rubeosis, sarcoidosis, sepsis, stroke, synovitis, systemic lupus erythematosus, throiditis, thrombic micoangiopathy syndromes, transplant rejection, trauma, tumor-associated angiogenesis, vascular graft restenosis, vascular graft restenosis, von Hippel Lindau disease, wound healing.

The present invention may be used in the treatment of macular dystrophy. This includes: Stargardt disease/fundus flavimaculatus; Stargardt-like macular dystrophy; Stargardt-like macular dystrophy; Autosomal dominant "bull'seye" macular dystrophy Best macular dystrophy; Adult vitelliform dystrophy; Pattern dystrophy; Doyne honeycomb retinal dystrophy; North Carolina macular dystrophy; Autosomal dominant macular dystrophy resembling MCDR1; North Carolina-like macular dystrophy associated with deafness; Progressive bifocal chorioretinal atrophy; Sorsby's fundus dystrophy; Central areolar choroidal dystrophy; Dominant cystoid macular dystrophy; Juvenile retinoschisis; Occult Macular Dystrophy; Non-familial Occult Macular Dystrophy.

The disorder may particularly be a disorder of the retinal epithelium, such as geographic atrophy, or age related macular degeneration.

For further details on of microvascular hyperpermeability disorders, disorders of epithelial cell survival and disorders of fenestrations of epithelial filtration membranes, and the treatment thereof, see WO 2010/058227, the contents of which are incorporated herein by reference.

Neuropathic and Neurodegenerative Disorders

The compounds of the present invention, as SRPK1 inhibitors, may also be used as therapeutic agents in treating other disorders in which the alternatively spliced $VEGF_{xxx}b$ isoform has been implicated. For example, it has been shown in WO 2009/106855, the contents of which are incorporated herein by reference, that $VEGF_{xxx}b$ has neuroprotective and neuroregenerative effects.

Neuropathic disorders to be treated or prevented according to the present invention include neuropathic pain and diabetic and other neuropathies.

Neurodegenerative disorders to be treated or prevented according to the present invention include neurodegeneration of the cognitive and non-cognitive types, neuromuscular degeneration, motor-sensory neurodegeneration, ocular neurodegeneration.

The activities of the proteins of the $VEGF_{xxx}b$ family are predicted to both actively prevent and actively' reverse the conditions and disorders.

Furthermore, since mild cognitive dysfunction is often associated with the normal state in certain classes of healthy people, for example the aged, persons under stress, tired or exhausted persons, the present invention is also applicable to non-therapeutic treatments of healthy people to adjust or normalise their cognitive function and behaviour, including thinking, memory, learning, concentration and reasoning.

Still further, since neuroregeneration can assist in normalising brain neural networks in subjects having psychiatric or behavioural abnormalities, whether or not these are diagnosable as one or more recognised psychiatric condition, the present invention is also applicable to therapeutic treatment persons having psychiatric disorders and to non-therapeutic treatment of physically healthy people to adjust their cognition and behaviour towards the normal state.

For example, the present invention provides for the treatment or prevention of: pain (for example, neuropathic pain), dementia, age-related cognitive impairment, Alzheimer's disease, senile dementia of the Alzheimer's type (SDAT), Lewy body dementia, vascular dementia, Parkinson's disease, postencephalitic Parkinsonism, depression, schizophrenia, muscular dystrophy including facioscapulobumeral muscular dystrophy (FSH), Duchenne muscular dystrophy, Becker muscular dystrophy and Bruce's muscular dysrophy, Fuchs' dystrophy, myotonic dystrophy, corneal dystrophy, reflex sympathetic dystrophy syndrome (RSDSA), neurovascular dystrophy, myasthenia gravis, Lambert Eaton disease, Huntington's disease, motor neurone diseases including amyotrophic lateral sclerosis (ALS), multiple sclerosis, postural hypotension, traumatic neuropathy or neurodegeneration e.g. following stroke or following an accident (for example, traumatic head injury or spinal cord injury), Batten's disease, Cockayne syndrome, Down syndrome, corticobasal ganglionic degeneration, multiple system atrophy, cerebral atrophy, olivopontocerebellar atrophy, dentatorubral atrophy, pallidoluysian atrophy, spinobulbar atrophy, optic neuritis, sclerosing pan-encephalitis (SSPE), attention deficit disorder, post-viral encephalitis, post-poliomyelitis syndrome, Fahr's syndrome, Joubert syndrome, Guillain-Barre syndrome, lissencephaly, Moyamoya disease, neuronal migration disorders, autistic syndrome, polyglutamine disease, Niemann-Pick disease, progressive multifocal leukoencephalopathy, pseudotomer cerebri, Refsum disease, Zellweger syndrome, supranuclear palsy, Friedreich's ataxia, spinocerebellar ataxia type 2, Rhett syndrome, Shy-Drager syndrome, tuberous sclerosis, Pick's disease, chronic fatigue syndrome, neuropathies including hereditary neuropathy, diabetic neuropathy and mitotic neuropathy, prion-based neurodegeneration, including Creutzfeldt-Jakob disease (CJD), variant CJD, new variant CJD, bovine spongiform encephalopathy (BSE), GSS, FFI, kuru and Alper's syndrome, Joseph's disease, acute disseminated encephalomyelitis, arachnoiditis, vascular lesions of the central nervous system, loss of extremity neuronal function, Charcot-Marie-Tooth disease, Krabbe's disease, leukodystrophies, susceptibility to heart failure, asthma, epilepsy, auditory neurodegeneration, muscular degeneration, pigmentary retinitis and glaucoma-induced optic nerve degeneration.

Generally speaking, mental disorders are not diagnosed as "psychiatric disorders" unless the associated behaviours or thoughts cause significant distress to the individual or are disruptive of his or her everyday functioning There is therefore a borderline between diagnosable disorders and similar, but less severe or disruptive, psychological functions the treatment of which should be considered as non-therapeutic (see below).

Examples of psychiatric disorders with which the present invention is concerned include, without limitation: anxiety disorders (for example, acute stress disorder, panic disorder, agoraphobia, social phobia, specific phobia, obsessive-compulsive disorder, sexual anxiety disorders, post-traumatic stress disorder, body dysmorphic disorder and generalized anxiety disorder), childhood disorders (for example, attention-deficit hyperactivity disorder (ADHD), Asperger's disorder, autistic disorder, conduct disorder, oppositional defiant disorder, separation anxiety disorder and Tourette's disorder), eating disorders (for example, anorexia nervosa and bulimia nervosa), mood disorders (for example, depression, major depressive disorder, bipolar disorder (manic depression), seasonal affective disorder (SAD), cyclothymic disorder and dysthymic disorder), sleeping disorders, cognitive psychiatric disorders (for example, delirium, amnestic disorders), personality disorders (for example, paranoid personality disorder, schizoid personality disorder, schizotypal personality disorder, antisocial personality disorder, borderline personality disorder, histrionic personality disorder, narcissistic personality disorder, avoidant personality disorder, dependent personality disorder and obsessive- compulsive personality disorder), psychotic disorders (for example, schizophrenia, delusional disorder, brief psychotic disorder, schizophreniform disorder, schizoaffective disorder and shared psychotic disorder), and substance-related disorders (for example, alcohol dependence, amphetamine dependence, cannabis dependence, cocaine dependence, hallucinogen dependence, inhalant dependence, nicotine dependence, opioid dependence, phencyclidine dependence and sedative dependence).

For further details on neuropathic and neurodegenerative disorders, and the treatment thereof, see WO 2009/106855, the contents of which are incorporated herein by reference.

Treatment of Pain

The compounds of the present invention, as SRPK1 inhibitors, may also be used as therapeutic agents in treating other disorders in which the alternatively spliced VEGF$_{xxx}$b isoform has been implicated. For example, it has been shown in WO 2011/148200, the contents of which are incorporated herein by reference, that VEGF$_{xxx}$b has an analgesic effect on VEGFR2-mediated non-inflammatory pain in mammals.

VEGFR2-mediated non-inflammatory pain to be treated or prevented according to the present invention includes non-inflammatory neuropathic and nociceptive pain where the VEGFR2 receptor is involved in the cause or transmission of the pain. For example, the compounds according to the present invention are predicted to have activity against non-inflammatory allodynia and pain (antiallodynic and analgesic activity). Pain states of this type include chronic pain, whether of the intermittent or constant form.

Such pain states may include, for example, low back pain, neuralgia, atypical pains such as atypical facial pain, pain exhibited post-surgery, post-injury (for example, after surgery or injury causing nerve damage) or in association with cancer or with cancer therapy such as cytotoxic or radiation therapy, or neuropathy associated with diabetes (diabetic neuropathy, insulin neuritis) or other systemic or autoimmune disease or pathology, or the treatment thereof, alcoholism or HIV infection, ageing associated neuropathy, or neuropathy of unknown origin.

The activities of the proteins of the VEGFR2 agonists, for example the VEGF$_{xxx}$b family, are predicted to both actively prevent and actively reverse VEGFR2-mediated non-inflammatory pain.

However, in view of the anti-angiogenic activity of the proteins of the VEGF$_{xxx}$b family, use of the compounds of the present invention will be restricted to pain in contexts where possible inhibition of angiogenesis would not be detrimental to the patient.

The compounds used in the present invention may be employed in association with one or more different pain treatment agent for the purpose of normalising the sensitivity towards pain of the subject treated (or being co-treated) with the said one or more different pain treatment agent. The term "normalising" means moving the subject's pain sensitivity towards normal levels, and may include enhancement of the sensitivity if the one or more different pain treatment agent causes an excessive reduction in feeling or in sensitivity towards pain. The one or more different pain treatment agent may be selected from pain treatment agents currently known or yet to be devised. Such selection will be well within the skill of the person of ordinary skill in this art. Such combination treatments can enable fine control of pain sensitivity in subjects and minimisation of overall side effects according to the particular condition and needs of the subject.

For further details on pain, and the treatment thereof, see WO 2011/148200, the contents of which are incorporated herein by reference.

Reduction of Risk of Pre-Eclampsia

The compounds of the present invention, as SRPK1 inhibitors, may also be used as therapeutic agents in treating other disorders in which the alternatively spliced VEGF$_{xxx}$b isoform has been implicated. For example, it has been shown in WO 2011/036429, the contents of which are incorporated herein by reference, that reduced VEGF$_{xxx}$b levels in pregnant female mammals increase the risk of the female mammal developing pre-eclampsia. Thus, compounds of the present invention may be used to increase VEGF$_{xxx}$b levels in a pregnant female mammal so as to reduce the risk of pre-eclampsia the female mammal developing pre-eclampsia or a complication linked thereto, or of a fetus of the female mammal developing a fetal or neonatal deficiency linked to maternal pre-eclampsia.

Pre-eclampsia in humans can develop as early as 20 weeks of gestation. Pre-eclampsia that develops before about 34 weeks of gestation is normally referred to as "early pre-eclampsia" or "early-onset pre-eclampsia" Pre-eclampsia that develops after about 34 weeks of gestation is normally referred to as "late pre-eclampsia" or "late-onset pre-eclampsia".

In addition, pre-eclampsia can be categorised as "severe pre-eclampsia" according to criteria established by the United Kingdom Royal College of Obstetricians and Gynaecologists. Under these criteria, a patient with "severe pre-eclampsia" will have systolic blood pressure (BP) greater than 169 mmHg or diastolic BP greater than 109 mmHg with proteinuria greater than 1 g/24 h; or will show occurrence of HELLP syndrome (haemolysis, elevated liver enzymes and low platelet count).

For further details on pre-eclampsia, and methods to reduce the risk of a pregnant female mammal developing developing pre-eclampsia or a complication linked thereto, or of a fetus of the female mammal developing a fetal or neonatal deficiency linked to maternal pre-eclampsia, see WO 2011/036429, the contest of which are incorporated herein by reference.

Active Compounds

Compounds of the present invention are as defined by Formula (I) and have been shown to be inhibitors of one or both of the kinases SRPK1, and SRPK2, and thus useful in treatments as described herein.

The compounds of the present invention may be synthesised by any known method. Suitable methods as disclosed in WO 2005/063293 may be adapted as required. An exemplary synthesis for compound 12 is described below in the Examples.

Co-Administration

The compounds of the present invention may, if desired, be co-administered with one or more additional active agent, for example one or more agent selected from, but not limited to, cholinesterase inhibitors, dopamine agonists (e.g. L-dopa), COMT inhibitors, MAO-B inhibitors, anti-cholinergics, acetylcholine agonists, serotonin agonists, AMPA receptor agonists, GABA receptor agonists, NMDA receptor agonists, β-adrenoceptor agonists, digoxin, dobutamine, anti-inflammatories, neurotrophic factors, statins, adenosine A2a receptor antagonists, aldose reductase inhibitors, immunomodulators, cannabinoid agonists, interferon or tricyclic anti-depressants.

Definitions

In the definition of formula (I) herein:

"$C_{1-6}$ alkyl group" refers to a linear or branched alkyl group comprising one to six carbon atoms, which is a monovalent group derived by removing an arbitrary hydrogen atom from an aliphatic hydrocarbon consisting of one to six carbons. Specifically, the $C_{1-6}$ alkyl group includes, for example, a methyl group, an ethyl group, a 1-propyl group, a 2-propyl group, a 2-methyl-1-propyl group, a 2-methyl-2-propyl group, a 1-butyl group, a 2-butyl group, a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group, and a 2,3-dimethyl-2-butyl group;

"heterocycle" or "heterocyclic group" refers to an aromatic or non-aromatic ring that may comprise double bonds within the ring, wherein at least one, for example one or two, of the atoms constituting the ring are heteroatoms;

"nitrogen-containing heterocycle" or "heterocyclic group comprising one or more nitrogen atoms" refers to an aromatic or non-aromatic ring that may comprise double bonds within the ring, wherein at least one, for example one or two, of the atoms constituting the ring are nitrogen atoms;

"oxygen-containing heterocycle" or "heterocyclic group comprising one or more oxygen atoms" refers to an aromatic or non-aromatic ring that may comprise double bonds within the ring, wherein at least one, for example one or two, of the atoms constituting the ring are oxygen atoms;

"heteroatom" refers to a sulfur atom, an oxygen atom, or a nitrogen atom;

"nitrogen-containing 5- to 10-membered heteroaryl ring" or "nitrogen-containing 5- to 10-membered heteroaromatic group" refers to an aromatic ring in which five to ten atoms constitute the ring, wherein at least one of the atoms constituting the ring is a nitrogen atom, and one or more heteroatoms other than nitrogen atoms may further be comprised. Specifically, the nitrogen-containing 5- to 10-membered heteroaryl ring includes, for example, a pyridine ring, an indole ring, an isoindole ring, a pyridazine ring, a pyrimidine ring, a pyrazine ring, a quinoline ring, an isoquinoline ring, and a benzimidazole ring;

"nitrogen-containing 5- to 10-membered heteroaryl group" refers to a mono- or divalent group derived by removing one or two, arbitrary hydrogen atoms from the above-defined "5- to 10-membered heteroaryl ring". Specifically, the nitrogen-containing 5- to 10-membered heteroaryl group includes, for example, a pyridyl group, an indolyl group, an isoindolyl group, a pyridazinyl group, a pyrimidinyl group, a pyrazinyl group, a quinolyl group, an isoquinolyl group, and a benzimidazolyl group;

"nitrogen-containing 4- to 8-membered heteroaryl ring" or "nitrogen-containing 4- to 8- membered. heteroaromatic group" refers to an aromatic ring in which four to eight atoms constitute the ring, wherein at least one of the atoms constituting the ring is a nitrogen atom, and one or more heteroatoms other than nitrogen atoms may further be comprised. Specifically, the nitrogen-containing 4- to 8-membered heteroaryl ring includes, for example, a pyridine ring, a pyridazine ring, a pyrimidine ring, and a pyrazine ring;

"nitrogen-containing 4- to 8-membered heteroaryl group" refers to a mono-or divalent group derived by removing one or two arbitrary hydrogen atoms from the above-defined "4- to 8-membered heteroaryl ring". Specifically, the nitrogen-containing 4- to 8-membered heteroaryl group includes, for example, a pyridyl group, a pyridazinyl group, a pyrimidinyl group, and a pyrazinyl group;

"oxygen-containing 5- to 10-membered heteroaryl ring" refers to an aromatic ring in which five to ten atoms constitute the ring, wherein at least one of the atoms constituting the ring is an oxygen atom, and one or more heteroatoms other than oxygen atoms may further be comprised. Specifically, the oxygen-containing 5- to 10-membered heteroaryl ring includes, for example, a pyran ring;

"oxygen-containing 4- to 8-membered heteroaryl group" refers to an aromatic ring in which four to eight atoms constitute the ring, wherein at least one of the atoms constituting the ring is an oxygen atom, and one or more heteroatoms other than oxygen atoms may further be comprised, for example a pyranyl group;

"4- to 8-membered non-aromatic heterocyclic ring" refers to a non-aromatic ring that meets the following definition:
1. four to eight atoms constitute the ring;
2. one or two of the atoms constituting the ring are heteroatoms;
3. one or two double bonds may be comprised in the ring;
4. one to three carbonyl groups may be comprised in the ring; and
5. the group is monocyclic.

The 4- to 8-membered non-aromatic heterocyclic ring is preferably a nitrogen-containing 4- to 8-membered heterocyclic ring that comprises nitrogen atoms as heteroatoms.

Specifically, the 4- to 8-membered non-aromatic heterocyclic ring includes, for example, an azetidine ring, a pyrrolidine ring, a piperidine ring, an azepane ring, an azocine ring, a tetrahydrofuran ring, a tetrahydropyran ring, a morpholine ring, a thiomorpholine ring, a piperazine ring, a thiazolidine ring, a dioxane ring, an imidazoline ring, and a thiazoline ring. The "4- to 8-membered heterocyclic ring" preferably includes a pyrrolidine ring, a piperidine ring, a morpholine ring, and a piperazine ring;

"4- to 8-membered non-aromatic heterocyclic group" refers to a mono- or divalent group derived by removing one or two arbitrary hydrogen atoms from the above-defined "4- to 8-membered non-aromatic heterocyclic ring". Specifically, the 4- to 8-membered heterocyclic group includes, for example, an azetidinyl group, a pyrrolidinyl group, a piperidinyl group, an azepanyl group, an azocanyl group, a tetrahydrofuryl group, a tetrahydropyranyl group, a morpholinyl group, a thoimorpholinyl group, a piperazinyl group, a thiazolidinyl group, a dioxanyl group, an imidazolyl group, and a thiazolyl group;

"Condensed aromatic heterocycle" refers to a ring structure in which the heterocyclic moiety is fused, for example ortho-condensed, with an aromatic ring, such as a benzene ring. The heterocyclic moiety is an above-defined heterocycle.

"Condensed aromatic heterocyclic group" refers to a ring structure in which the heterocyclic moiety is fused, for example ortho-condensed, with a ring, for example an aromatic ring, such as benzene ring. The heterocyclic moiety is an above-defined heterocyclic group.

The condensed aromatic heterocyclic group includes, for example, an indolyl group, an indolinyl group, an isoindolyl group, an isoindolinyl group, and a 1,2,3,4-tetrahydroquinoline.

"4- to 8-membered carbocyclic ring" refers to a saturated or unsaturated carbon ring, for example a furan ring, a tetrahydrofuran ring, a pyran ring or a tetrahydropyran ring;

"4- to 8-membered carbocyclic group" refers to a saturated refers to a mono- or divalent group derived by removing one or two arbitrary hydrogen atoms from the above-defined 4- to 8-membered carbocyclic ring. Specifically, "4- to 8-membered carbocyclic group" may refer to a furanyl group, a tetrahydrofuranyl group, a pyranyl group or a tetrahydropyranyl group;

Herein, "halogenated $C_{1-6}$ alkyl group" refers to a group in which at least one arbitrary hydrogen atom in the above-defined "$C_{1-6}$ alkyl group" is replaced with an above-defined "halogen atom". The halogenated $C_{1-6}$ alkyl group includes, for example, a trifluoromethyl group, a difluoromethyl group, and a monofluoromethyl group.

Herein, the phrase "may have one or more substituent" means that a certain group or compound may optionally have an arbitrary selection or combination of one or more substituent at substitutable positions. Specifically, the substituents can include, for example, atoms or groups selected from one or more of: halogen, hydroxyl, hydroxymethyl, hydroxyethyl, mercapto, nitro, cyano, formyl, carboxyl, trifluoromethyl, trifluoromethoxy, amino, oxo, imino, $C_{1-6}$ alkyl (for example methyl), $C_{1-4}$ alkoxy (for example, methoxy), $C_{1-6}$ thioalkyl (for example thiomethyl), $C_{2-6}$ alkenyl, $C_{2-6}$ alkenyl; $C_{1-6}$ alkoxycarbonyl, $C_{1-6}$ alkylsulfonyl, $C_{6-10}$ aryl, benzyl, heteroaryl, phenyl, or $C_{6-10}$ aryl or benzyl or phenyl or heteroaryl substituted by one or more of halogen, hydroxyl, hydroxymethyl, hydroxyethyl, mercapto, nitro, cyano, formyl, carboxyl, trifluoromethyl, trifluoromethoxy, amino, oxo, imino, $C_{1-6}$ alkyl (for example methyl), $C_{1-6}$ thioalkyl (for example thiomethyl), $C_{2-6}$ alkenyl, $C_{2-6}$ alkynyl; $C_{1-6}$ alkoxycarbonyl, $C_{1-6}$ alkylsulfonyl, or $C_{1-6}$ alkoxy (for example, methoxy).

"$C_{2-6}$ alkenyl group" refers to a linear or branched alkenyl group comprising two to six carbons. Specifically, the $C_{2-6}$ alkenyl group includes, for example, a vinyl group, an allyl group, a 1-propenyl group, a 2-propenyl group, a 1-butenyl group, a 2-butenyl group, a 3-butenyl group, a pentenyl group, and a hexenyl group;

"$C_{2-6}$ alkynyl group" refers to a linear or branched alkynyl group comprising two to six carbons. Specifically, the $C_{2-6}$ alkynyl group includes, for example, an ethynyl group, a 1-propynyl group, a 2-propynyl group, a butynyl group, a pentynyl group, and a hexynyl group.

"$C_{1-6}$ alkoxy group" refers to an oxy group to which the above-defined "$C_{1-6}$ alkyl group" is linked. Specifically, the $C_{1-6}$ alkoxy group includes, for example, a methoxy group, an ethoxy group, a 1-propyloxy group, a 2-propyloxy group, a 2-methyl-1-propyloxy group, a 2-methyl-2-propyloxy group, a 1-butyloxy group, a 2-butyloxy group, a 1-pentyloxy group, a 2-pentyloxy group, a 3-pentyloxy group, a 2-methyl-1-butyloxy group, a 3-methyl-1-butyloxy group, a 2-methyl-2-butyloxy group, a 3-methyl-2-butyloxy group, a 2,2-dimethyl-1-propyloxy group, a 1-hexyloxy group, a 2-hexyloxy group, a 3-hexyloxy group, a 2-methyl-1-pentyloxy group, a 3-methyl-1-pentyloxy group, a 4-methyl-1-pentyloxy group, a 2-methyl-2-pentyloxy group, a 3-methyl-2-pentyloxy group, a 4-methyl-2-pentyloxy group, a 2-methyl-3-pentyloxy group, a 3-methyl-3-pentyloxy group, a 2,3-dimethyl-1-butyloxy group, a 3,3-dimethyl-1-butyloxy group, a 2,2-dimethyl-1-butyloxy group, a 2-ethyl-1-butyloxy group, a 3,3-dimethyl-2-butyloxy group, and a 2,3-dimethyl-2-butyloxy group;

"$C_{1-6}$ alkylthio group" refers to a thio group to which the above-defined "$C_{1-6}$ alkyl group" is linked. Specifically, the "$C_{1-6}$ alkylthio group" includes, for example, a methylthio group, an ethylthio group, a 1-propylthio group, a 2-propylthio group, a butylthio group, and a pentylthio group;

"$C_{1-6}$ alkoxycarbonyl group" refers to a carbonyl group to which the above-defined "$C_{1-6}$ alkoxy group" is linked. Specifically, the $C_{1-6}$ alkoxycarbonyl group includes, for example, a methoxy carbonyl group, an ethoxy carbonyl group, a 1-propyloxycarbonyl group, and a 2-propyloxycarbonyl group;

"$C_{1-6}$ alkylsulfonyl group" refers to a sulfonyl group to which the above-defined "$C_{1-6}$ alkyl group" is linked. Specifically, the $C_{1-6}$ alkylsulfonyl group includes, for example, a methylsulfonyl group, an ethylsulfonyl group, a 1-propylsulfonyl group, and a 2-propylsulfonyl group.

"halogen atom" refers to a fluorine atom, a chlorine atom, a bromine atom, or an iodine atom;

"$C_{6-10}$ aryl group" refers to an aromatic cyclic hydrocarbon group comprising six to ten carbon atoms. Specifically, the $C_{6-10}$ aryl group includes, for example, a phenyl group, a 1-naphthyl group, and a 2-naphthyl group;

"Salt" is not particularly limited, so long as it is a pharmaceutical acceptable salt which is formed with a compound according to the present invention. Such salts include, for example, inorganic acid salts, organic salts, inorganic base salts, organic base salts, and acidic or basic amino acid salts. Examples of preferable inorganic acid salts include: hydrochloride, hydrobromate, sulfate, nitrate, and phosphate. Examples of preferable organic salts include: acetate, succinate, fumarate, maleate, tartrate, citrate, lactate, stearate, benzoate, methanesulfonate, and p-toluene sulfonate.

Examples of preferable inorganic base salts include: alkali metal salts, such as sodium salts and potassium salts; alkali earth metal salts, such as calcium salts and magnesium salts; aluminium salts; and ammonium salts. Examples of preferable organic base salts include: diethylamine salts, diethanol amine salts, meglumine salts, and N,N'-dibenzylethylenediamine salts.

Examples of preferable acidic amino acid salts include: aspartate and glutamate. Examples of preferable basic amino acid salts include; arginine salts, lysine salts, and ornithine salts.

When left in air, the compounds of the present invention sometimes absorb moisture, and are sometimes attached to absorbed water or converted to hydrates. Such hydrates are also included in the present invention.

Furthermore, compounds of the present invention are sometimes converted into solvates, absorbing some other solvents. Such solvates are also included in the present invention.

Any organic solvent may in principle be used to prepare a solvate of the compounds of the present invention.

A solvate can include also water together with the one or more organic solvent.

Thus, for example, the solvent may be selected from ketones, alcohols, ethers, esters, aromatic solvents, and, where possible, mixtures thereof with each other, with other organic solvents and/or with water.

Pharmaceutically acceptable prodrug forms of the compounds of formula (I) may be used in the present invention, "Pharmaceutically acceptable prodrugs" means those prodrugs of the compounds which are, within the scope of sound medical and vetinary judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds. The term "prodrug" means compounds that are rapidly transformed in vivo to yield the parent compound of the above formula, for example, by hydrolysis in blood. Functional groups which may be rapidly transformed, by metabolic cleavage, in vivo form a class of groups reactive with the carboxyl group. Because of the ease with which the metabolically cleavable groups of the compounds are cleaved in vivo, the compounds bearing such groups act as pro-drugs. A thorough discussion of prodrugs is provided in the following: Design of Prodrugs, H. Bundgaard, ed., Elsevier, 1985; Methods in Enzymology, K. Widder et al, Ed., Academic Press, 42, p. 309-396,1985; A Textbook of Drug Design and Development, Krogsgaard-Larsen and H. Bundgaard, ed., Chapter 5; Design and Applications of Prodrugs p. 113-191, 1991; Advanced Drug Delivery Reviews, H. Bundgaard, 8, p. 1-38, 1992; Journal of Pharmaceutical Sciences, 77, p. 285,1988; Chem. Pharm. Bull., N. Nakeya et al, 32, p. 692,1984; Pro-drugs as Novel Delivery Systems, T. Higuchi and V. Stella, Vol. 14 of the A. C. S. Symposium Series, and Bioreversible Carriers in Drug Design, Edward B. Roche, ed., American Pharmaceutical Association and Pergamon Press. 1987, which are incorporated herein by reference.

Compositions and Administration

The compound according to the present invention may be administered in the form of a composition comprising the active agent and any suitable additional component. The composition may, for example, be a pharmaceutical composition (medicament), suitably for topical administration (e.g. as eyedrops or cream or lotion), or parenteral administration (e.g. injection, implantation or infusion). The composition may alternatively, for example, be a foodstuff, food supplement, beverage or beverage supplement.

The term "pharmaceutical composition" or "medicament" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may take the form, for example, of tablets, dragees, powders, elixirs, syrups, liquid preparations including suspensions, sprays, inhalants, tablets, lozenges, emulsions, solutions, cachets, granules, capsules and suppositories, as well as liquid preparations for injections, including liposome preparations. Techniques and formulations generally may be found in Remington, The Science and Practice of Pharmacy, Mack Publishing Co., Easton, Pa., latest edition.

Liquid form preparations include solutions, suspensions, and emulsions. As an example may be mentioned water or water-propylene glycol solutions for parenteral injection or topical administration. Liquid preparations can also be formulated in solution in aqueous polyethylene glycol solution.

Also included are solid form preparations which are intended to be converted, shortly before use, to liquid form preparations for either topical, oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container or apparatus. The solid form preparations intended to be converted to liquid form may contain, in addition to the active material, flavourings, colourants, stabilizers, buffers, artificial and natural sweeteners, dispersants, thickeners, solubilising agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for topical or parenteral use, The composition may be in a formulation intended for topical application. The formulation may be a gelling formulation to control release and therefore availability of the active agent following topical application. The formulation may contain one or more gelling agents, for example hydroxypropyl methylcellulose. The formulation may contain one or more surfactants, for example a non-ionic liquid polymer, examples of which include Tyloxapol, and the Pluronics® poloxamers from BASF. The formulation may contain one or more solubilizers, for example dextrose or sorbitol. The formulation may contain one or more antimicrobial or antiseptic agents, for example benzalkonium chloride. The aforementioned named gelling agents, surfactants, solubilizers and antimicrobial agents are listed purely by way of example and it will be appreciated that other agents to perform these functions are known.

The dosages may be varied depending upon the requirements of the patient, the severity of the condition being treated, and the compound being employed. Determination of the proper dosage for a particular situation is within the skill of the art. Generally, treatment is initiated with the smaller dosages which are less than the optimum dose of the compound. Thereafter the dosage is increased by small increments until the optimum effect under the circumstances is reached. For convenience, the total daily dosage may be divided and administered in portions during the day if desired.

The dosage regime for administration of the active agent may, for example, comprise a total dose of up to 1 μg, for example up to 500 ng, for example up to 50 ng, for example less than 20 ng of active agent in a dosing period ranging, for example, between 1 and 14 days. For example, a total dose of less than 18 ng, 17 ng, 16 ng, 15 ng, 14 ng, 13 ng, 12 ng, 11 ng or 10 ng may be administered.

The compound of Formula (I) or a pharmaceutically acceptable salt, solvate, hydrate or prodrug thereof may be administered in a therapeutically effective amount. A therapeutically effective amount of a compound of Formula (I) for topical administration for treatment of CNV may be at least about 5 μg/10 μl of delivery vehicle. Alternatively, a therapeutically effective amount may be at least about 100 μg/mL, for example at least about 200 μg/mL, at least about 300 μ/mL, at least about 400 μg/mL, at least about 500 μg/mL, at least about 600 μg/mL, at least about 700 μg/mL, at least about 800 μg/mL, at least about 900 μg/mL, or at least about 1000 μg/mL. Alternatively, a therapeutically effective amount may be at least about 1 g/mL, for example at least about 2 mg/mL, at least about 3 mg/mL, at least about 4 mg/mL, at least about 5 mg/mL. Alternatively, a therapeutically effective amount may be less than about 5 mg/mL, for example less than about 4 mg/mL, less than about 3 mg/mL, less than about 2 mg/mL, less than about 1 g/mL. The therapeutically effective amount may be administered daily, for a dosing period ranging, for example, between 1 and 14 days. The therapeutically effective amount may be a total daily dosage which may be divided and administered in portions during the day, for example twice daily.

A therapeutically effective amount of a compound of Formula (I) for anti-angiogenic treatment of a mammalian subject, or for use in treating or preventing microvascular hyperpermeability disorders, or in regulating the pro-angiogenic pro-permeability properties of $VEGF_{xxx}$ isoforms, or in supporting epithelial cell survival without increased permeability, or in reducing the nature (for example the number density and/or size) of fenestrations of epithelial filtration membranes, or for use in treating or preventing neuropathic and neurodegenerative disorders, or for use as a neuroprotective or neuroregenerative agent in vivo or in vitro, or for use in treating or preventing VEGFR2-mediated non-inflammatory pain, or for use in reducing the risk of a female mammal developing pre-eclampsia or a complication linked thereto, or of a fetus of the female mammal developing a fetal or neonatal deficiency linked to maternal pre-eclampsia may be calculated according to body mass of the subject to be treated, and may be at least about 20 mg/kg, for example at least about 30 mg/kg, at least about 40 mg/kg, at least about 50 mg/kg, at least about 60 mg/kg, at least about 70 mg/kg, at least about 80 mg/kg, at least about 90 mg/kg, at least about 100 mg/kg. Alternatively, the therapeutically effective amount may be less than about 100 mg/kg, for example less than about 90 mg/kg, less than about 80 mg/kg, less than about 70 mg/kg, less than about 60 mg/kg, less than about 50 mg/kg, less than about 40 mg/kg, less than about 30 mg/kg, or less than about 20 mg/kg, for example less than about 10 mg/kg, less than about 5 mg/kg.

"Treating or preventing"

The expression "treating or preventing" and analogous terms used herein refers to all forms of healthcare intended to remove or avoid the disorder or to relieve its symptoms, including preventive, curative and palliative care, as judged according to any of the tests available according to the prevailing medical and psychiatric practice. An intervention that aims with reasonable expectation to achieve a particular result but does not always do so is included within the expression "treating or preventing". An intervention that succeeds in slowing or halting progression of a disorder is included within the expression "treating or preventing".

Certain neurological and psychiatric disorders are considered as "spectrum" conditions, in which individuals may exhibit some or all of a range of possible symptoms, or may exhibit only a mild form of the disorder. Furthermore, many neurological and psychiatric conditions are progressive, starting with relatively mildly abnormal symptoms and progressing to more severely abnormal symptoms. The present invention includes the treatment and prevention of all neurological and psychiatric conditions of whatever type and stage.

"Susceptible to"

The expression "susceptible to" and analogous terms used herein refers particularly to individuals at a higher than normal risk of developing a medical or psychiatric disorder, or a personality change, as assessed using the known risk factors for the individual or disorder. Such individuals may, for example, be categorised as having a substantial risk of developing one or more particular disorders or personality changes, to the extent that medication would be prescribed and/or special dietary, lifestyle or similar recommendations would be made to that individual.

"Non-therapeutic method"

The expression "non-therapeutic method" used herein refers particularly to an intervention performed on an individual who is neurologically or psychologically within the normal range, to normalise or enhance or improve a function of the neurological or psychological kind. A neurological function that may suitably be treated non-therapeutically may include, for example, cognition (including thanking, reasoning, memory, recall, imagining and learning), concentration and attention, particularly towards the milder end of the scale of conditions, and mild abnormal behavioural or personality traits. A psychological function that may suitably be treated non-therapeutically may include, for example, human behaviour, mood, personality and social function, for example grief, anxiety, depression, moodiness, moroseness, teenage moods, disrupted sleep patterns, vivid dreaming, nightmares, and sleepwalking.

There is a borderline between diagnosable neurological and psychiatric disorders and (non-diagnosable) neurological and psychological functions within the normal range. Therefore, in addition to the examples of neurological and psychological functions give above that are treatable according to the non-therapeutic methods of the present invention, mild forms of neurological and psychiatric disorders, that are non-diagnosable because the associated behaviours or thoughts do not cause significant distress to the individual or are not disruptive of his or her everyday functioning, are also to be considered as conditions treatable non-therapeutically according to the present invention.

"Normalise"

The expression "normalise" and analogous terms used herein refers particularly to a physiological adjustment towards a condition characteristic of general normal neurological or psychiatric health, whether or not a condition is actually reached that would be characterised as normal.

Mammals

Besides being useful for human treatment, the present invention is also useful in a range of mammals. Such mammals include non-human primates (e.g. apes, monkeys and lemurs), for example in zoos, companion animals such as cats or dogs, working and sporting animals such as dogs, horses and ponies, farm animals, for example pigs, sheep, goats, deer, oxen and cattle, and laboratory animals such as rodents (e.g. rabbits, rats, mice, hamsters, gerbils or guinea pigs).

Where the disorder or function to be treated is exclusive to humans, then it will be understood that the mammal to be treated is a human. The same applies respectively to any other mammalian species if the disorder or function to be treated is exclusive to that species.

BRIEF DESCRIPTION OF THE DRAWINGS

Embodiments of the present invention will now be described, purely by way of example, and with reference to the accompanying drawings, in which:

FIGS. 14D-G show data for the compounds, where (D) shows concentration of compounds in sclera tissue after 24 hrs as a percentage of applied concentration in porcine eye tissue; (B) shows concentration of compounds in RPE/choroid tissue after 24 hrs as a percentage of applied concentration in porcine eye tissue; (F) shows concentration of compounds in retinal tissue after 24 hrs as a percentage of applied concentration in porcine eye tissue; and (G) shows concentration of compounds in the lower chamber ("vitreous") after 24 hrs as a percentage of applied concentration in porcine eye tissue;

FIG. 19 shows that neither SPHINX31 nor its metabolite SPHINX46 induce genotoxicity in an Ames test;

FIGS. 20A-D show Ganzfeld ERG recordings in mice taken 24 h after treatment with control or SPHINX31 at 2 μg/mL by topical eye drop administration, following stimulation with increasing intensities of (A) green light; (B) UV light; (C) green light; (D) UV light;

FIGS. 20E-F show ERG recordings in mice after treatment with control or SPHINX31 at 2 μg/ml by topical eye drop administration, following stimulation with increasing intensities of (E) green light; (F) UV light;

FIGS. 20G-J show ERG recordings in mice after treatment with control or SPHINX31 at 2 μg/ml by topical eye drop administration, following stimulation with increasing intensities of (G) green light; (H) UV light; and (I) extraction efficiency in the retina; and (J) extraction efficiency in the choroid;

METHODS

Synthetic Protocol

Figure 1:
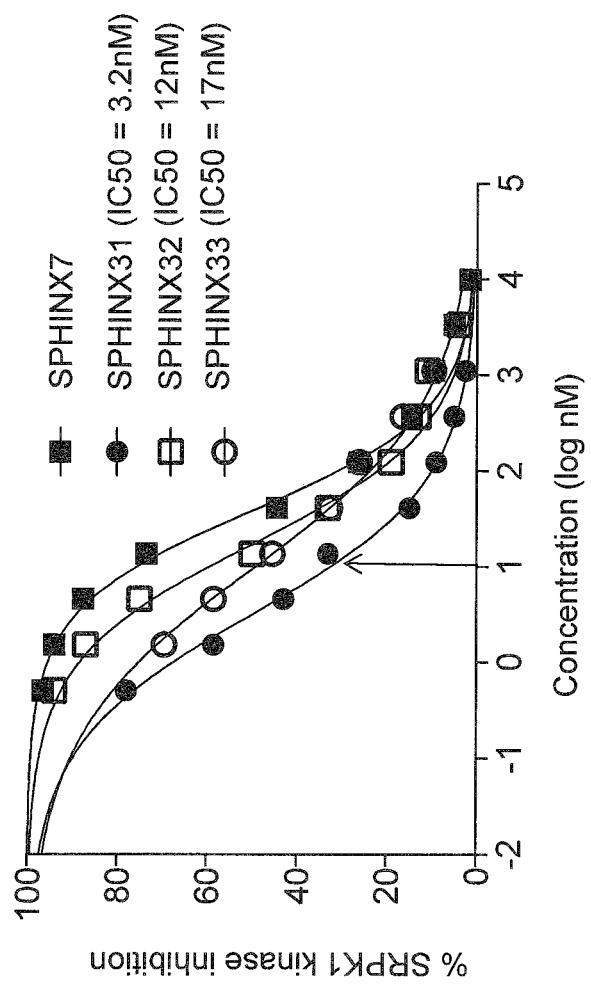
FIG. 1 shows the activity of compounds 12 to 14 (termed SPHINX31, SPHINX32 and SPHINX33 respectively) of Formula (I) against SRPK1.

The general synthetic protocol for compounds is shown in Scheme 1 below, with an exemplary synthesis for compound 12, also referred to herein as SPHINX31, shown in Scheme 2 below. These compounds can be synthesized in a variety of ways, but this is the shortest and most efficient. Variations of this protocol to synthesize other compounds described herein are within the wherewithal of the skilled person.

Scheme 1: General Synthesis
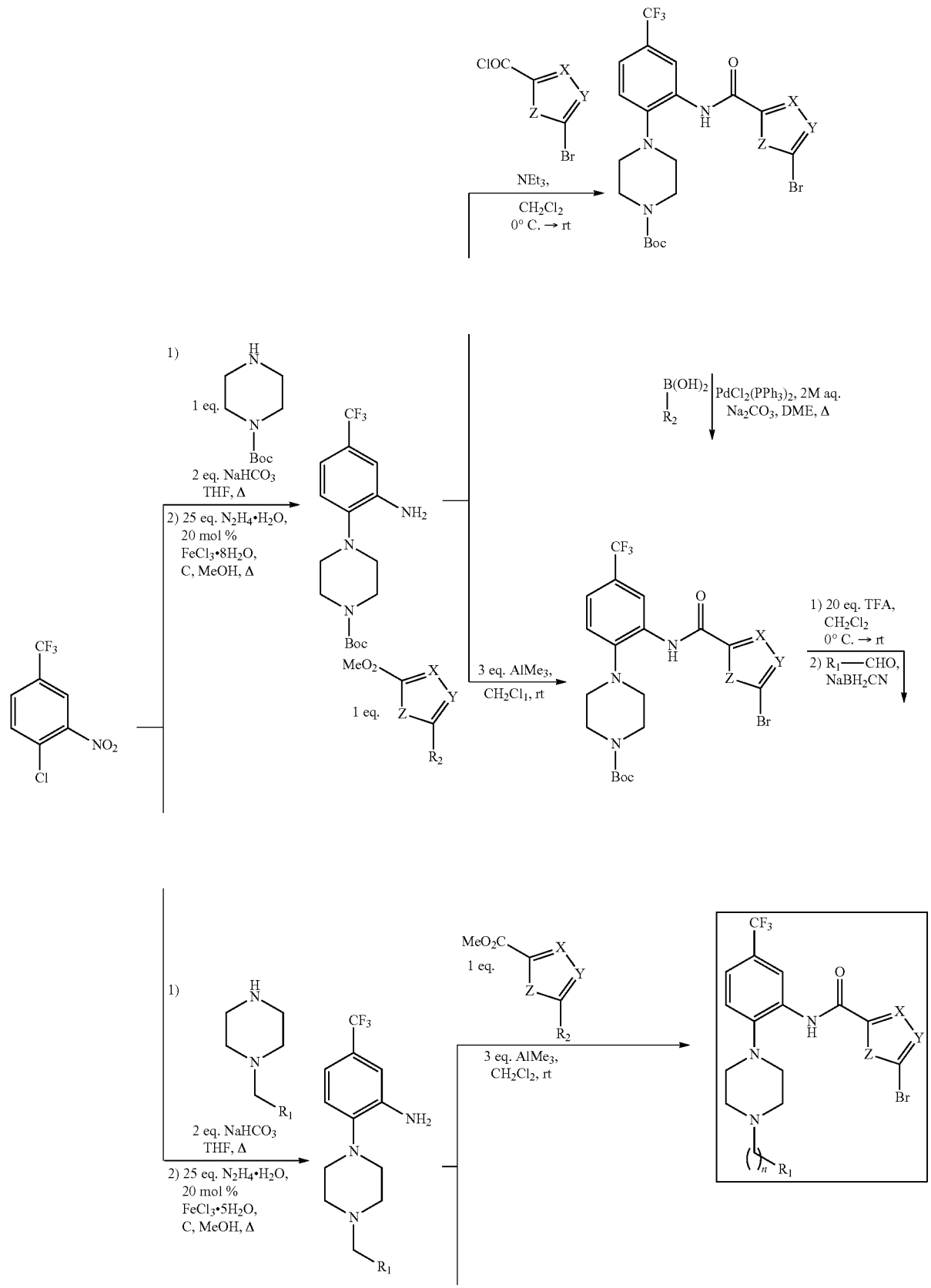

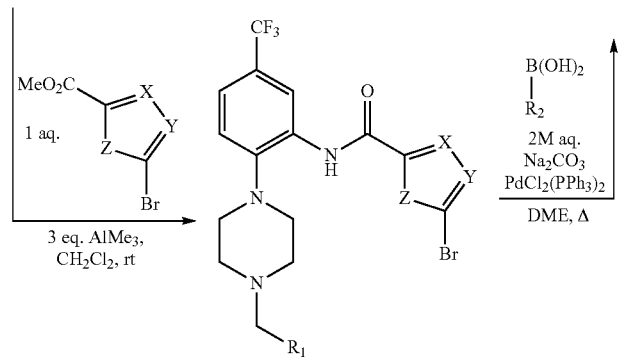
Scheme 2: Synthetic route to compound 12 (SPHINX31)
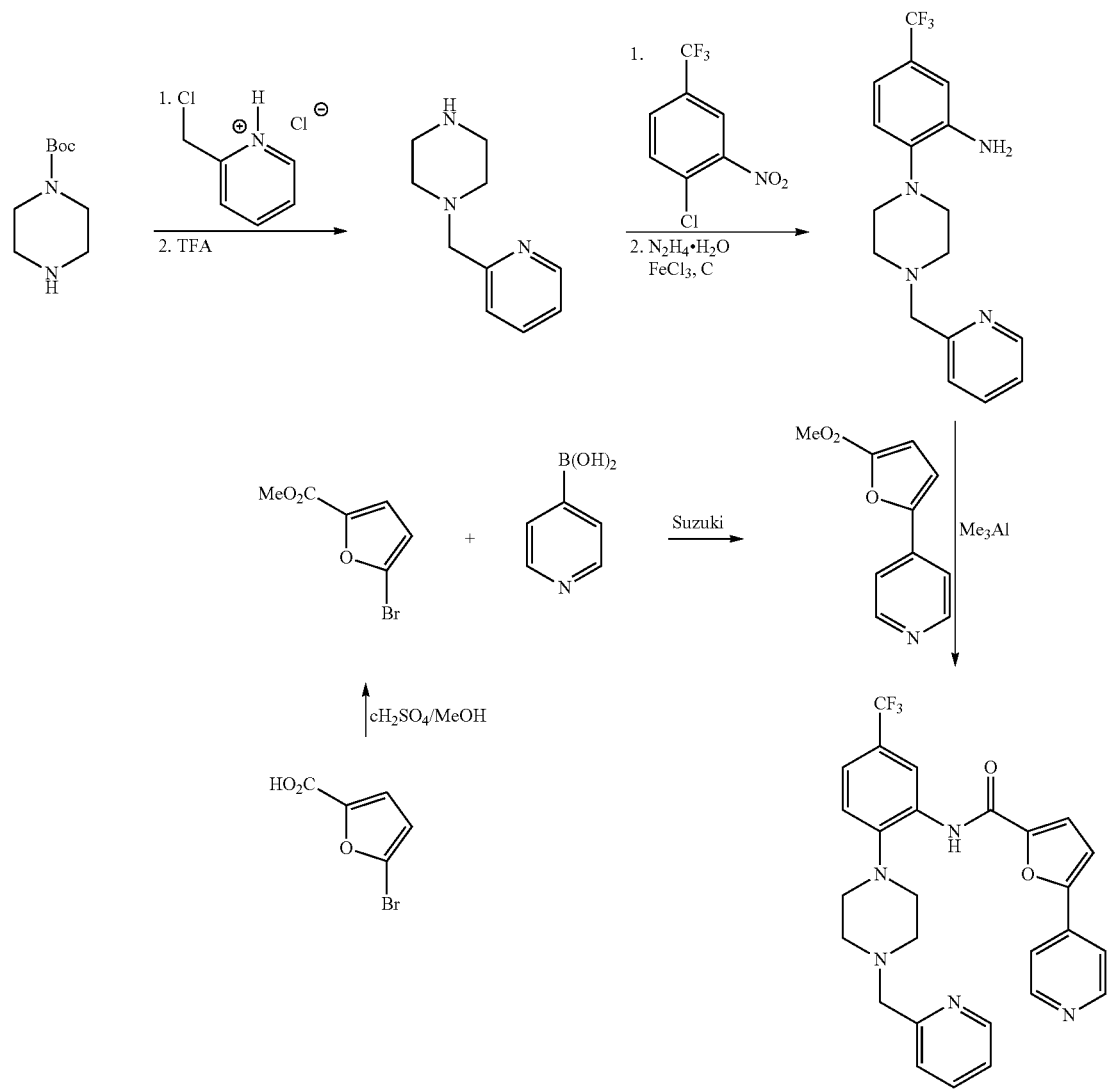
SPHINX31

SPHINX31 Experimental t-Butyl 4-(pyridin-2-ylmethyl)piperazine-1-carboxylate (3)

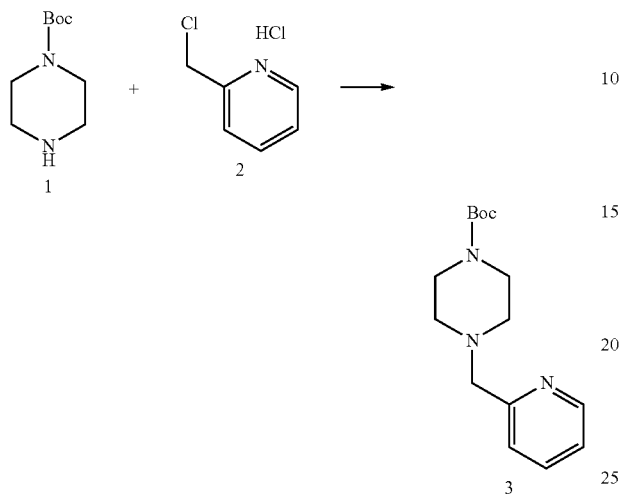

2-(Chloromethyl)pyridine hydrochloride (2) (1.97 g, 10.58 mmol) was added as a solid in one portion to a suspension of 1-Bocpiperazine (1) (2.24 g, 13.67 mmol) and potassium carbonate (4.98 g, 36.02 mmol) in anhydrous DMF (12 mL) at room temperature. The suspension was stirred at room temperature for 16 hours then poured onto saturated aqueous sodium bicarbonate solution. The mixture was extracted with ethyl acetate (×3). The organic extracts were combined and washed with water and brine, then dried (Na$_2$SO$_4$). The solvent was removed under reduced pressure and the crude product purified by flash chromatography on deactivated silica gel, eluting with 60% ethyl acetate/n-hexane, to afford the product (3) as a colourless gum (2.98 g, 98%), with all analytical material matching that reported in the literature (E. Carceller, M. Merlos, M. Giral, C. Almansa, J. Bartroli, J. Garcia-Rafanell J. Forn; *J. Med. Chem.*, 1993, 36, 2984-2997). $^1$H NMR (300 MHz; CDCl$_3$) δ 1.44 (s, 9H), 2.42-2.45 (m, 4H), 3.43-3.46 (m, 4H), 3.65 (s, 2H), 7.14-7.18 (m, 1H), 7.38 (d, J=7.8 Hz, 1H), 7.61-7.67 (m, 1H), 8.55-8.57 (m, 1H).

1-(Pyridin-2-ylmethyl)piperazine (4)

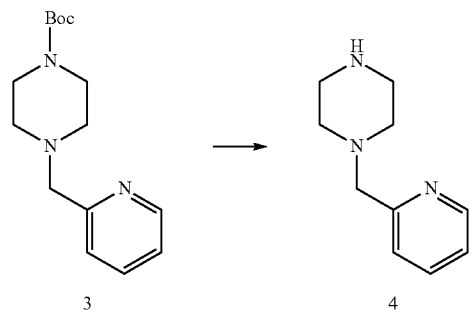 [SMILES: CC(C)(C)OC(=O)N1CCN(Cc2ccccn2)CC1 ; c1ccc(CN2CCNCC2)nc1]

Trifluoroacetic acid (21.5 mL, 280.96 mmol) was added dropwise to a solution of Boc-piperazine (3) (2.98 g, 10.76 mmol) in dichloromethane (21.5 mL) at 0° C. (ice). The solution was stirred at 0° C. for 10 min then the cold bath was removed and the solution was stirred at room temperature for 4 hours. The solution was neutralised to pH 9 using saturated aqueous sodium bicarbonate solution. The dichloromethane layer was removed and the remaining aqueous solution was extracted with dichloromethane (×2). The organic extracts were combined and washed with saturated aqueous sodium bicarbonate solution, water and brine, then dried (Na$_2$SO$_4$). The solvent was removed under reduced pressure to afford the product (4) as a light yellow oil (1.91 g, 99%), which was of sufficient purity to use in the next step, with all analytical data matching that reported in the literature (E. Carceller, M. Merlos, M. Giral, C. Almansa, J. Bartroli, J. Garcia- Rafanell, J. Forn *J. Med. Chem.*, 1993, 36, 2984-2997). $^1$H NMR (300 MHz; CDCl$_3$) δ 1.95 (s, 1H), 2.44-2.47 (m, 4H), 2.88-2.91 (m, 4H), 3.62 (s, 2H), 7.13 (dd, 7.6 and 1.2 Hz, 1H), 7.38 (d, J=7.8 Hz, 1H), 7.59-7.65 (m, 1H), 8.52-8.55 (m, 1H).

1-(2-Nitro-4-(trifluoromethyl)phenyl)-4-(pyridin-2-ylmethyl)piperazine (5)

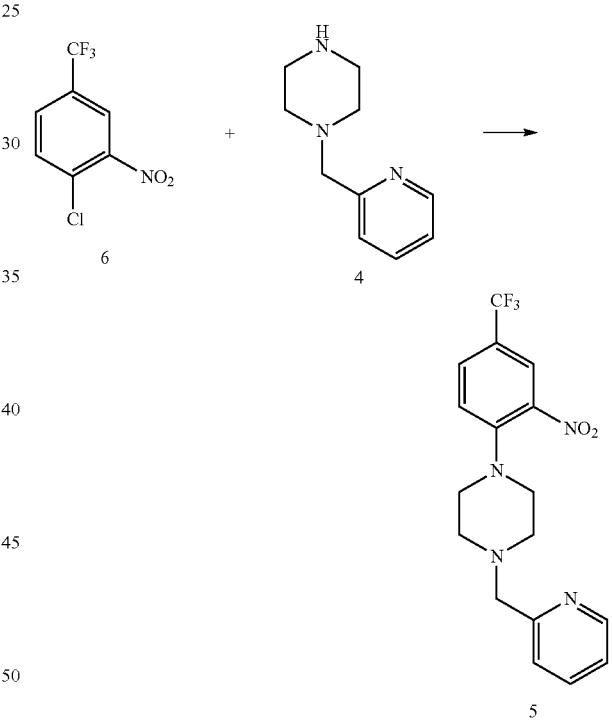

A solution of piperazine (4) (7.01 g, 39.56 mmol), 4-chloro-3-nitrobenzotrifluoride (6) (6.1 mL, 41.51 mmol) and solid sodium bicarbonate (8.31 g, 98.91 mmo) in anhydrous THF (39.5 mL) was heated reflux for 16 hours. The solution was allowed to cool to room temperature and the reaction solution was filtered through a short pad of Celite, eluting with ethyl acetate. The solvent was removed under reduced pressure to afford the product (5) as an orange gum (10.72 g, 74%), which was of sufficient purity to use in the next step. On occasion when the crude product was impure it could be purified by flash chromatography on deactivated silica gel, eluting with 2% methanol/ethyl acetate to afford the product. $^1$H NMR (500 MHz CDCl$_3$) δ 2.67-2.69 (m, 4H), 320-3.22 (m, 4H), 3.73 (s, 2H), 7.15 (d, J=8.8 Hz, 1H), 7.17-7.20 (m, 1H), 7.39 (d, J=7.8 Hz, 1H), 7.63-7.68 (m, 2H), 8.03 (br s, 1H), 8.59 (d, J=4.8 Hz, 1H); $^{13}$C NMR (75 MHz; CDCl$_3$) δ 50.9, 52.9, 64.5, 120.6, 122.1 (q, $J_{C-F}$=34.7 Hz), 122.4, 123.4 (q, $J_{C-F}$=270.8 Hz), 123.5, 124.3 (q, $J_{C-F}$=3.9 Hz), 130.2 (q, $J_{C-F}$=3.5 Hz), 136.6, 140.6, 148.1, 149.6, 158.0; IR (NaCl, neat) 1625 cm$^{-1}$; HRMS (ESI-MS): m/z calcd for C$_{17}$H$_{17}$F$_3$N$_4$O$_2$Na [M+Na]$^+$ 389.1201, found 389.1185.

2-(4-(Pyridin-2-ylmethyl)piperazin1-yl)-5-(trifluoromethyl)aniline (7)

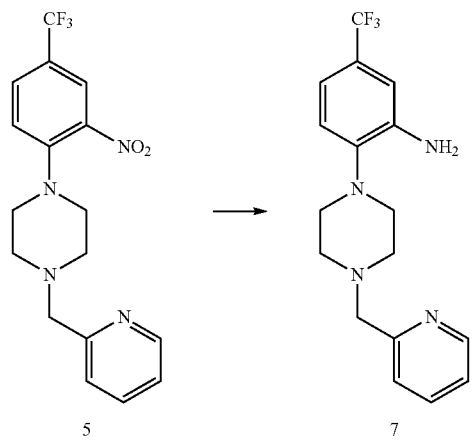 [SMILES: O=[N+]([O-])c1cc(C(F)(F)F)ccc1N1CCN(Cc2ccccn2)CC1 ; Nc1cc(C(F)(F)F)ccc1N1CCN(Cc2ccccn2)CC1]

Hydrazine hydrate (35.5 mL, 731.84 mmol) was added dropwise to a solution of piperazine (5) (10.72 g, 29.25 mmol), iron(III) chloride hexahydrate (1.59 g, 5.87 mmol) and charcoal (1.17 g) in methanol (290 mL) at room temperature. The solution was heated at reflux for 2 hours. The solution was allowed to cool to room temperature then filtered through a short pad of Celite, eluting with ethyl acetate. The solvent was removed under reduced pressure. The residue was diluted with water and extracted with ethyl acetate (×3). The organic extracts were combined and dried (Na$_2$SO$_4$). The solvent was removed under reduced pressure to afford the product 7 as a white solid (9.35 g, 95%), which was of sufficient purity to use in the next step. Mp 126-1.27° C.; $^1$H NMR (300 MHz; CDCl$_3$) δ 2.67-2.69 (m, 4H), 2.97-3.00 (m, 4H), 3.74 (s, 2H), 4.07 (br s, 2H), 6.92-7.04 (m, 3H), 7.16-7.20 (m, 1H), 7.44 (d, J=7.8 Hz, 1H), 7.64-7.70 (m, 1H), 8.57-8.60 (m, 1H); $^{13}$C NMR (75 MHz; CDCl$_3$) δ 50.7, 54.0, 64.8, 111.6 (q, J=3.9 Hz), 115.5 (q, J=4.1 Hz), 119.7, 122.3, 123.4, 124.6 (q, $J_{C-F}$=271.2 Hz), 126.5 (q, $J_{C-F}$=32.2 Hz), 136.6, 141.7, 142.2, 149.5, 158.5; IR (NaCl, neat) 3187, 3283 cm$^{-1}$; HRMS (ESI-MS): m/z calcd for C$_{17}$H$_{20}$F$_3$N$_4$ [M+Na]$^+$ 337.1594.

Methyl 5-bromofuran-2-carboxylate (8)

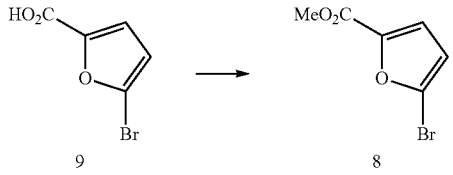 [SMILES: O=C(O)c1ccc(Br)o1 ; COC(=O)c1ccc(Br)o1]

Concentrated sulfuric acid (0.56 mL, 10.51 mmol) was added dropwise to a solution of carboxylic acid (9) (20.0 g, 0.105 mol) in methanol (1050 mL) at room temperature. The solution was heated at reflux for 17 hours. The solution was allowed to cool to room temperature and the methanol was removed under reduced pressure. The residue was diluted with water and the pH of the solution was adjusted to pH 9 using solid sodium bicarbonate. The mixture was extracted with ethyl acetate (×3). The organic extracts were combined and washed with water and brine, then dried (Na$_2$SO$_4$). The solvent was removed under reduced pressure to afford the product 8 as a white solid (19.47 g, 91%), which was of sufficient purity to use in the next step, with all analytical data matching that reported in the literature (Y. Zhu, H. Yan, L. Lu, D. Liu, G. Rong, J. Mao *J. Org. Chem.*, 2013, 78, 9898-9905). Mp 67-68° C.; $^1$H NMR (300 MHz; CDCl$_3$) δ 3.90 (s, 3H), 6.46 (d, J=3.5 Hz, 1H), 7.13 (d, J=3.5 Hz, 1H).

Methyl 5-(pyridin-4-yl)furan-2-carboxylate (10)

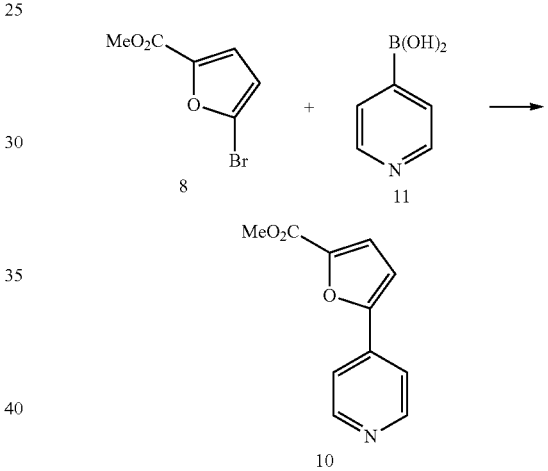

A flask was charged with ester 8 (2.17 g, 10.58 mmol), 4-pyridinylboronic acid (II) (1.00 g, 8.14 mmol), PdCl$_2$(PPh$_3$)$_2$ (0.29 g, 0.41 mmol), 2 M aqueous sodium carbonate solution (10.2 mL, 22.4 mmol) and 1,2-dimethoxyethane (81 mL). The flask was freeze-pump-thawed (×3), backfilled with argon and heated at reflux for 17 hours. The solution was cooled to room temperature and the DME was removed under reduced pressure. The pH of the residue was adjusted to pH 1 using 2 M aqueous hydrochloric acid solution. The solution was extracted with dichloromethane (×3). The dichloromethane extracts were discarded. The remaining aqueous solution was neutralised to pH 9 using solid sodium bicarbonate and extracted with ethyl acetate (×3). The respective organic extracts were combined and washed with water and brine, then dried (Na$_2$SO$_4$). The solvent was removed under reduced pressure to afford the product 10 as a white solid (1.41 g, 85%), which was of sufficient purity to use in the next step, with all analytical data matching that reported in the literature (H. Y. Fu, H. Doucet, *Eur. J. Org. Chem.*, 2011, 7163-7173). Mp 95-97° C.; $^1$H NMR (400 MHz; CDCl$_3$) δ 3.94 (s, 3H), 6.95 (d, J3.6 Hz, 1H), 7.27 (d, J=3.5 Hz, 1H), 7.62-7.64 (m, 2H), 8.66-8.68 (m, 2H).

N-(2-(4-(Pyridin-2-ylmethyl)piperazin-1-yl)-5-trifluoromethyl)phenyl)-5-(pyridin-4-yl)furan-2-carboxamide (SPHINX31) (12)

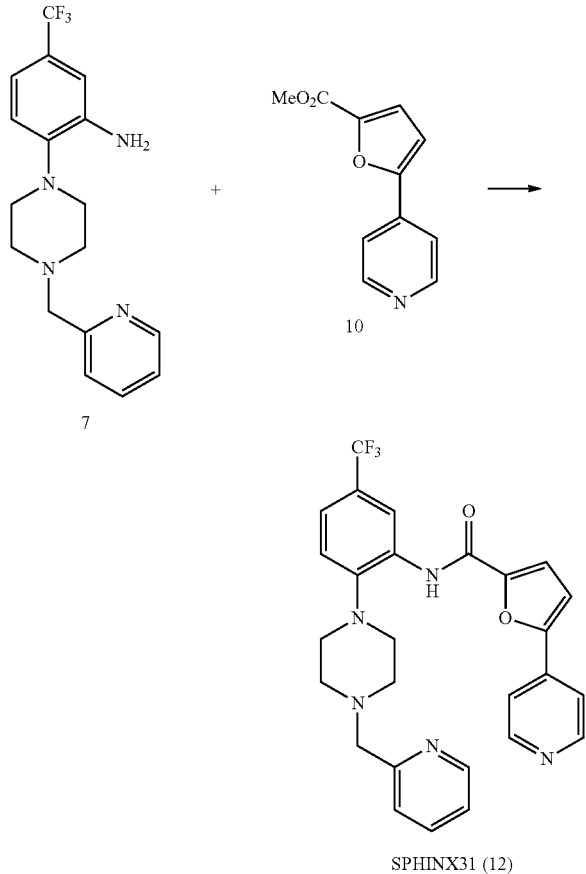

A 2M solution of trimethylaluminium in toluene (0.84 mL, 1.68 mmol) was added dropwise to a solution of aniline 7 (0.189 g, 0.56 mmol) in dichloromethane (1.1 mL) at room temperature. The solution was stirred at room temperature for 1 hour after which, a solution of ester 10 (0.114 g, 0.56 mmol) in dichloromethane (0.6 mL) was added dropwise at room temperature. The reaction solution was stirred at room temperature for an additional 16 hours. To quench the reaction saturated aqueous Rochelle's salt solution was added dropwise at room temperature and the solution allowed to stir at room temperature for a further 15 minutes. The mixture was diluted with saturated aqueous sodium bicarbonate solution and extracted with dichloromethane (×3). The organic extracts were combined and washed with water and brine, then dried ($Na_2SO_4$). The solvent was removed under reduced pressure to afford the product as a white solid (0.19 g, 67%), which was of sufficient purity to use in the next step. On occasion when the crude product was impure it could be purified by flash chromatography on deactivated silica gel, eluting with 5% methanol/ethyl acetate to afford the product. Mp 157-159° C.; $^1$H NMR (300 MHz, $CDCl_3$) δ 2.85 (br, s, 4H), 3.04 (br s, 4H), 3.78 (s, 2H), 7.06 (d, J=3.7 Hz, 1H), 7.20 (m, 1H), 7.31-7.41 (m, 4H), 7.65-7.72 (m, 3H), 8.60 (d, J=4.5 Hz, 1H), 8.80-8.87 (m, 3H), 9.65 (br s, 1H); $^{13}$C NMR (100 MHz, $CDCl_3$) δ 52.2, 54.5, 65.0, 111.3, 116.7 (q, $J_{C-F}$=4.5 Hz), 117.7, 118.5, 121.1, 121.3 (q, $J_{C-F}$=4.5 Hz), 122.5, 123.5, 124.1 (q, $J_{C-F}$=272 Hz), 128.0 (q, $J_{C-F}$=34 Hz), 133.5, 136.7, 148.6, 149.7, 150.8, 153.2, 155.7, 157.9; HRMS (ESI): Calcd for $C_{27}H_{24}F_3N_5O_2$ (MH+) 508.19603, found 508.19315; IR: (neat) 1669, 3332 $cm^{-1}$ Analytical data For all compounds is presented in Table 4.

In Vitro Kinase Assay

Candidate compounds were screened by the Kinase-Glo assay (Promega; Koresawa and Okabe, 2004), the results of which are shown in Table 1 and Table 2. A reaction buffer containing 9.6 mM MOPS pH7 and 0.2 nM EDTA Ph8 was added to 10 μM SRSF1 RS peptide ($NH_2$-RSPSSYGRSRSRSRSRSRSRSRSRSNSRSRSY—OH (SEQ ID NO: 1)) and 0.1 μg of purified SRPK1 kinase. Candidate compounds were serially diluted from 10 μM-0.5 nM and added to the reaction mixture, wells with omitted SRPK1 kinase and omitted compounds were also added as controls. All wells contained one percent DMSO. One micromolar ATP was added, wells minus ATP were used as background controls. The plate was then incubated at 30° C. for 10 minutes. An equal volume of Kinase-Glo (Promega, 25 μl) was added to each well and the plate read for luminescence using an Fluostar Optima (BMG Labtech).

Inhibition of SRSF1 Phosphorylation.

Denys Drash podocytes, also referred to as DDS cells (DDS=Denys Drash Syndrome), with a WTI mutant that fails to repress SRPK1 expression, were treated with increasing concentrations of SPHINX31, or reference compounds SPHINX7 or SPHINX.

Both whole cell lysate (nuclear and cytoplasmic) protein extraction and nuclear protein extracts were used. The extracts were then immunoblotted using either mouse anti-SRPK1 (anti-SRPK1;BD 611072; 1:1000), rabbit anti-pan-VEGF (Santa Cruz A20 sc-152; 1:500), mouse anti-VEG-$F_{xxx}$b (MAB3045; R&D; 1:500), goat anti-SRSF1 (SC10255; 1:500), mouse anti-SRSF1 (AK96) (Santa Cruz SC-33562) or rabbit anti-GAPDH (Sigma G9545, 1:2000). For immunoprecipitation phospho-SRSF1 studies, cell lysates were incubated with mouse anti-SRSF1 (Santa Cruz SC-33562) or anti-Pan-phospho-SR antibody (Santa Cruz, SC-13509) and Protein G Dynabeads (Invitrogen). To detect phosphorylated SRSF1, the eluent was immunoblotted with either anti-SRSF1 or the anti-Pan-phospho-SR antibody (1:500).

PC3 prostate cancer cells were treated with 10 nM EGF in the presence of either DMSO (Vehicle), compound 12 (SPHINX31) or reference compounds at 10 μM for 1 hr. Cells were lysed, and subjected to immunoblotting as described above.

Laser Lesion Induction Protocol

Six to eight week-old C57/B6 mice (B & K Laboratories) and adult Norway-Brown rats (Harlan Laboratories) were anaesthetized with an intraperitoneal injection of a mixture of 50 mg/kg ketamine and 0.5 mg/kg medetomidine. The pupils were dilated with 2.5% phenylephrine hydrochloride and 1% tropicamide. Four photocoagulation lesions were delivered with a krypton red laser (Mice: 250 mW, 0.01 s, 75 μm, Rats: 200 mW, 0.01 s, 75 μm, IRIS Medical 810 nm Oculight Six laser) between the retinal vessels in a peripapillary distribution at a distance of 1-2 disc-diameters in each eye. Only laser lesions with a subretinal bubble at the time of treatment were included in the study. Immediately following laser photocoagulation the animals either received intravitreal injections in both eyes (day 0 and day 7), or given topical eye drops twice daily of reference compounds SRPIN340, SPHINX7 or SPHINX31 in one eye and control vehicle in the other eye. Animals were culled on either day 4 or day 14 and eyes were either unfixed for retinal dissection and protein extraction, or fixed and enucleated and choroids stained for isolectin-B4 and examined, or imaged by fluorescein angiography.

During topical administration tests compounds were made up into a gel based drug delivery vehicle to aid duration of drug exposure to the eye (Doukas et al., 2008), 0.05% DMSO was used to dissolve the compound before it was added to control vehicle.

hERG Inhibition

Compounds were tested for inhibition of the human ether a go-go related gene (hERG) $K^+$ channel using IonWorks patch clamp electrophysiology. 8-Point concentration-response curves were generated using 3-fold serial dilutions (Essen Biosciences).

Differential Scanning fluorimetry was performed as described in Federov et al (2011).

Isoform specific ELISA was performed as described in Varey et al (2008) and Carter et al (2014).

Scleral permeability was measured using a modified Ussing chamber assembly in isotonic assay buffer (pH 7.4). Rabbit or porcine excised eye tissues were mounted in the chambers such that the episcleral side faced the donor chamber and the retinal side faced the receiver chamber. The chambers were filled with equal volumes of assay buffer, with (donor side) or without (receiver side) 1 µg/ml compound. After 4 or 24 hours tissue was removed from the chamber and the receiver side ("vitreous") sampled. Tissue was dissected into sclera, choroid/RPE, and retina and homogenised. A tracer (SPHINX7) was added, and tissue extracted by acetonitrile extraction as described in Gammons et al (2013), Compounds were then analysed by mass spectrometry as described in Gammons et al (2013).

Rabbit Pharmacokinetic Study

Rabbits were treated thrice daily for six days, with 50 µg SPHINX31 in one eye and 50 µg pazopanib as 200 µl eye drops. Rabbits were killed 12 hours after the last eye drop, blood and liver taken, and the retina dissected from the choroid/sclera, incisions male, and laid out flat, and photographs taken. Both eye compartments were dissected into 17 different areas. All samples were weighted. Compound was extracted by reverse phase extraction from the retina and choroid/sclera samples and the liver and plasma as above, and amount determined by mass spectrometry in different areas of the eye, in the blood and in the liver. Amounts per gram of tissue were calculated for SPHINX31 and pazopanib for each sample, and averaged.

Mouse Electroretinography Toxicity Test.

Mice were treated for six days with 2 µg per eye SPHINX31 as eye drops, and ERG carried out using a Micron IV Ganzfield ERG system as recommended by the manufacturers instructions.

Melanin Binding Assay

10 µg/ml SPHINX31 or pazopanib were incubated in 10 µg/ml melanin for 1hr at 37° C. Solutions were then spun at 15 kg for 15 mins and supernatant collected and compounds extracted in acetonitrile. They were then subjected to mass spectometry for quantitation.

Results

Identification of Novel SRPK1 Inhibitors

To identify novel SRPK1 inhibitors, a range of inhibitors were screened in an in vitro kinase assay (Promega; Koresawa and Okabe, 2004). The previously identified SRPK inhibitors SPHINX and SPHINX7 were used as positive controls for the identification of novel candidates. Kinase assays showed that compounds 12 to 14 in Table 1 (termed SPHINX31-33 respectively) had a 10-20 fold increase in potency compared with the previously reported compounds, resulting in $IC_{50}$ values of 3.2-17 nM (FIG. 1).

Figure 6:
FIG. 6 shows the TREEspot™ results of a kinome screen of SPHINX31 against all known kinases using the DiscoverX KINOMEscan® binding affinity assay.
Figure 7:
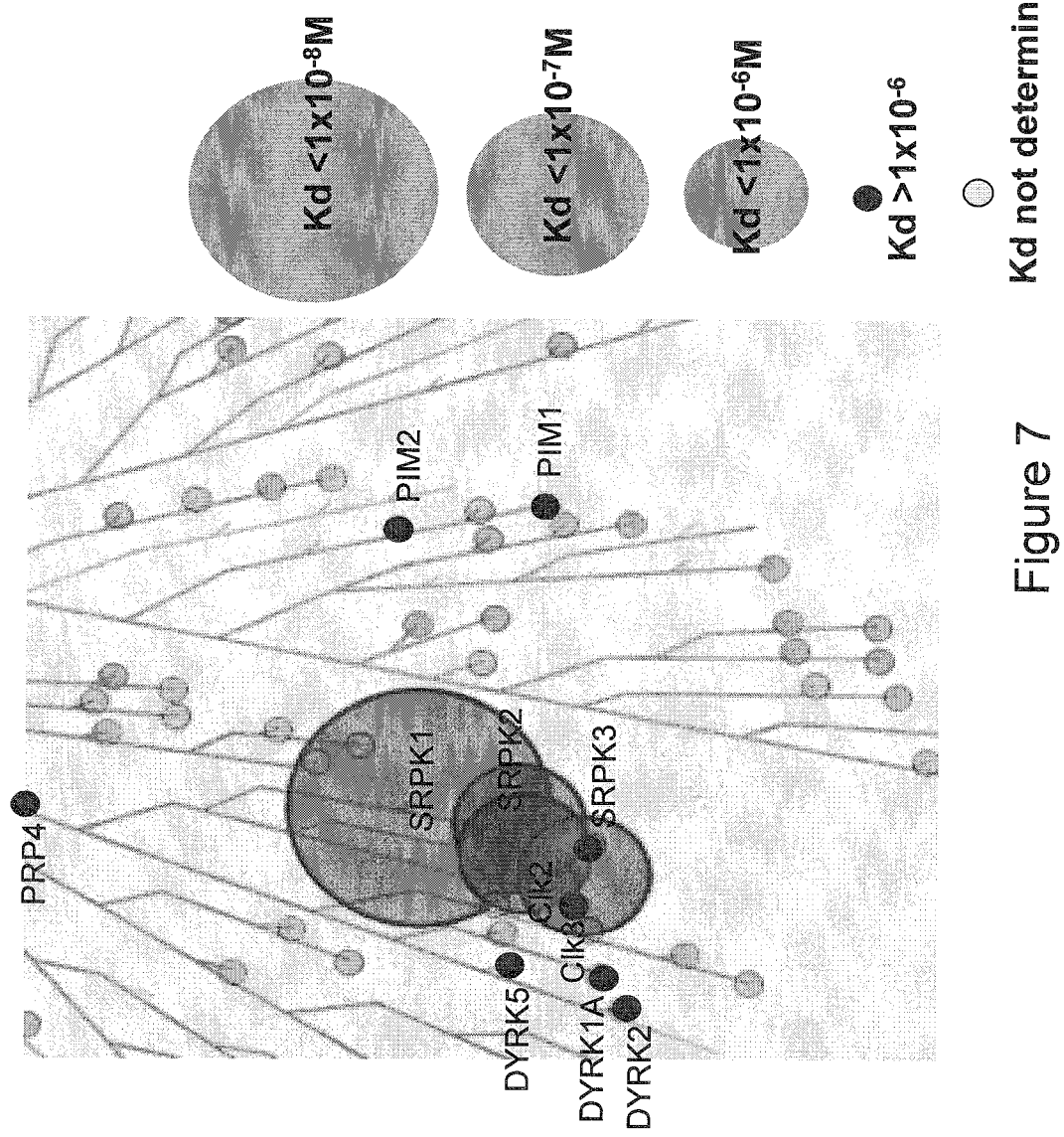
FIG. 7 shows the equivalent binding affinity calculated using differential scanning fluorimetry.
Figure 8:
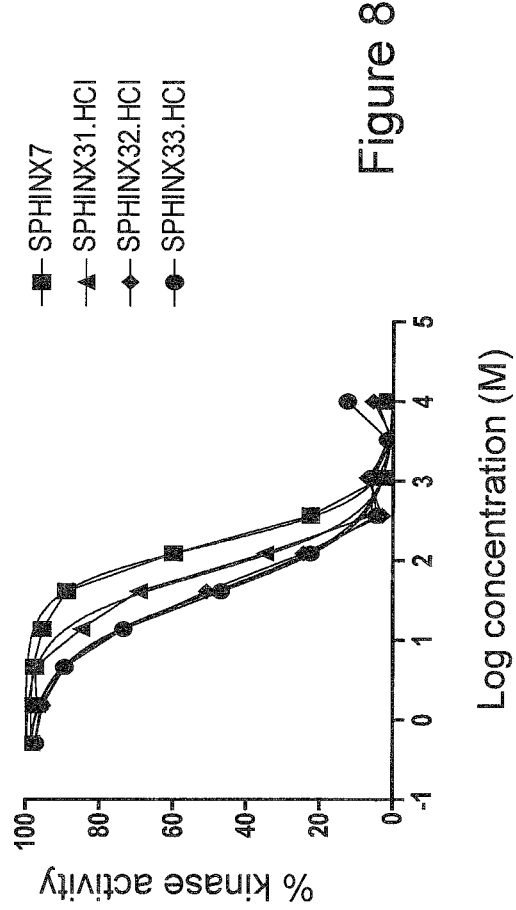
FIG. 8 shows that HCl salts of compounds of the invention salts dose-dependently inhibit SRPK1 activity in vitro and as efficiently as unconjugated SPHINX compounds.

A structure activity relationship study to identify the mechanism and potential for new compounds was undertaken, with new compounds generated with structures shown in Table 2. Additional activity was reached with these compounds down to sub nM potencies for compound 61. A kinome screen of SPHINX31 against all known kinases using substrate DiscoverX binding affinity assay demonstrated that the only other kineses that showed binding were the closely related Clk1 and Clk4, which showed 27% and 14% binding at 1 µM (FIG. 6). Using differential scanning fluorimetry, we determined that SPHINX31 had a binding affinity 44× greater for SRPK1 ($\Delta$Tm 12.8° C.) than SRPK2 (($\Delta$Tm 6.7° C.) or Clk1 ($\Delta$Tm 6.7° C.) and 88 fold greater than Clk4 ($\Delta$Tm 5.7° C.). Binding activity to Clk2, Clk3, PIM1, PIM2, DYRK1, DYRK2, PRPF4B and SRPK3 was negligible ($\Delta$Tm<3° C.) (FIG. 7). The salt forms of the compounds (SPHINX31, 32 and 33) were also potent inhibitors, and were more freely soluble in water (FIG. 8).

Figure 2:
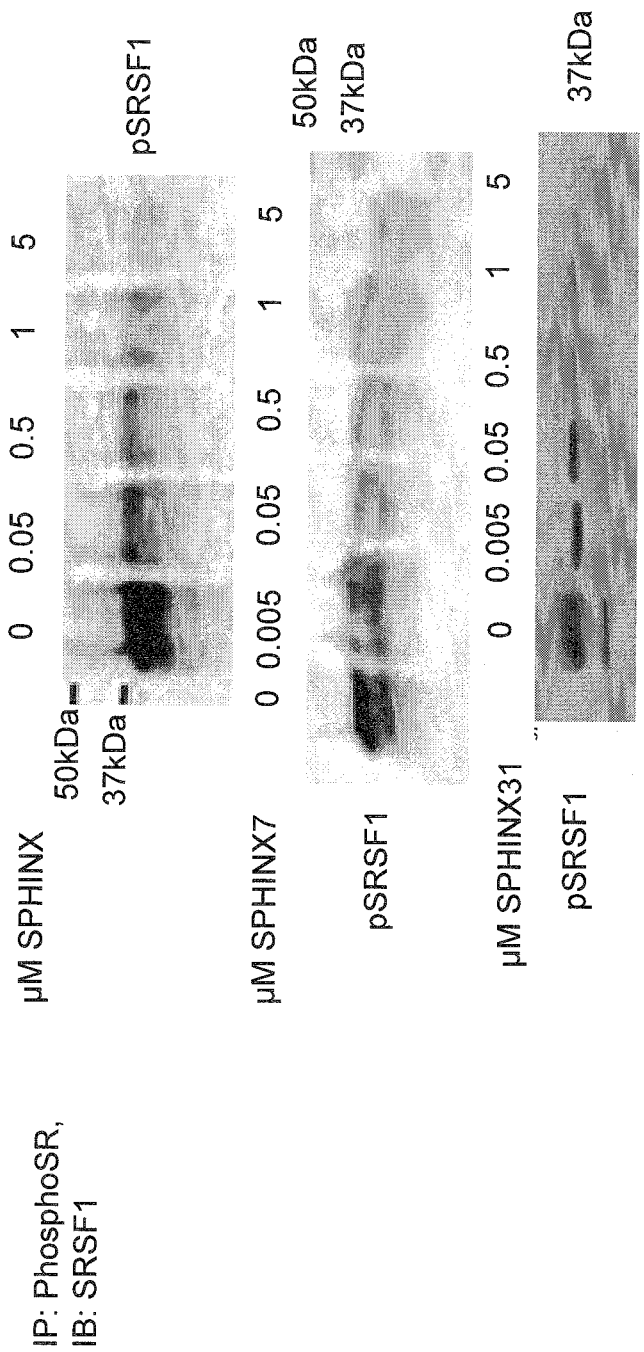
FIG. 2 shows the effects of SPHINX31 relative to reference compounds SPHINX and SPHINX7 on SRSF1 phosphorylation in SRPK1 de-repressed (DDS) cells.
Figure 3:
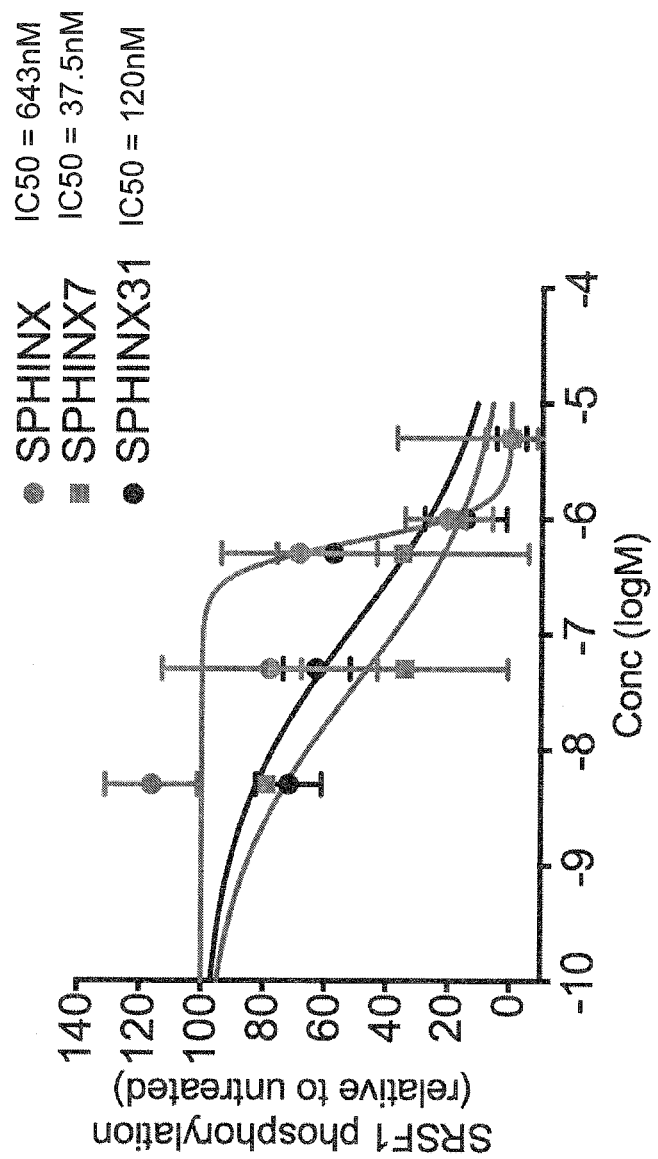
FIG. 3 shows the dose response curve for SPHINX31 relative to reference compounds SPHINX and SPHINX7 in DDS cells.

To determine whether these compounds could inhibit SRPK1 activity in cells, Denys Drash podocytes with constitutively active SRPK1 (caused by a mutation in the SRPK1 repressor, WT1) were treated with increasing concentration of compound 12, termed SPHINX31. FIG. 2 shows that increasing amounts of SPHINX31 increase inhibition of SRSF1 phosphorylation, and FIG. 3 shows that SRSF1 phosphorylation was dose dependently inhibited by treatment with SPHINX31.

Figure 9:
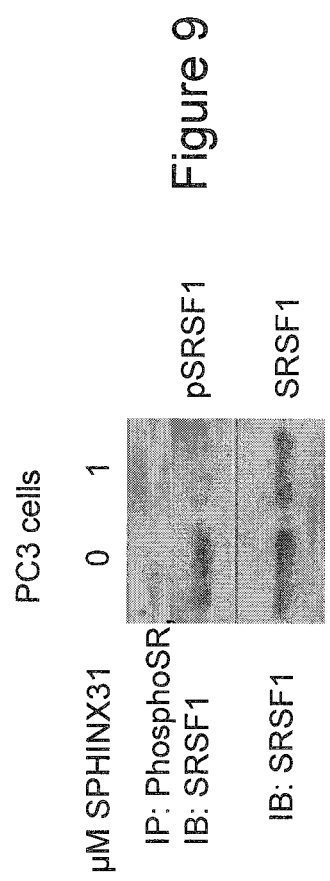
FIG. 9 shows that SPHINX31 also inhibits SRSF1 phosphorylation in PC-3 cells (at 1 μM SPHINX31)
Figure 10A:
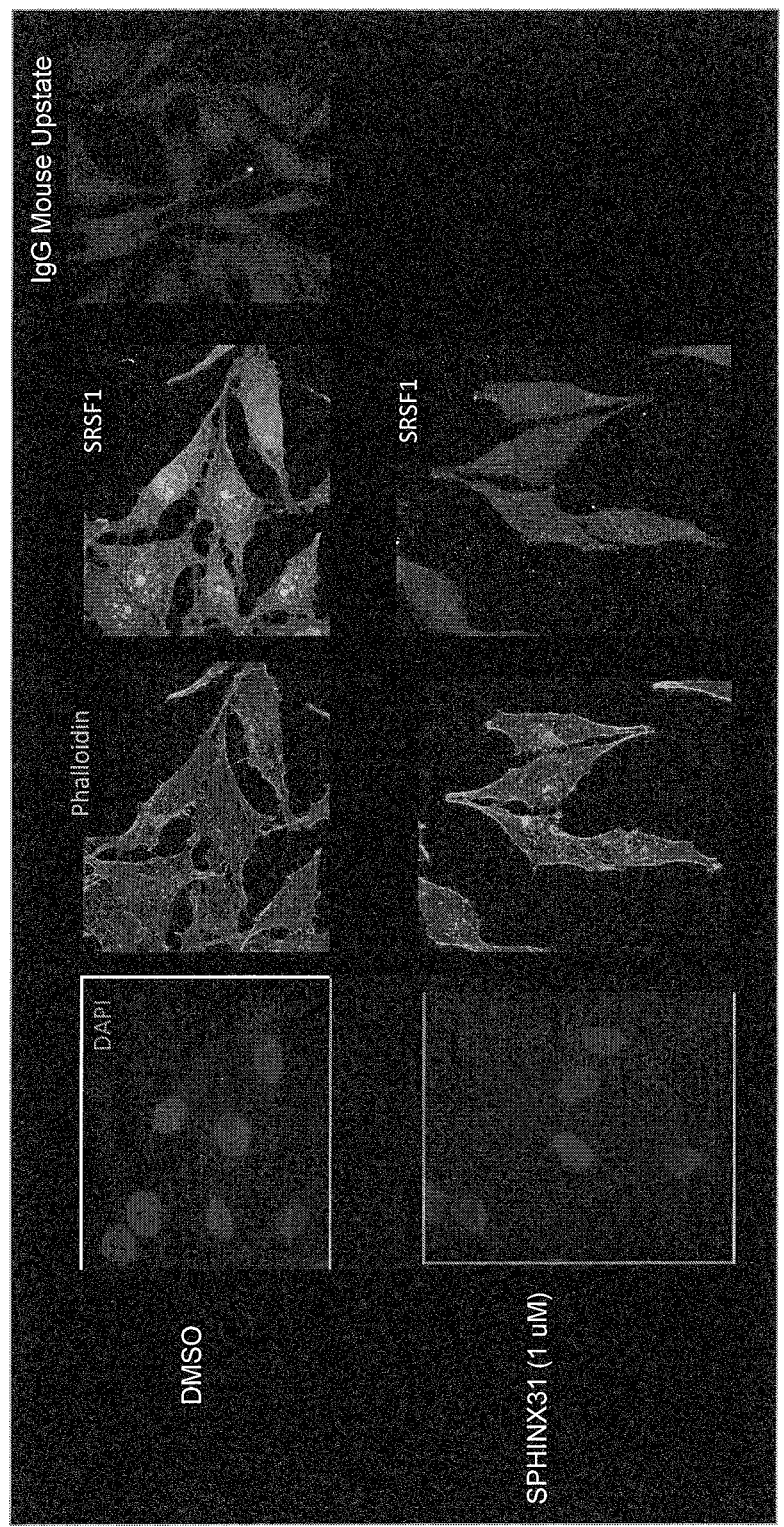
FIGS. 10a shows that SPHINX31 blocks nuclear localisation of SRSF1 in PC-3 cancer cells.
Figure 10B:
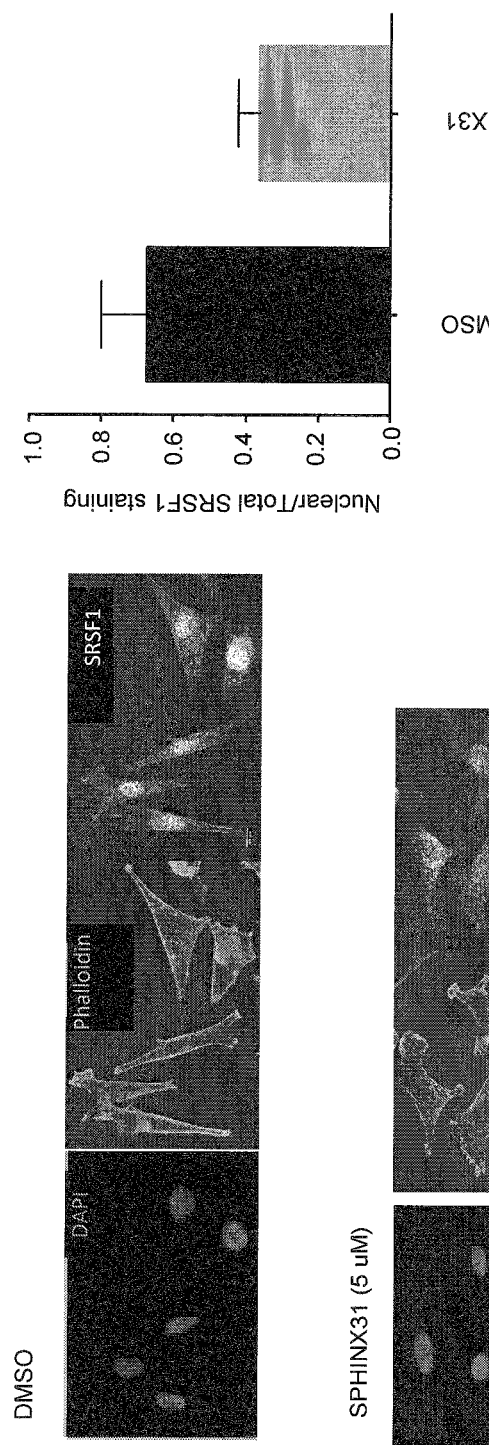
FIG. 10b shows that SPHINX31 blocks nuclear localisation of SRSF1 in MDA-MB-231 cancer cells.

This was repeated in prostate cancer cells (PC3), previously shown to be sensitive to SRPK1 inhibition and again SRSF1 phosphorylation was inhibited (FIG. 9). The effect on SRSF1 localisation (known to be a result of SRPK1 phosphorylation) was also measured by immunofluorescence in PC3 prostate cancer cells and MDA-MB231 (FIGS. 10a (PC3 cells) and 10b MDA-MB231)), SPHINX31 treatment inhibited cellular localisation in both cell types.

Figure 11:
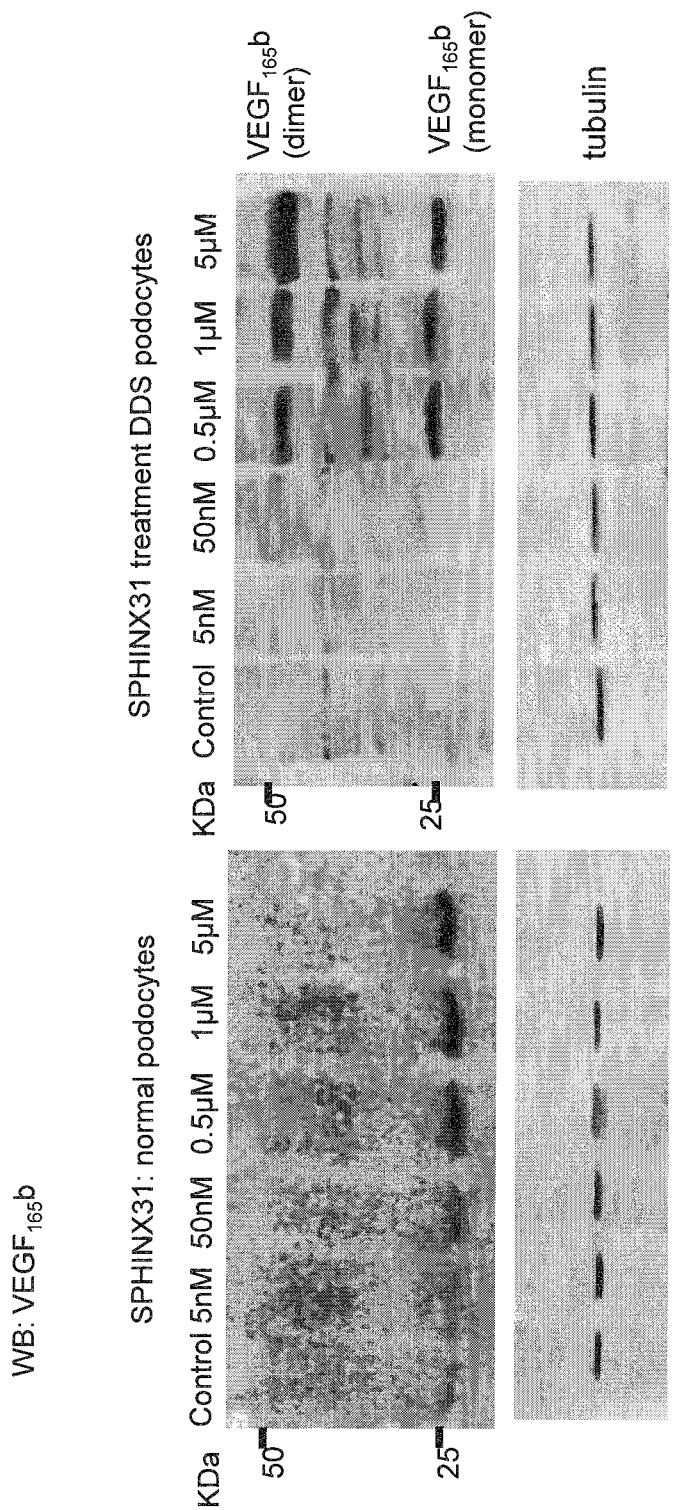
FIG. 11 shows that SPHINX compounds dose dependently increase expression of anti-angiogenic VEGF$_{165}$b in Denys Drash (DDS) podocytes and normal podocytes.
Figure 12:
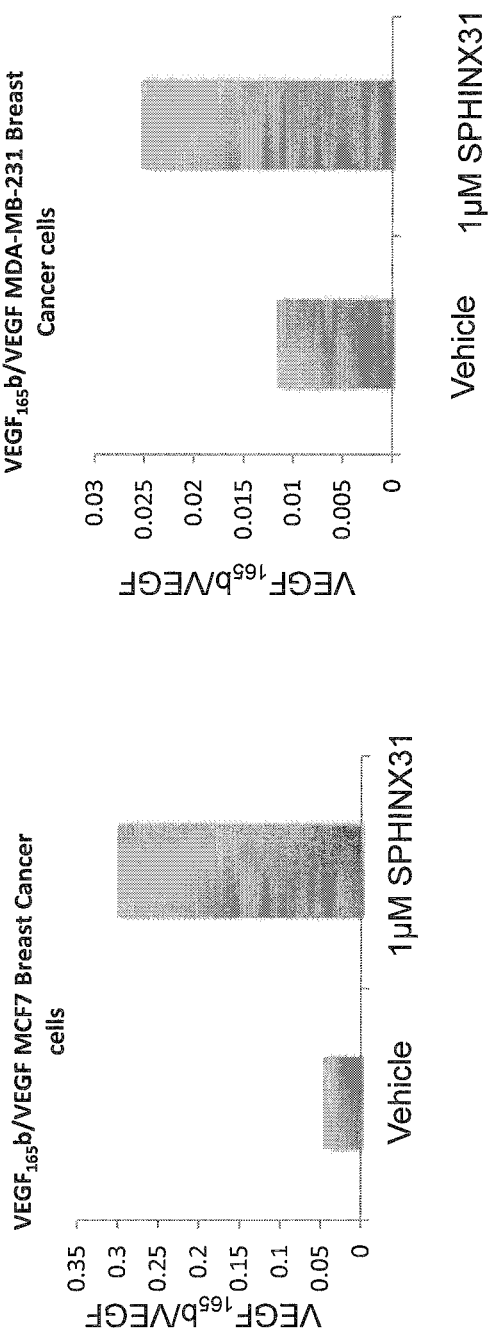
FIG. 12 shows that SPHINX compounds increase expression of anti-angiogenic VEGF$_{165}$b in MCF7 breast cancer cells (left hand chart) and MDA-MB-231 breast cancer cells (right hand chart)
Figure 13:
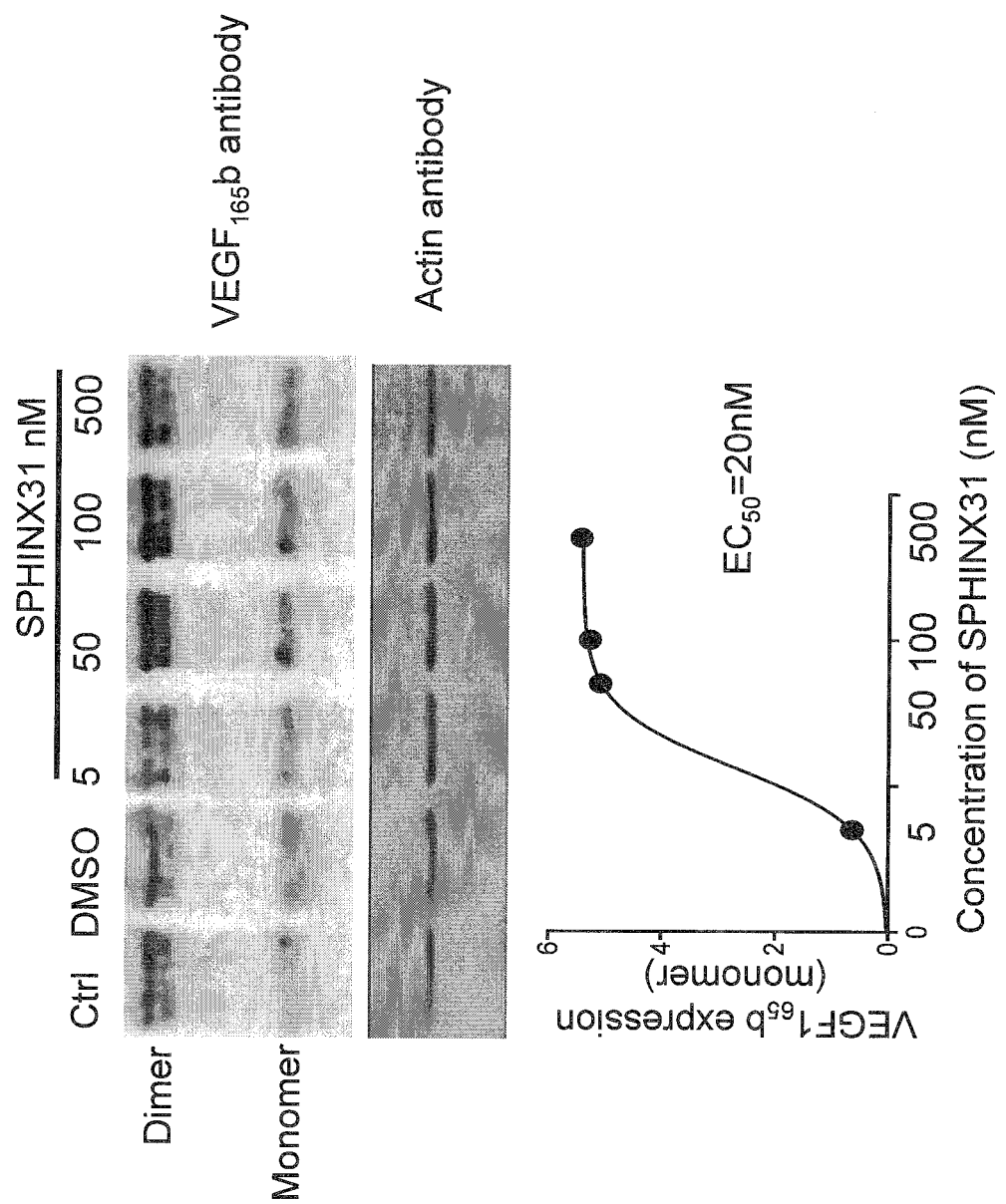
FIG. 13 shows that SPHINX compounds dose dependently increase expression of anti-angiogenic VEGF$_{165}$b RPE cells.

The effect on downstream splicing activity was also investigated, with the data showing that the compounds dose dependently switched splicing from VEGF-$A_{165}$a to VEGF-$A_{165}$b in Denys Drash podocytes and normal podocytes (FIG. 11). Using, isoform specific ELISA, this was also shown to be the case in breast cancer cells (MCF7 and MDA-MB231) cells (FIG. 12). In RPE cells (FIG. 13a) which have been shown to be the primary source of VEGF in angiogenic eye disease), SPHINX31 showed a dose dependent increase in VEGF$_{165}$b with an $EC_{50}$ of 20 nM (FIG. 13).

Figure 14:
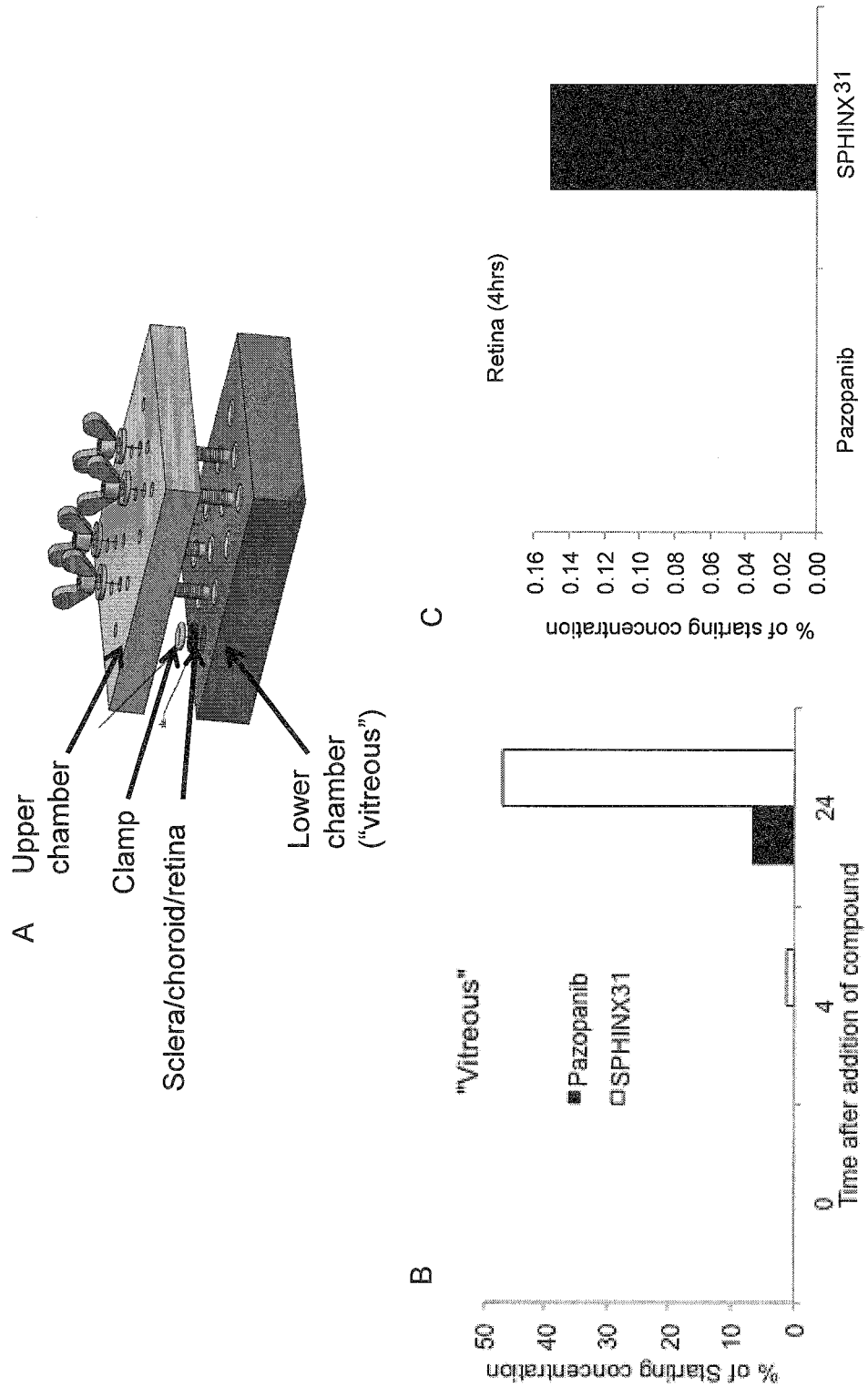
FIG. 14 shows the results of testing compounds of the invention, where (A) shows a permeability chamber used to test whether compounds of the invention can penetrate through the sclera. Pazaponib was used as a control; (B) shows the concentration of compounds in the lower chamber ("vitreous") after 0, 4 or 24 hours in rabbit eye tissue; and (C) shows retinal concentration after 4 hrs as a percentage of applied concentration in rabbit eye tissue.

To determine whether SPHINX31 could get across the sclera of a larger animal, rabbit sclera was clamped between two chambers and SPHINX31 or pazopanib (a VEGFR2 TKI) were added to the sclera with saline added to the bottom chamber and compounds added to the top chamber. After 0, 4 or 24 hours, the fluid from the bottom chamber (vitreous) and the retinal tissue was isolated and compounds purified by acetonitrile extraction and HPLC. FIG. 14 shows that SPHINX31 could be detected at significant concentrations in both retina and vitreous at 4 hrs, whereas pazopanib could not. At 24 hours both were detected in the vitreous, but more SPHINX31 than pazopanib. We also determined whether SPHINX31 could cross porcine eyes. While pazopanib accumulated in the sclera and in the RPE/Choroid layer, it did not penetrate the retina. In contrast, SPHINX31 crossed into the retina and vitreous.

Figure 15:
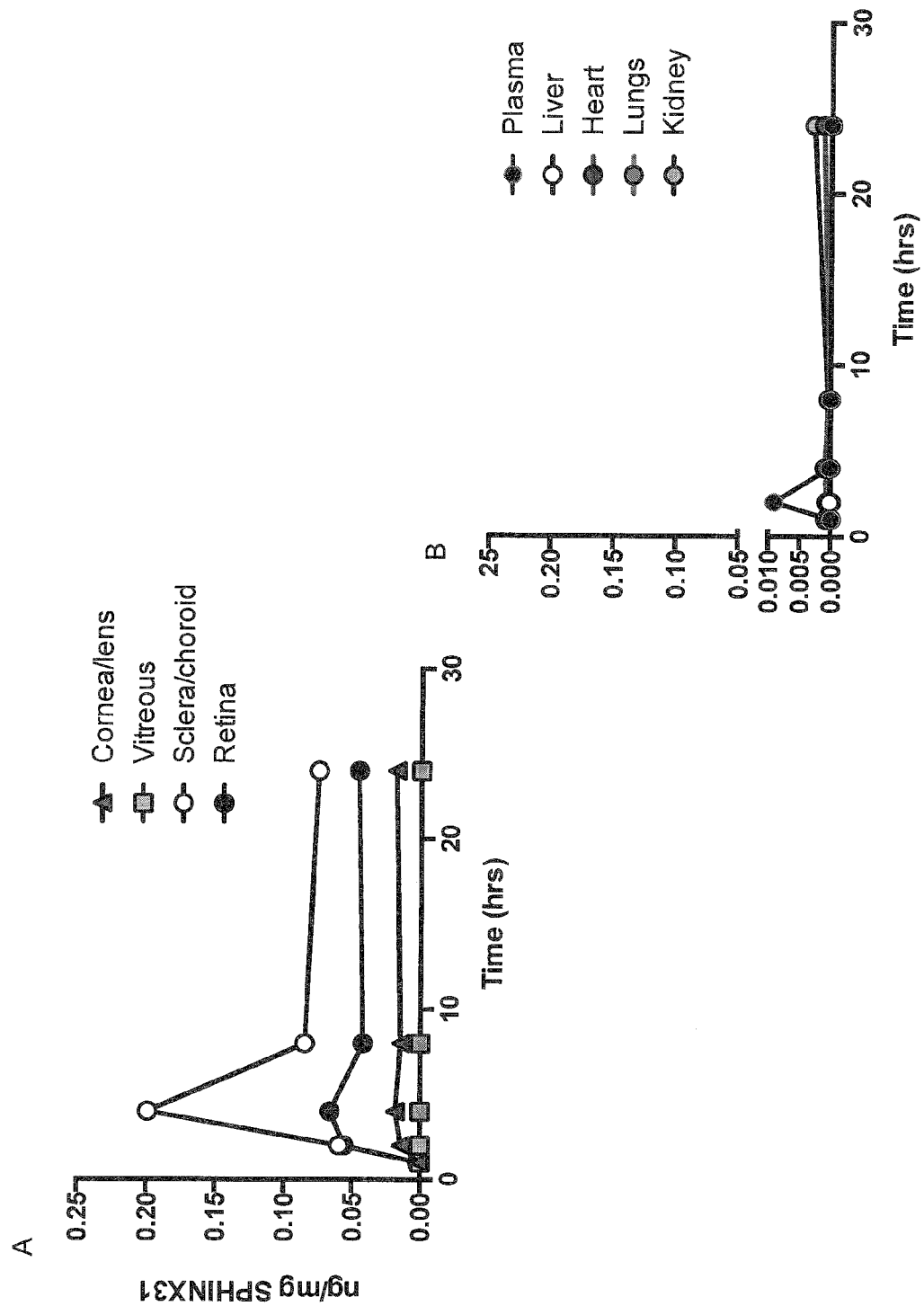
FIG. 15 shows (A) substantial accumulation of compound in the retina of a mouse 24 hours after addition of SPHINX31; and (B) accumulation of SPHINX31 in other tissues.

We also investigated accumulation of compounds of Formula (I) in various tissues in mice following treatment with 10 μl eye drop of 5 μg/ml SPHINX31. Mice were killed after 30 min, 1 hr, 4 hrs, 8 hrs or 24 hrs. Eyes were removed, and eye tissues dissected. Samples were subjected to extraction with control tracer chemical added to correct for extraction efficiency and subjected to mass spectroscopy for determination of quantity of compound per mg of tissue. FIG. 15A shows accumulation of SPHINX31 in different tissues of the eye. FIG. 15B shows accumulation of SPHINX31 in other tissues. These results show substantial accumulation of compound in the retina 24 hours after addition of SPHINX31.

Figure 16:
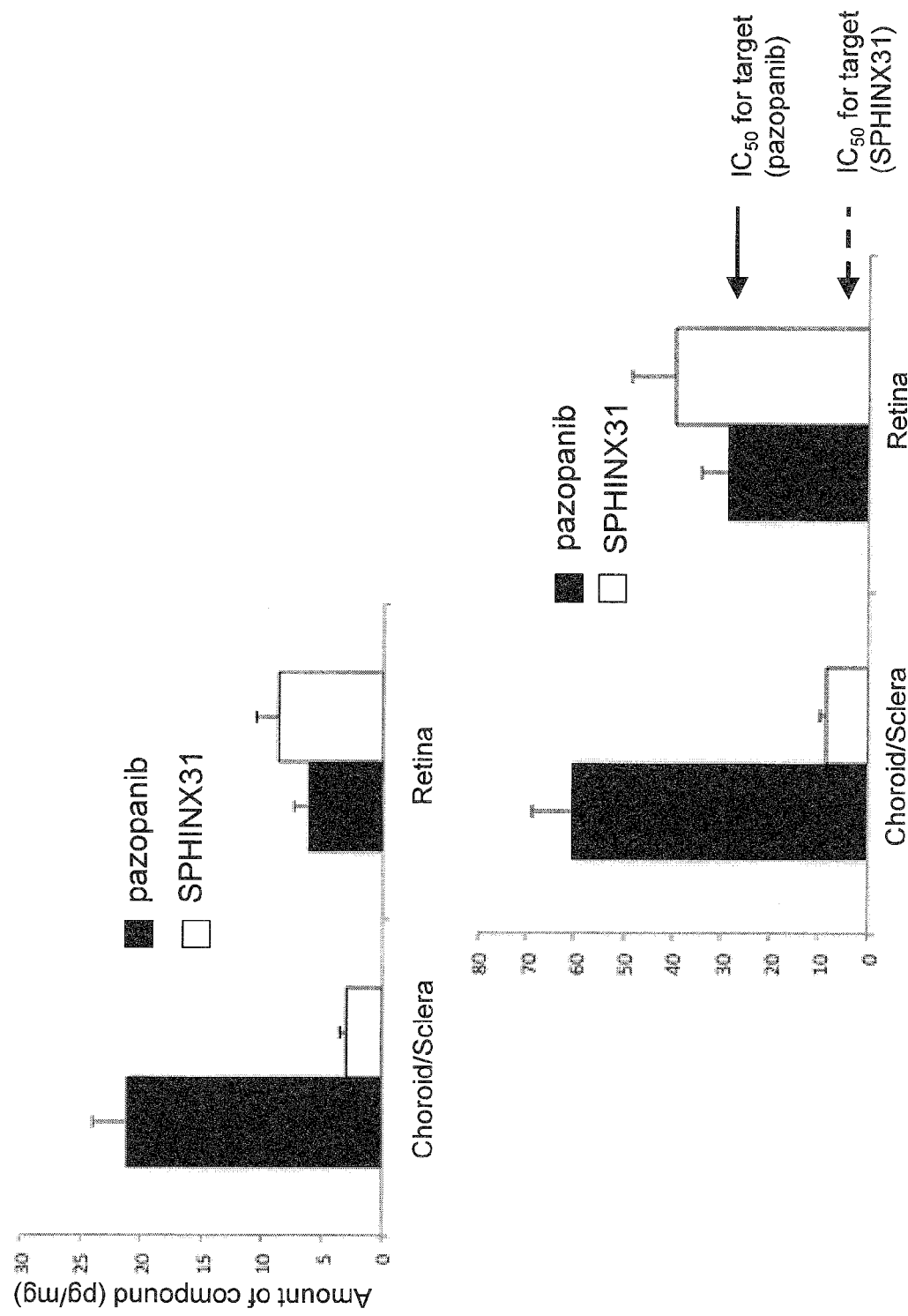
FIG. 16 shows greater retinal penetration for SPHINX31 relative to pazopanib in in vivo rabbit studies.

To determine if SPHINX31 could access the retina of an animal with a large eye a rabbit was exposed to 150 μg per day SPHINX31 or pazopanib (FIG. 16). After 6 days the animal was killed and the eyes harvested. Individual sections of sclera and retina from the rear half of the eye were then assayed for pazopanib or SPHINX31, Retinal penetration was seen for both pazopanib and SPHINX31, but the concentrations for SPHINX31 were 10× the $IC_{50}$ for the compound whereas for pazopanib the concentration was similar to the $IC_{50}$.

Figure 4:
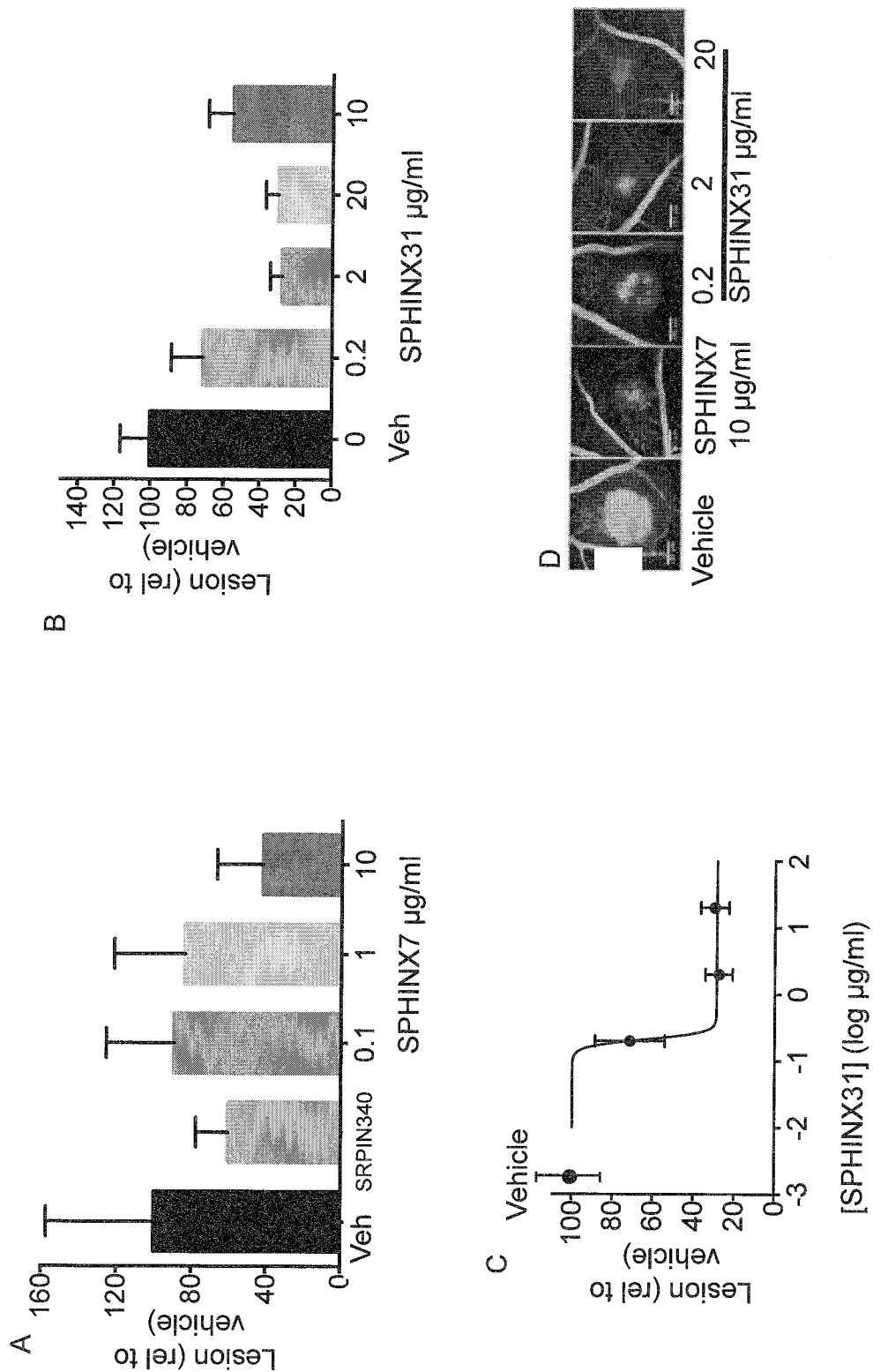
FIGS. 4 shows the results from the laser-induced mouse CNV model, where (A) and (B) show the effects of SPHINX31 in a laser-induced mouse CNV model relative to reference compounds SRPIN340 and SPHINX7; (C) shows the dose response curve for SPHINX31 in the laser-induced mouse CNV model; and (D) shows images of fluorescein angiography showing representative lesion sizes in the laser-induced mouse CNV model after treatment with SPHINX31 or reference compound SPHINX7.

We have previously shown that SRPK1 inhibition by SRPIN340 ($IC_{50}$ 1 μM), or SPHINX ($IC_{50}$ 0.44 μM) was anti-angiogenic in mouse models of choroidal neovascularisation, as eye drops with a maximum effect at 10 μg/ml, as these compounds are relatively lipophilic and have high penetrance into the eye. We therefore tested the effect of SPHINX31 as an eyedrop in this same model. SPHINX31 exerted a dose dependent inhibition of choroidal neovascularisation, with greater efficacy at 2 μg/ml, and an $IC_{50}$ of 0.24 μg/ml (FIG. 4).

Figure 17:
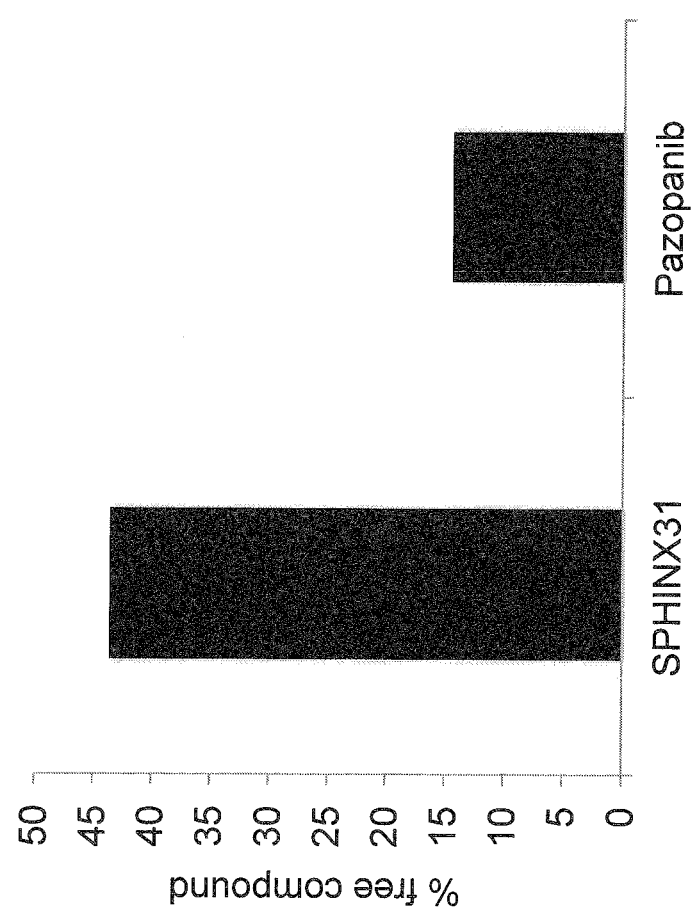
FIG. 17 shows that SPHINX31 binds to melanin substantially less than pazopanib does.

Concerns have been raised that compounds in the eye may be sequestered by melanin. We therefore measured the melanin binding of the compounds, and determined that SPHINX31 was substantially less bound than pazopanib to melanin. (FIG. 17). We also tested the half life of these compounds when exposed to human liver microsomes. This showed that the half lives of the compounds were as shown in Table 3 below.

TABLE 3

| Compound Number | Half life (mm) |
| --- | --- |
| 12 | 161.50 |
| 20 | 17.00 |
| 21 | 62.50 |
| Verapamil | 11.75 |

Figure 18:
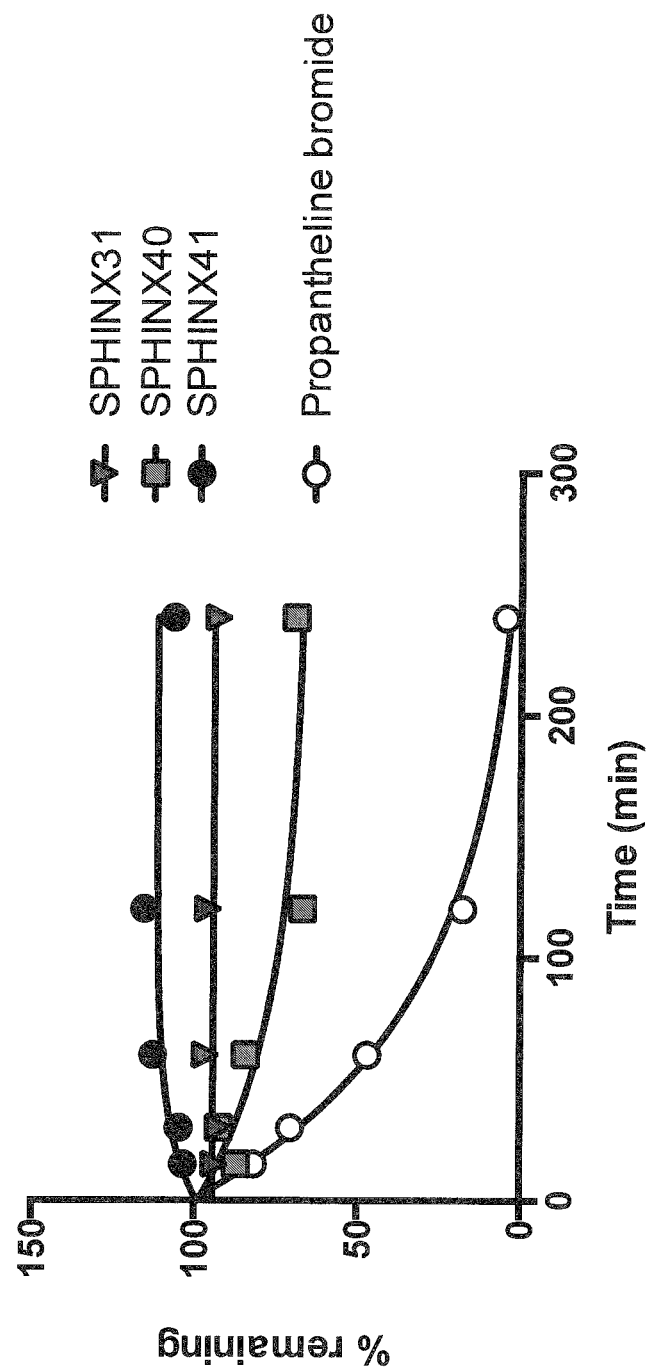
FIG. 18 shows the stability of compounds in human plasma relative to propantheline bromide.
Figure 21:
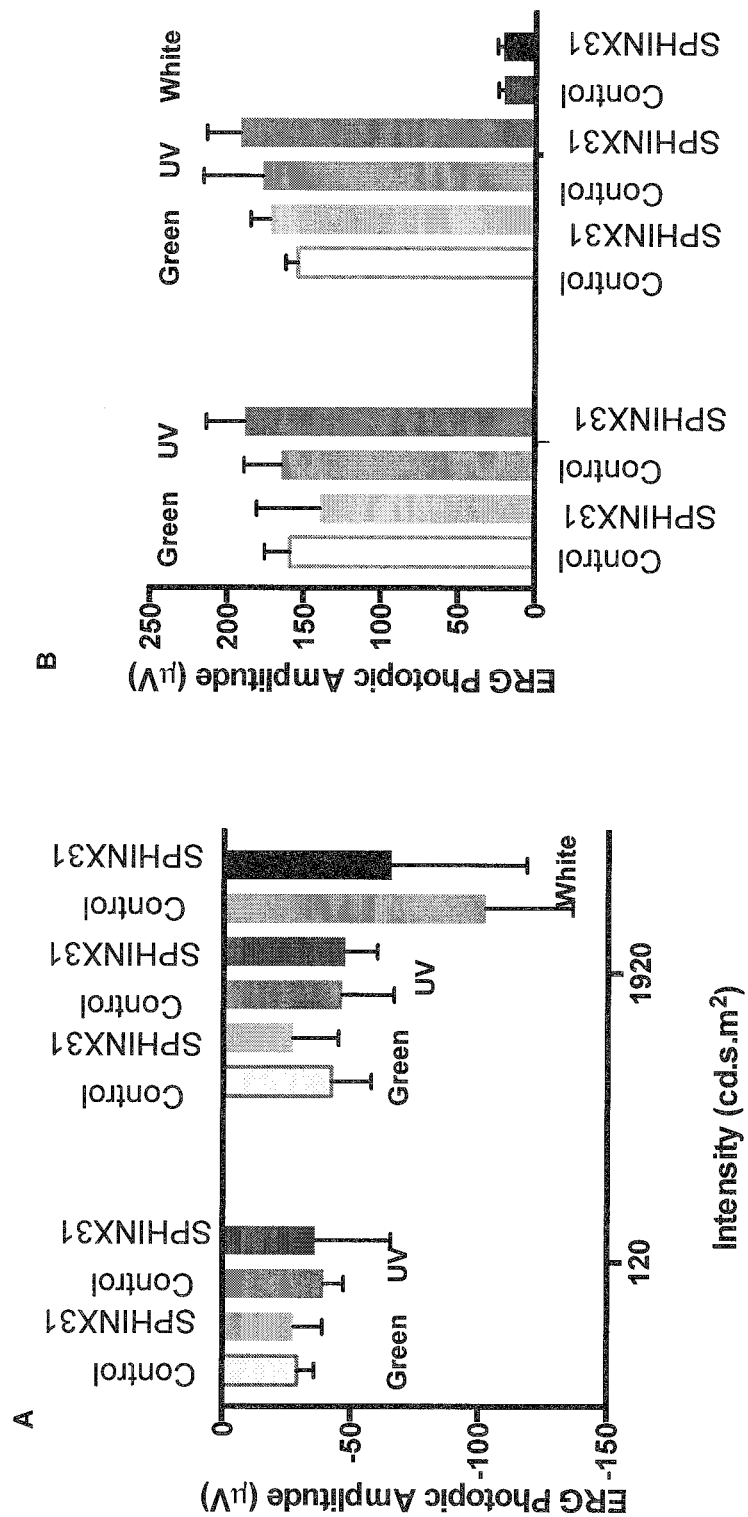
FIG. 21 shows Ganzfeld ERG recordings in mice taken 24 h after treatment with control or SPHINX31 at 2 μg/ml by topical eye drop administration, where the graphs show ERG amplitude for (A) A-wave; and (B) B-wave following stimulation with green light, UV light, or white light.

However, the compounds were stable in plasma (FIG. 18) indicating that they would most likely be taken to the liver and broken down there.

To test whether compounds of Formula (I) are safe to administer to patients we began a basic safety test of these compounds in vitro. A dose dependence of cytotoxicity to SPHINX7, SPHINX and SPHINX31 revealed that SPHINX31 had no effect, whereas reference compound SPHINX7 was toxic at doses greater than 10 μM.

We also tested whether these compounds could inhibit the human ether a go-go related gene (hERG) potassium channel using patch clamp electrophysiology. Novel drug candidates are typically screened for an ability to inhibit the 'hERG' potassium channel, due to the established association between pharmacological blockade of hERG channels and drug-induced long QT syndrome and torsades de poinses arrhythmia (Hancox et al., 2008; Gintant, 2008). SPHINX did not inhibit hERG, as has previously been described (Gammons et al., 2013).

Figure 5:
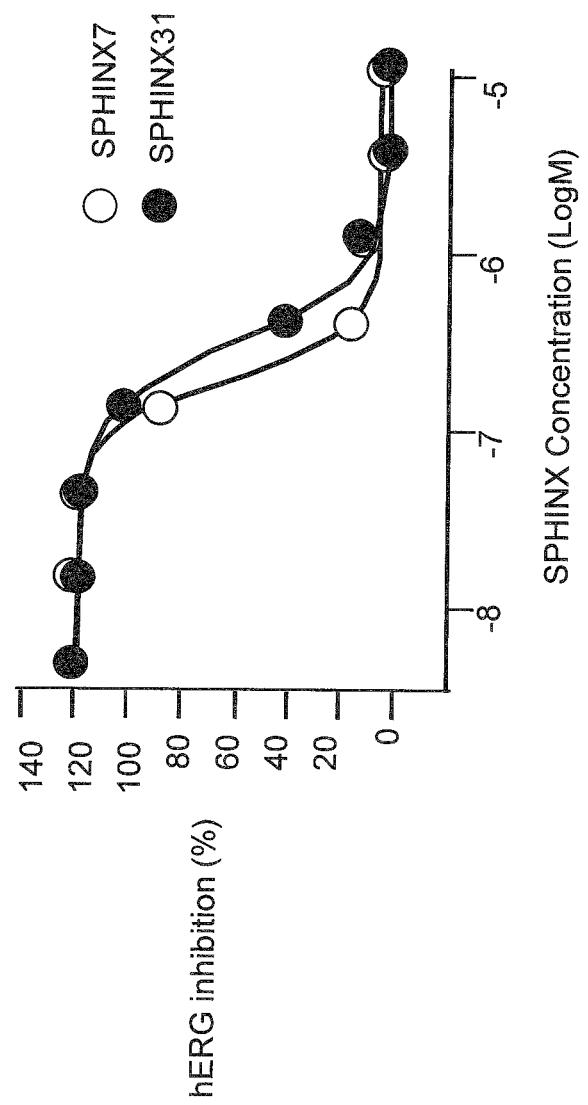
FIG. 5 shows the hERG inhibition profile of SPHINX31.

Plasma level of all compounds of Formula (I) tested during topical local application to the eye were extremely low (below detection level of 1 pM) and consequently substantial hERG channel block in the heart is unlikely to occur during in vivo use of these compounds as eye drops. The finding that known compounds SRPIN340 and SPHINX do not inhibit hERG suggests that it is possible to have significant pharmacological actions against SRPK1 without substantial hERG activity, (Gammons et al, 2013). We therefore tested SPHINX31, which inhibited hERG with an $IC_{50}$ of 0.3 μM, 100-fold higher than its $IC_{50}$ value against SRPK1 (3.2 nM) (FIG. 5).

We also tested SPHINX31 and its metabolite (termed SPHINX46, in FIG. 19) in an Ames test of genotoxicity, and both compounds induced no genotoxicity (FIG. 19).

To determine whether there was any indication of a toxic effect on nerve function normal mice were dosed with 2 μg/ml SPHINX31 and electroretinography determined on a Phoenix Ganzfeld ERG system. Scotopic ERG recordings were taken in dark adapted animals following stimulation with increasing intensities of green (FIGS. 20A, 20C, 20E, 20G) light (to activate M-cones and rods) or UV (FIGS. 20B, 20D, 20F, 20H) light (to activate S-cones and rods). The average ERG amplitude over time following stimulation with green light (FIG. 20A) and UV light (FIG. 20B) at 3.756 cd.s.m$^2$. ERG amplitude at different intensities of green (FIGS. 20C, 20E) or UV (FIGS. 20D, 20F) are shown for the A wave (FIGS. 20C, 20D) and B wave (FIGS. 20E, 20F). The ratio of A-wave: B-wave was unaffected by SPHINX31 treatment (FIG. 20G, FIG. 20H). After ERG recordings, eyes were enucleated, dissected, homogenised and spiked with SPHINX7 to measure extraction efficiency, then analysed by mass spectrometry (FIG. 20I, FIG. 20J). SPHINX31 was detected in the retina (0.165% of applied eye drop dose when normalised to extraction efficiency) and choroid (0.0175% of applied dose). SPHINX31 levels in control eyes are shown for comparison as background levels. Photopic ERG recordings were taken to isolate cone responses from rod responses following 10 minutes light adaptation and with continuous background stimulation with white light at an intensity of 30 cd.m.s$^2$. ERG amplitude for A-wave (A) and B-wave (B) at 120 and 1920 cd.s.m$^2$ green light (to activate M-cones and rods), UV light (to activate S-cones and rods) or white light. No effect was seen on scotopic or photopic activity, indicating that no visual functional toxicity effects were seen (FIG. 20,21).

Figure 22A:
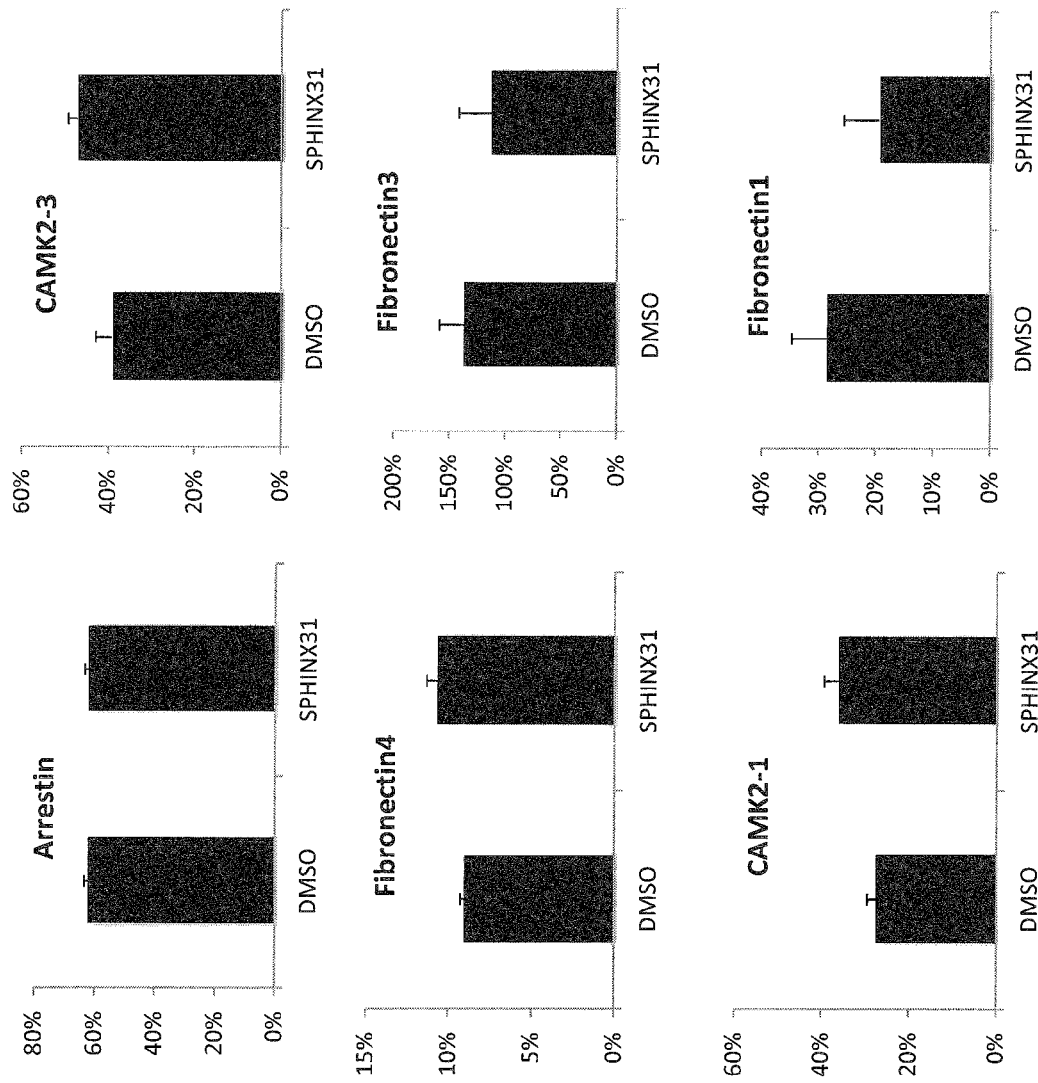
FIG. 22a shows the effects of SPHINX compounds on RPE cells expressing genes with alternative splicing, which are not linked to SRPK1.
Figure 22B:
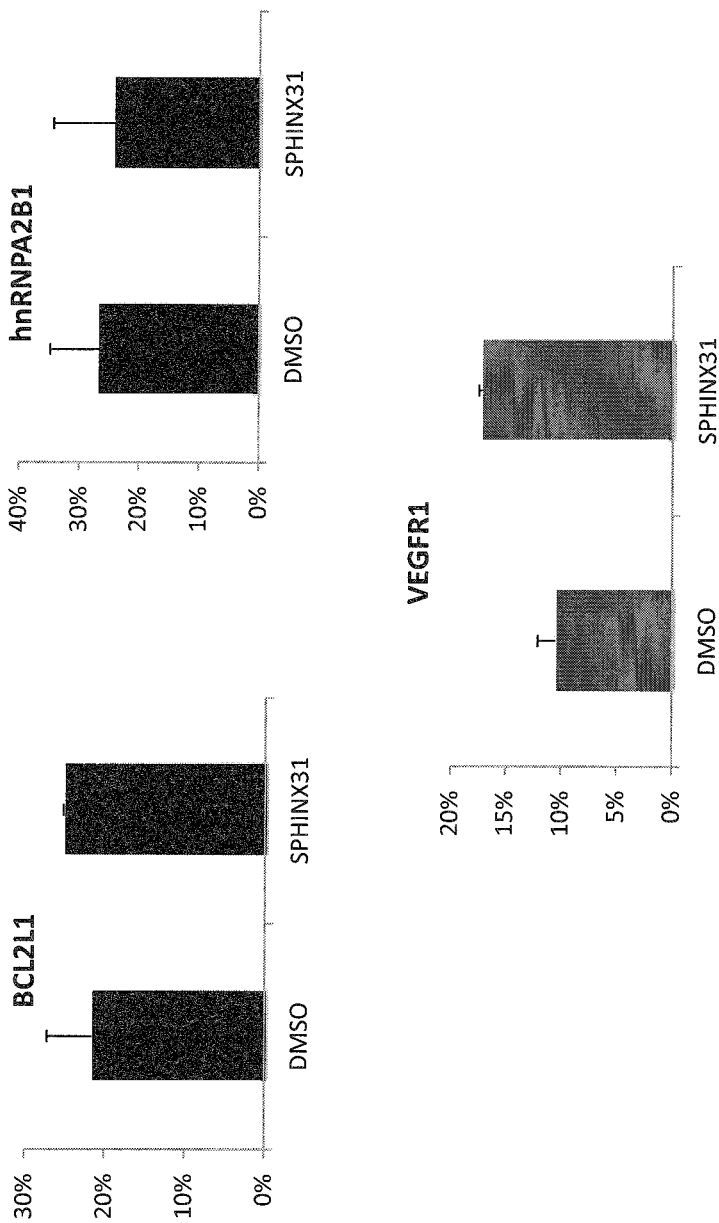
FIG. 22b shows the effects of SPHINX compounds on RPE expressing genes with alternative splicing, which are linked to SRPK1.
Figure 23:
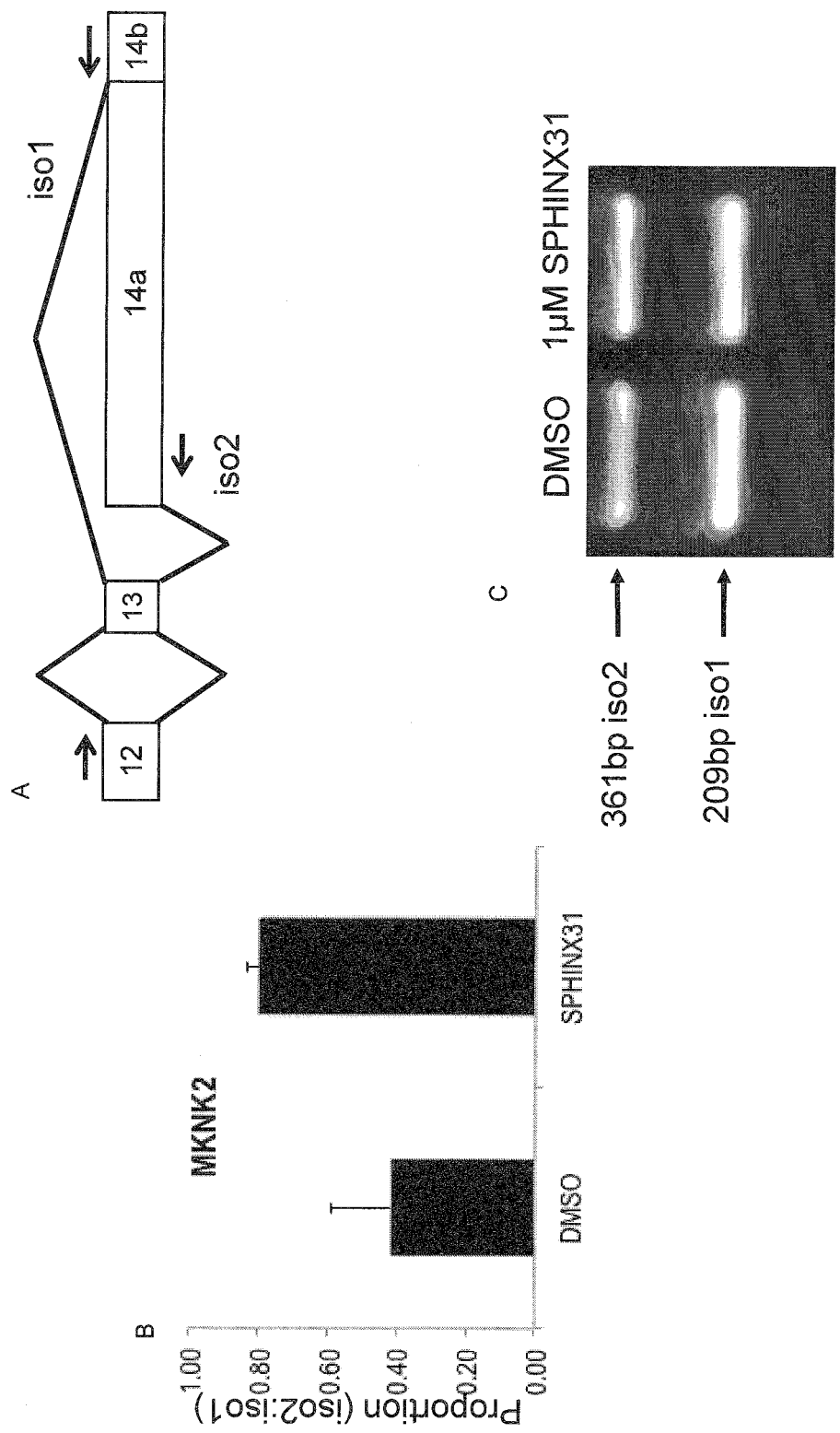
FIG. 23 shows the effect of SPHINX compounds on MKNK2, an RPE expressed gene with SRPK1 dependent alternative splicing, where (A) shows the alternative splicing of the MKNK2 gene; and (B) and (C) show the effect of SPHINX compounds on this alternative splicing.

Off target splicing effects were also screened by examining alternative splicing of a number of genes expressed in RPE cells and no changes in generic splicing were seen (FIG. 22), although VEGFR splicing was altered slightly. The known SRPK1 target MKNK2 was altered in these cell lines (FIG. 23).

The data presented in this study shows novel small molecular weight compound inhibitors for reducing proangiogenic VEGF mediated CNV associated with AMD. Furthermore we have shown that the compounds of the present invention penetrate into the back of the eye in large animal models, are effective at reducing CNV following topical administration in mice, for reducing tumour cell growth and are safe on tests undertaken so far.

TABLE 1

IC$_{50}$ data for compounds of Formula (I) tested in the SRPK1 inhibition assay

| Compound | Name | Structure | IC$_{50}$ (nM) |
|---|---|---|---|
| Reference Compound | SPHINX | | 440 |
| Reference Compound | SPHINX7 | | 54.7 |
| 12 | SPHINX31 | 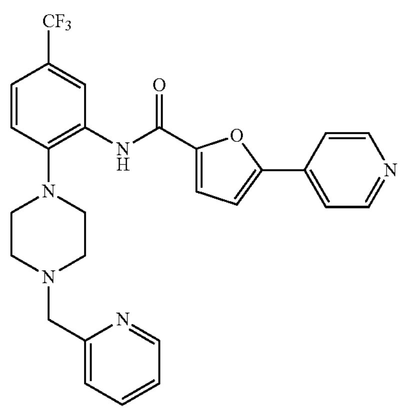 [SMILES: O=C(Nc1cc(C(F)(F)F)ccc1N1CCN(Cc2ccccn2)CC1)c1ccc(-c2ccncc2)o1] | 3.18 |
| 13 | SPHINX32 | 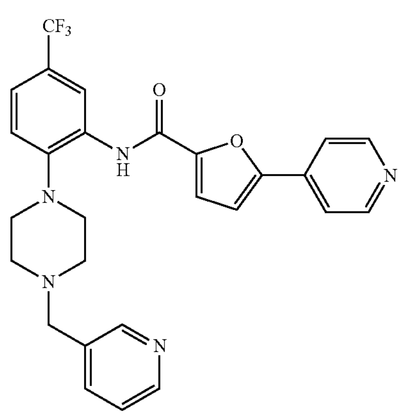 [SMILES: O=C(Nc1cc(C(F)(F)F)ccc1N1CCN(Cc2cccnc2)CC1)c1ccc(-c2ccncc2)o1] | 17.19 |

TABLE 1-continued

IC$_{50}$ data for compounds of Formula (I) tested in the SRPK1 inhibition assay

| Compound | Name | Structure | IC$_{50}$ (nM) |
|---|---|---|---|
| 14 | SPHINX33 | (structure) | 7.18 |

Additional compounds tested are presented in Table 2 below:

TABLE 2

IC$_{50}$ data for compounds of Formula (I) tested in the SRPK1 inhibition assay

| Compound | n | R$_1$ | R$_2$ | X | Y | Z | IC$_{50}$ (nM) |
|---|---|---|---|---|---|---|---|
| 15 | 1 | 2-pyridyl | H | CH | CH | O | 16.6 |
| 16 | 1 | 2-pyridyl | CH$_3$ | CH | CH | O | 38.2 |
| 17 | 1 | 2-pyridyl | phenyl | CH | CH | O | 110.7 |
| 18 | 1 | 2-pyridyl | indol-5-yl | CH | CH | O | 13.9 |
| 19 | 1 | phenyl | H | CH | CH | O | 14.1 |
| 20 | 1 | phenyl | CH$_3$ | CH | CH | O | 4.4 |

TABLE 2-continued

IC$_{50}$ data for compounds of Formula (I) tested in the SRPK1 inhibition assay

| Compound | n | R$_1$ | R$_2$ | X | Y | Z | IC$_{50}$ (nM) |
|---|---|---|---|---|---|---|---|
| 21 | 1 | phenyl | pyridin-3-yl | CH | CH | O | 4.6 |
| 22 | 1 | phenyl | pyridin-4-yl | CH | CH | O | 14.8 |
| 23 | 1 | phenyl | phenyl | CH | CH | O | 4008.7 |
| 24 | 1 | phenyl | 1H-indol-5-yl | CH | CH | O | 3507.5 |
| 25 | 1 | pyridin-2-yl | pyridin-3-yl | CH | CH | O | 13.5 |
| 26 | 1 | pyridin-2-yl | phenyl | N | N | O | 10000 |
| 27 | 1 | pyridin-2-yl | —CH$_3$ | N | CH | O | 10000 |
| 28 | 1 | pyridin-2-yl | —CH$_3$ | N | N | O | 10000 |
| 29 | 1 | pyridin-2-yl | pyridin-4-yl | N | N | O | 10000 |
| 30 | 1 | 4-methoxyphenyl | pyridin-4-yl | CH | CH | O | 335.7 |

TABLE 2-continued

IC$_{50}$ data for compounds of Formula (I) tested in the SRPK1 inhibition assay

| Compound | n | R$_1$ | R$_2$ | X | Y | Z | IC$_{50}$ (nM) |
|---|---|---|---|---|---|---|---|
| 31 | 1 | 4-(2-SMe-pyrimidinyl) | —CH$_3$ | CH | CH | O | 1.9 |
| 32 | 1 | 3-methoxyphenyl | 4-pyridyl | CH | CH | O | 1547.0 |
| 33 | 1 | 2-pyridyl | phenyl | CH | N | O | 4027.2 |
| 34 | 1 | 2-pyridyl | phenyl | O | N | N | 5308.8 |
| 35 | 1 | 2-pyridyl | phenyl | N | O | N | 10000 |
| 36 | 1 | 2-pyridyl | 4-(2-OCH$_3$-pyridyl) | CH | CH | O | 170.0 |
| 37 | 1 | 2-pyridyl | 5-(2-OCH$_3$-pyridyl) | CH | CH | O | 323.0 |
| 38 | 1 | 2-pyridyl | 3-(hydroxymethyl)phenyl | CH | CH | O | 5.0 |
| 39 | 1 | 2-pyridyl | 4-tetrahydropyranyl | CH | CH | O | 2.6 |
| 40 | 1 | H | H | CH | CH | S | 4688 |

TABLE 2-continued

IC$_{50}$ data for compounds of Formula (I) tested in the SRPK1 inhibition assay

| Compound | n | R$_1$ | R$_2$ | X | Y | Z | IC$_{50}$ (nM) |
|---|---|---|---|---|---|---|---|
| 41 | 1 | H | phenyl | NH | CH | N | 493 |
| 42 | 1 | 1H-indol-3-yl | pyridin-4-yl | CH | CH | O | 164 |
| 43 | 1 | pyrazin-2-yl | H | CH | CH | O | 183 |
| 44 | 1 | pyridin-2-yl | H | NH | N | N | 8413 |
| 45 | 1 | pyridin-2-yl | CH$_2$OH | CH | CH | O | 119 |

TABLE 4

Analytical data for synthesized compounds

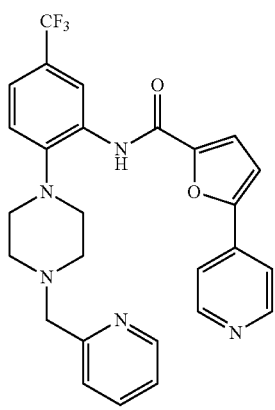 [SMILES: O=C(Nc1cc(C(F)(F)F)ccc1N1CCN(Cc2ccccn2)CC1)c1ccc(-c2ccncc2)o1]

Compound 12
Mp: 157-159° C.
$^1$H NMR (300 MHz, CDCl$_3$) δ 2.85 (br s, 4H), 3.04 (br s, 4H), 3.78 (s, 2H), 7.06 (d, J = 3.7 Hz, 1H), 7.20 (m, 1H), 7.31-7.41 (m, 4H), 7.65-7.72 (m, 3H), 8.60 (d, J = 4.5 Hz, 1H), 8.80-8.87 (m, 3H), 9.65 (br s, 1H)
HRMS (ESI-MS): m/z calcd for C$_{27}$H$_{24}$F$_3$N$_5$O$_2$ (M$^+$ + H) 508.19603, found 508.19315

TABLE 4-continued

Analytical data for synthesized compounds

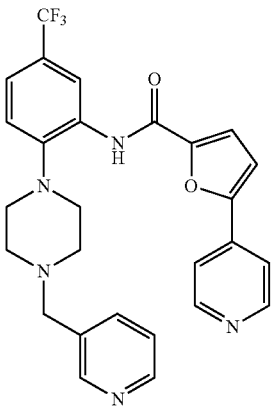 [SMILES: O=C(Nc1cc(C(F)(F)F)ccc1N1CCN(Cc2cccnc2)CC1)c1ccc(-c2ccncc2)o1]

Compound 13
Mp: 166-168° C.
$^1$H NMR (400 MHz, CDCl$_3$) δ 2.79 (br s, 4H), 3.04 (br s, 4H), 3.73 (s, 2H), 7.06 (d, J = 3.7 Hz, 1H), 7.23 (m, 1H), 7.31-7.41 (m, 4H), 7.62-7.69 (m, 3H), 8.54 (d, J = 4.5 Hz, 1H), 8.67-8.76 (m, 3H), 9.65 (br s, 1H)
HRMS (ESI-MS): m/z calcd for C$_{27}$H$_{24}$F$_3$N$_5$O$_2$ (M$^+$ + H) 508.19603, found 508.19315

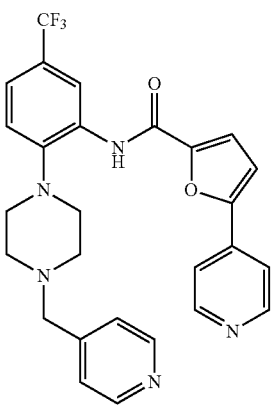 [SMILES: O=C(Nc1cc(C(F)(F)F)ccc1N1CCN(Cc2ccncc2)CC1)c1ccc(-c2ccncc2)o1]

Compound 14
Mp: 188-190° C.
$^1$H NMR (400 MHz, CDCl$_3$) δ 2.77 (br s, 4H), 3.04 (m, 4H), 3.61 (s, 2H), 7.07 (d, J = 3.7 Hz, 1H), 7.29 (m, 2H), 7.32-7.42 (m, 3H), 7.72 (m, 2H), 8.56 (m, 2H), 8.78 (m, 2H), 8.86 (d, J = 1.8 Hz, 1H), 9.63 (br s, 1H)
HRMS (ESI-MS): m/z calcd for C$_{27}$H$_{24}$F$_3$N$_5$O$_2$ (M$^+$ + H) 508.19603, found 508.19423

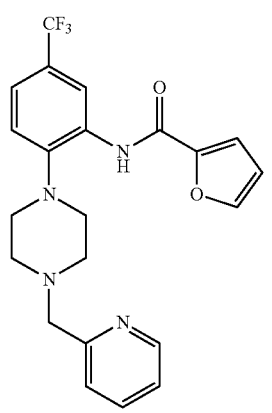 [SMILES: O=C(Nc1cc(C(F)(F)F)ccc1N1CCN(Cc2ccccn2)CC1)c1ccco1]

Compound 15
$^1$H NMR (300 MHz, CDCl$_3$) δ 2.75 (br s, 4H), 2.97 (t, J = 4.6 Hz, 4H), 3.77 (s, 2H), 6.56 (dd, J = 3.5, 1.8 Hz, 1H), 7.15-7.23 (m, 3H), 7.28-7.32 (m, 1H), 7.44 (d, J = 7.8 Hz, 1H), 7.54 (dd, J = 1.8, 0.8 Hz, 1H), 7.63-7.69 (m, 1H), 8.55-8.57 (m, 1H), 8.78 (d, J = 1.8 Hz, 1H), 9.39 (br s, 1H).
HRMS (ESI-MS): m/z calcd for C$_{22}$H$_{21}$F$_3$N$_4$O$_2$ (M$^+$ + H) 431.1695, found 431.1644

TABLE 4-continued

Analytical data for synthesized compounds

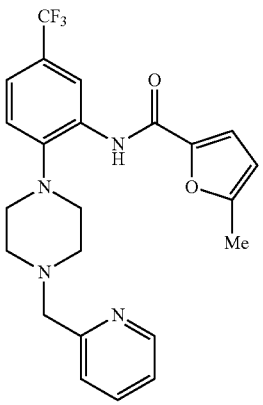 [SMILES: Cc1ccc(C(=O)Nc2cc(C(F)(F)F)ccc2N2CCN(Cc3ccccn3)CC2)o1]

Compound 16
$^1$H NMR (400 MHz, CDCl$_3$) δ 2.43 (s, 3H), 2.78 (br s, 4H), 3.00 (t, J = 4.6 Hz, 4H), 3.77 (s, 2H), 6.18 (d, J = 3.4 Hz, 1H), 7.13 (d, J = 3.4 Hz, 1H), 7.19 (dd, J = 7.2, 5.0 Hz, 1H), 7.23 (d, J = 8.3 Hz, 1H), 7.30 (d, J = 8.3, 1.7 Hz, 1H), 7.46 (d, J = 7.8 Hz, 1H), 7.66-7.70 (m, 1H), 8.57-8.58 (m, 1H), 8.79 (d, J = 1.7 Hz, 1H), 9.42 (s, 1H)
HRMS (ESI-MS): m/z calcd for C$_{23}$H$_{23}$F$_3$N$_4$O$_2$ (M$^+$ + H) 467.1671, found 467.1616

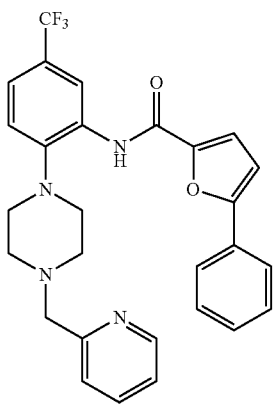

Compound 17
$^1$H NMR (400 MHz, CDCl$_3$) δ 2.84 (br s, 4H), 3.04 (t, J = 4.5 Hz, 4H), 3.77 (s, 2H), 6.83 (d, J = 3.6 Hz, 1H), 7.18 (ddd, J = 7.6, 4.9, 1.1 Hz, 1H), 7.30 (d, J = 8.3 Hz, 1H), 7.34-7.46 (m, 4H), 7.53-7.57 (m, 2H), 7.64-7.68 (m, 1H), 7.86-7.88 (m, 2H), 8.58-8.60 (m, 1H), 8.89 (d, J = 1.8 Hz, 1H), 9.63 (s, 1H)
HRMS (ESI-MS): m/z calcd for C$_{28}$H$_{25}$F$_3$N$_4$O$_2$ (M$^+$ + H) 507.2008, found 507.1943

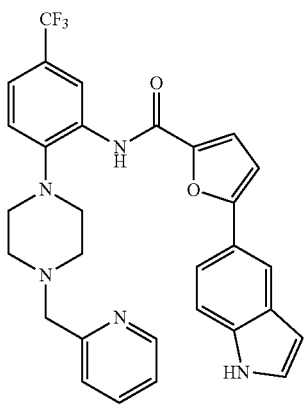 [SMILES: O=C(Nc1cc(C(F)(F)F)ccc1N1CCN(Cc2ccccn2)CC1)c1ccc(-c2ccc3[nH]ccc3c2)o1]

Compound 18
$^1$H NMR (400 MHz, d6-DMSO) δ 2.78 (br s, 4H), 2.98 (br s, 4H), 3.71 (s, 2H), 6.63 (br s, 1H), 7.08 (d, J = 3.6 Hz, 1H), 7.24 (dd, J = 6.9, 5.5 Hz, 1H), 7.39 (d, J = 3.6 Hz, 1H), 7.42-7.51 (m, 5H), 7.59 (d, J = 8.5 Hz, 1H), 7.72-7.76 (m, 2H), 8.20 (s, 1H), 8.48 (br d, J = 4.5 Hz, 1H), 8.70 (s, 1H), 9.61 (s, 1H), 11.42 (s, 1H)
HRMS (ESI-MS): m/z calcd for C$_{30}$H$_{27}$F$_3$N$_5$O$_2$ (M$^+$ + H) 546.2117, found 546.2073

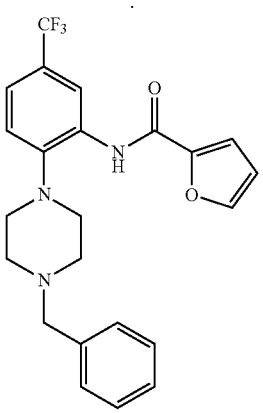

Compound 19
Mp: 96-99° C.
$^1$H NMR (300 MHz, CDCl$_3$) δ 2.72 (br s, 4H), 2.98 (t, J = 4.8 Hz, 4H), 3.66 (s, 2H), 6.60 (dd, J = 3.5, 1.8 Hz, 1H), 7.22-7.40 (m, 8H), 7.54 (dd, J = 1.9, 0.8 Hz, 1H), 8.81 (d, J = 1.8 Hz), 9.43 (br s, 1H)
HRMS (ESI-MS): m/z calcd for C$_{23}$H$_{22}$F$_3$N$_3$O$_2$ (M$^+$ + H) 430.17369, found 430.16879

TABLE 4-continued

Analytical data for synthesized compounds

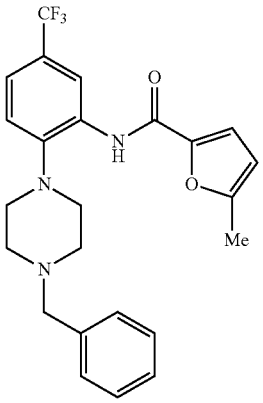 [SMILES: Cc1ccc(C(=O)Nc2cc(C(F)(F)F)ccc2N2CCN(Cc3ccccc3)CC2)o1]

Compound 20
Mp: 124-128° C.
$^1$H NMR (300 MHz, CDCl$_3$) δ 2.44 (s, 3H), 2.72 (br s, 4H), 2.98 (t, J = 4.8 Hz, 4H), 3.63 (s, 2H), 6.20 (dd, J = 0.8, 3.5 Hz, 1H), 7.14 (d, J = 3.2 Hz, 1H), 7.21-7.26 (m, 1H), 7.28-7.38 (m, 7H), 8.81 (d, J = 1.8 Hz, 1H), 9.42 (br s, 1H)
HRMS (ESI-MS): m/z calcd for C$_{24}$H$_{24}$F$_3$N$_3$O$_2$ (M$^+$ + H) 444.18934, found 444.18488

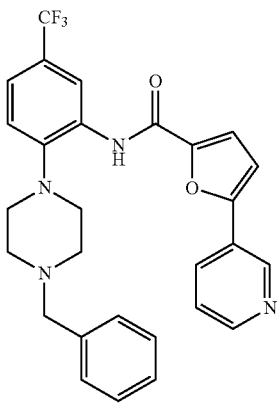 [SMILES: O=C(Nc1cc(C(F)(F)F)ccc1N1CCN(Cc2ccccc2)CC1)c1ccc(-c2cccnc2)o1]

Compound 21
Mp: 62-64° C.
$^1$H NMR (300 MHz, CDCl$_3$) δ 2.76 (br s, 4H), 3.01 (t, J = 4.8 Hz, 4H), 3.63 (s, 2H), 6.94 (d, J = 3.6 Hz, 1H), 7.27-7.40 (m, 8H), 7.47 (ddd, J = 8.2, 4.9, 0.8 Hz, 1H), 8.13 (dt, J = 8.0, 1.9 Hz, 1H), 8.70 (dd, J = 4.9, 1.6 Hz, 1H), 8.86 (d, J = 1.7 Hz, 1H), 9.20 (dd, J = 2.3, 0.7 Hz, 1H), 9.67 (br s, 1H)
HRMS (ESI-MS): m/z calcd for C$_{28}$H$_{25}$F$_3$N$_4$O$_2$ (M$^+$ + H) 507.20024, found 507.2031

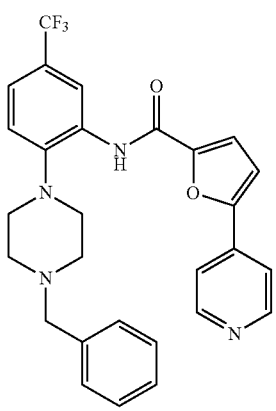

Compound 22
Mp: 178-180° C.
$^1$H NMR (300 MHz, CDCl$_3$) δ 2.77 (br s, 4H), 3.02 (t, J = 4.7 Hz, 4H), 3.62 (s, 2H), 7.07 (d, J = 3.6 Hz, 1H), 7.31-7.42 (m, 8H), 7.74 (dd, J = 4.4, 1.7 Hz, 2H), 8.79 (dd, J = 4.4, 1.8 Hz, 2H), 8.87 (d, J = 1.6 Hz, 1H), 9.67 (br s, 1H)
HRMS (ESI-MS): m/z calcd for C$_{28}$H$_{25}$F$_3$N$_4$O$_2$ (M$^+$ + H) 507.20024, found 507.19342

TABLE 4-continued

Analytical data for synthesized compounds

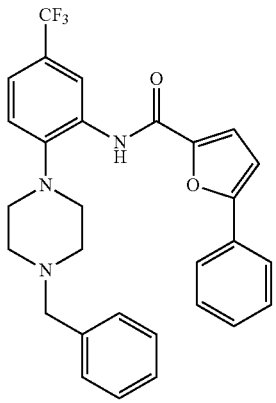

Compound 23
Mp: 150-154° C.
$^1$H NMR (300 MHz, CDCl$_3$) δ 2.78 (br s, 4H), 3.01 (t, J = 4.6 Hz, 4H), 3.60 (s, 2H), 6.85 (d, J = 3.7 Hz, 1H), 7.27-7.39 (m, 8H), 7.43-7.49 (m, 1H), 7.51-7.58 (m, 2H), 7.90 (dd, J = 8.6, 1.6 Hz), 8.89 (d, J = 1.6 Hz), 9.65 (br s, 1H)
HRMS (ESI-MS): m/z calcd for C$_{29}$H$_{26}$F$_3$N$_3$O$_2$ (M$^+$ + H) 506.20499, found 506.19922

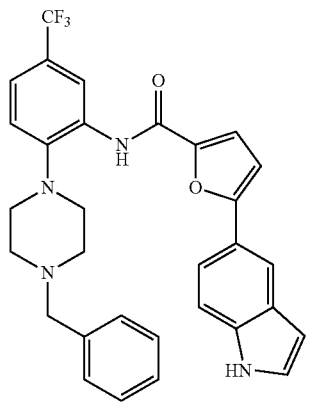 [SMILES: O=C(Nc1cc(C(F)(F)F)ccc1N1CCN(Cc2ccccc2)CC1)c1ccc(-c2ccc3[nH]ccc3c2)o1]

Compound 24
Mp: 228-230° C.
$^1$H NMR (300 MHz, CDCl$_3$) δ 2.80 (br s, 4H), 3.02 (t, J = 4.5 Hz, 4H), 3.60 (s, 2H), 6.71 (t, J = 2.1 Hz), 6.78 (d, J = 3.6 Hz), 7.19-7.40 (m, 9H), 7.54 (d, J = 8.4 Hz, 1H), 7.72 (dd, J = 8.6, 0.8 Hz, 1H), 8.21 (s, 1H), 8.38 (br s, 1H), 8.89 (d, J = 1.5 Hz, 1H), 9.62 (br s, 1H)
HRMS (ESI-MS): m/z calcd for C$_{31}$H$_{27}$F$_3$N$_4$O$_2$ (M$^+$ + H) 545.21589, found 545.21100

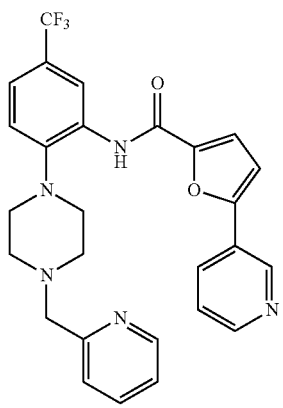 [SMILES: O=C(Nc1cc(C(F)(F)F)ccc1N1CCN(Cc2ccccn2)CC1)c1ccc(-c2cccnc2)o1]

Compound 25
$^1$H NMR (400 MHz, CDCl$_3$) δ 2.81 (br s, 4H), 3.02 (t, J = 4.5 Hz, 4H), 3.77 (s, 2H), 6.91 (d, J = 3.7 Hz, 1H), 7.16 (ddd, J = 7.6, 4.8, 1.0 Hz, 1H), 7.29 (d, J = 8.3 Hz, 1H), 7.34-7.36 (m, 2H), 7.41 (d, J = 8.0 Hz, 1H), 7.49 (dd, J = 8.1, 4.8 Hz, 1H), 7.61-7.67 (m, 1H), 8.10-8.13 (m, 1H), 8.56-8.58 (m, 1H), 8.66 (dd, J = 4.9, 1.6 Hz, 1H), 8.84 (d, J = 1.7 Hz, 1H), 9.14 (d, J = 2.2 Hz, 1H), 9.64 (s, 1H)
HRMS (ESI-MS): m/z calcd for C$_{27}$H$_{24}$F$_3$N$_4$O$_2$ (M$^+$ + H) 508.1960, found 508.1902

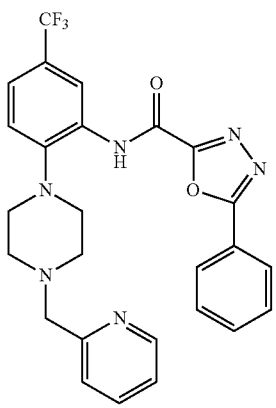

Compound 26
$^1$H NMR (400 MHz; CDCl$_3$) δ 2.84 (br s, 4H), 3.03 (m, 4H), 3.80 (s, 2H), 7.18 (ddd, J = 7.4, 4.9, 0.9 Hz, 1H), 7.30 (d, J = 8.3 Hz, 1H), 7.41-7.44 (m, 2H), 7.54-7.64 (m, 3H), 7.67 (m, 1H), 8.18-8.21 (m, 2H), 8.60-8.61 (m, 1H), 8.75 (d, J = 1.8 Hz, 1H), 10.2 (br s, 1H)
HRMS (ESI-MS): m/z calcd for C$_{26}$H$_{24}$F$_3$N$_4$O$_2$ (M$^+$ + H) 509.1913, found 509.1875

TABLE 4-continued

Analytical data for synthesized compounds

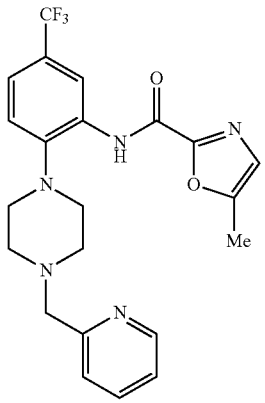 [SMILES: Cc1cnc(C(=O)Nc2cc(C(F)(F)F)ccc2N2CCN(Cc3ccccn3)CC2)o1]

Compound 27
$^1$H NMR (300 MHz; CDCl$_3$) δ 2.44 (d, J = 1.1 Hz, 3H), 2.79 (br s, 4H), 2.99 (t, J = 4.8 Hz, 4H), 3.79 (s, 2H), 6.93 (q, J = 1.1 Hz, 1H), 7.18 (ddd, J = 7.6, 5.0, 1.1 Hz, 1H), 7.23 (d, J = 8.3 Hz, 1H), 7.35 (dd, J = 8.3, 2.1 Hz, 1H), 7.45 (d, J = 7.8 Hz, 1H), 7.67 (td, J = 7.7, 1.8 Hz, 1H), 8.56-8.59 (m, 1H), 8.73 (d, J = 1.8 Hz, 1H), 9.94 (br s, 1H)
HRMS (ESI-MS): m/z calcd for C$_{22}$H$_{22}$F$_3$N$_5$O$_2$Na (M$^+$ + Na) 468.1623, found 468.1610

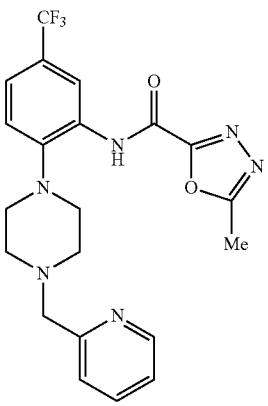 [SMILES: Cc1nnc(C(=O)Nc2cc(C(F)(F)F)ccc2N2CCN(Cc3ccccn3)CC2)o1]

Compound 28
$^1$H NMR (300 MHz; CDCl$_3$) δ 2.67 (s, 3H), 2.79 (br s, 4H), 2.99 (t, J = 4.6 Hz, 4H), 3.76 (s, 2H), 7.16 (dd, J = 7.1, 5.3 Hz, 1H), 7.28 (d, J = 8.1 Hz, 1H), 7.38-7.41 (m, 2H), 7.54-7.64 (m, 3H), 7.65 (td, J = 7.7, 1.8 Hz, 1H), 8.18-8.21 (m, 2H), 8.57-8.59 (m, 1H), 8.68 (br s, 1H), 10.04 (br s, 1H)
HRMS (ESI-MS): m/z calcd for C$_{21}$H$_{21}$F$_3$N$_6$O$_2$Na (M$^+$ + Na) 469.1576, found 469.1527

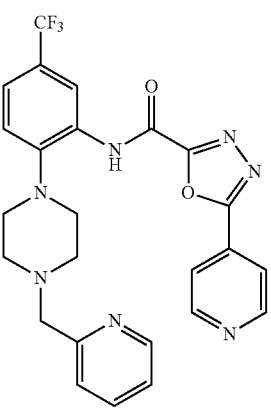

Compound 29
$^1$H NMR (300 MHz; CDCl$_3$) δ 2.83 (br s, 4H), 3.03 (t, J = 4.5 Hz, 4H), 3.79 (s, 2H), 7.18 (dd, J = 6.9, 5.1 Hz, 1H), 7.31 (d, J = 8.3 Hz, 1H), 7.41-7.45 (m, 2H), 7.67 (td, J = 7.6, 1.9 Hz, 1H), 8.02-8.04 (m, 2H), 8.59-8.60 (m, 1H), 8.73 (d, J = 1.4 Hz, 1H), 8.87-8.89 (m, 2H), 10.21 (br s, 1H)
HRMS (ESI-MS): m/z calcd for C$_{25}$H$_{23}$F$_3$N$_7$O$_2$ (M$^+$ + H) 510.1865, found 510.1860

TABLE 4-continued

Analytical data for synthesized compounds

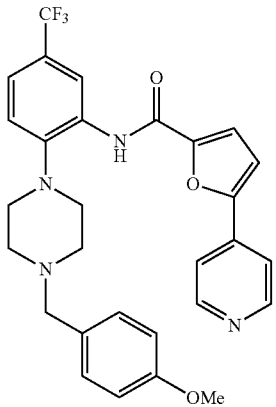 [SMILES: COc1ccc(CN2CCN(c3ccc(C(F)(F)F)cc3NC(=O)c3ccc(-c4ccncc4)o3)CC2)cc1]

Compound 30
Mp: 165-167° C.
$^1$H NMR (300 MHz, CDCl$_3$) δ 2.74 (br s, 4H), 3.00 (t, J = 4.4 Hz, 4H), 3.54 (s, 2H), 3.78 (s, 3H), 6.85 (d, J = 8.4 Hz, 2H), 7.05 (d, J = 3.6 Hz, 1H), 7.23 (d, J = 8.4 Hz, 2H), 7.30 (d, J = 8.1 Hz, 1H), 7.34-7.40 (m, 2H), 7.73 (d, J = 5.2 Hz, 2H), 8.78 (d, J = 5.2 Hz, 2H), 8.85 (s, 1H), 9.66 (br s, 1H)
HRMS (ESI-MS): m/z calcd for C$_{29}$H$_{27}$F$_3$N$_4$O$_3$ (M$^+$ + H) 537.21080, found 537.21030

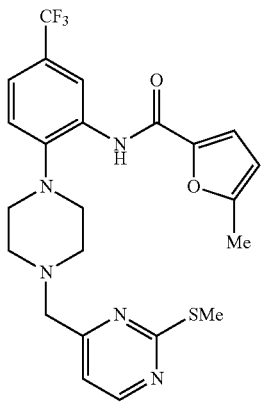 [SMILES: CSc1nccc(CN2CCN(c3ccc(C(F)(F)F)cc3NC(=O)c3ccc(C)o3)CC2)n1]

Compound 31
$^1$H NMR (400 MHz, CDCl$_3$) δ 2.43 (s, 3H), 2.56 (s, 3H), 2.79 (br s, 4H), 3.00 (t, J = 4.4 Hz, 4H), 3.68 (s, 2H), 6.19 (d, J = 3.0 Hz, 1H), 7.13 (d, J = 3.2 Hz, 1H), 7.21 (d, J = 5.0 Hz, 1H), 7.24 (d, J = 8.1 Hz, 1H), 7.32 (d, J = 8.1 Hz, 1H), 8.50 (d, J = 5.0 Hz, 1H), 8.80 (s, 1H), 9.37 (s, 1H)
HRMS (ESI-MS): m/z calcd for C$_{23}$H$_{24}$F$_3$N$_5$O$_2$S (M$^+$ + Na) 514.1501, found 514.1456

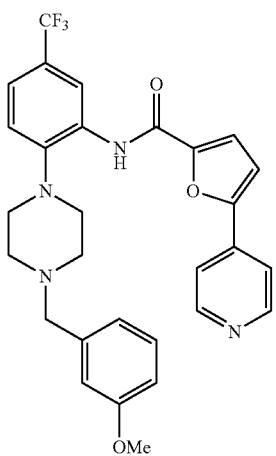 [SMILES: COc1cccc(CN2CCN(c3ccc(C(F)(F)F)cc3NC(=O)c3ccc(-c4ccncc4)o3)CC2)c1]

Compound 32
Mp: 188-190° C.
$^1$H NMR (400 MHz, CDCl3) δ 2.76 (br s, 4H), 3.01 (t, J = 4.8 Hz, 4H), 3.59 (s, 2H), 3.80 (s, 3H), 6.81 (ddd, J = 8.3, 2.8, 0.8 Hz, 1H), 6.89-6.92 (m, 2H), 7.06 (d, J = 3.7 Hz, 1H), 7.22 (d, J = 8.0 Hz, 1H), 7.32 (d, J = 8.0 Hz, 1H), 7.37-7.40 (m, 2H), 7.73 (dd, J = 4.4, 1.6 Hz, 2H), 8.78 (dd, J = 4.4, 1.6 Hz, 2H), 8.86 (d, J = 1.8 Hz, 1H), 9.66 (br s, 1H) )
HRMS (ESI-MS): m/z calcd for C$_{29}$H$_{27}$F$_3$N$_4$O$_3$ (M$^+$ + H) 537.21080, found 537.20560

TABLE 4-continued

Analytical data for synthesized compounds

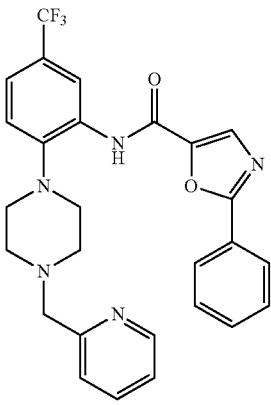 [SMILES: O=C(Nc1cc(C(F)(F)F)ccc1N1CCN(Cc2ccccn2)CC1)c1cnc(-c2ccccc2)o1]

Compound 33
$^1$H NMR (300 MHz; CDCl$_3$) δ 2.84 (br s, 4H), 3.04 (t, J = 4.3, 4H), 3.79 (s, 2H), 7.19 (dd, J = 6.7, 5.0 Hz, 1H), 7.31 (d, J = 8.3 Hz, 1H), 7.38 (dd, J = 8.5, 1.5 Hz, 1H), 7.42 (d, J = 7.8 Hz, 1H), 7.60-7.63 (m, 3H), 7.67 (td, J = 7.6, 1.8 Hz, 1H), 7.92 (s, 1H), 8.20-8.24 (m, 2H), 8.58-8.60 (m, 1H), 8.83 (d, J = 1.3 Hz, 1H), 9.57 (br s, 1H)
HRMS (ESI-MS): m/z calcd for C$_{27}$H$_{24}$F$_3$N$_5$O$_2$Na (M$^+$ + Na) 530.1780, found 530.1705

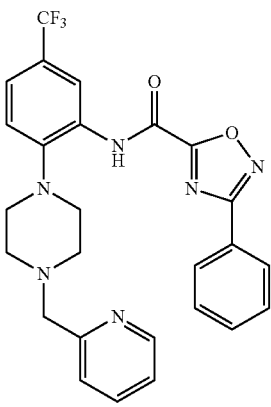 [SMILES: O=C(Nc1cc(C(F)(F)F)ccc1N1CCN(Cc2ccccn2)CC1)c1nc(-c2ccccc2)no1]

Compound 34
$^1$H NMR (300 MHz; CDCl$_3$) δ 2.87 (br s, 4H), 3.06 (t, J = 4.7, 4H), 3.82 (s, 2H), 7.19 (ddd, J = 7.5, 5.0, 1.0 Hz, 1H), 7.32 (d, J = 8.4 Hz, 1H), 7.42-7.46 (m, 2H), 7.57-7.62 (m, 3H), 7.68 (td, J = 7.7, 1.8 Hz, 1H), 8.18-8.21 (m, 2H), 8.58-8.60 (m, 1H), 8.75 (d, J = 1.8 Hz, 1H), 10.34 (br s, 1H)
HRMS (ESI-MS): m/z calcd for C$_{26}$H$_{23}$F$_3$N$_6$O$_2$Na (M$^+$ + Na) 531.1732, found 531.1677

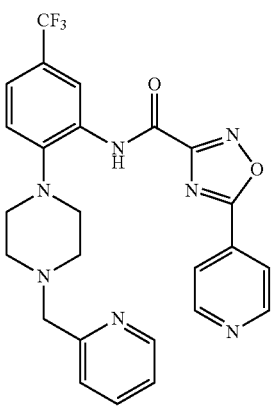 [SMILES: O=C(Nc1cc(C(F)(F)F)ccc1N1CCN(Cc2ccccn2)CC1)c1noc(-c2ccncc2)n1]

Compound 35
$^1$H NMR (300 MHz; CDCl$_3$) δ 2.85 (br s, 4H), 3.03 (t, J = 4.7, 4H), 3.80 (s, 2H), 7.18 (ddd, J = 7.6, 4.9, 1.2 Hz, 1H), 7.28 (d, J = 8.3 Hz, 1H), 7.39 (d, J = 8.4, 2.0 Hz, 1H), 7.45 (d, J = 7.8 Hz, 1H), 7.59-7.71 (m, 4H), 8.23-8.27 (m, 2H), 8.56-8.59 (m, 1H), 8.82 (d, J = 1.8 Hz, 1H), 10.17 (br s, 1H)
HRMS (ESI-MS): m/z calcd for C$_{25}$H$_{23}$F$_3$N$_6$O$_2$Na (M$^+$ + Na) 531.1732, found 531.1652

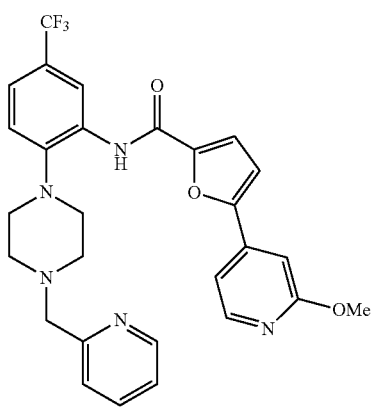 [SMILES: COc1cc(-c2ccc(C(=O)Nc3cc(C(F)(F)F)ccc3N3CCN(Cc4ccccn4)CC3)o2)ccn1]

Compound 36
$^1$H NMR (400 MHz, DMSO) δ 2.73 (br s, 4H) 2.99 (br s, 4H), 3.74 (s, 2H), 3.96 (s, 3H), 7.27 (m, 1H), 7.38 (s, 1H), 7.46-7.52 (m, 6H), 7.78 (m, 1H), 8.34 (d, J = 5.2 Hz, 1H), 8.51 (d, J = 3.6 Hz, 1H), 8.60 (s, 1H), 9.74 (s, 1H). MS (ESI-MS): m/z calcd for C$_{28}$H$_{26}$F$_3$N$_5$O$_3$ [M+]$^+$ 538.20, found 538.32.

TABLE 4-continued

Analytical data for synthesized compounds

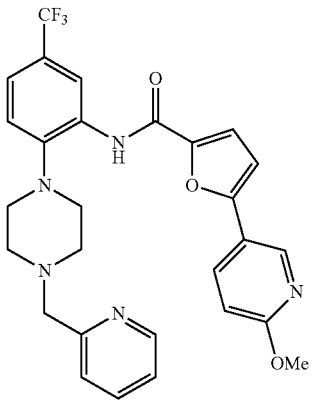 [SMILES: COc1ccc(-c2ccc(C(=O)Nc3cc(C(F)(F)F)ccc3N3CCN(Cc4ccccn4)CC3)o2)cn1]

Compound 37
$^1$H NMR (400 MHz, DMSO) δ 2.74 (br s, 4H), 2.99 (br s, 4H), 3.75 (s, 2H), 3.98 (s, 3H), 7.05 (d, J = 8.8 Hz, 1H), 7.21 (d, J = 3.6 Hz, 1H), 7.27 (m, 1H), 7.43-7.54 (m, 4H), 7.78 (m, 1H), 8.26 (dd, J = 8.8, 2.4 Hz, 1H), 8.49 (d, J = 4.4 Hz, 1H), 8.61 (s, 1H), 8.87 (d, J = 2.4 Hz, 1H), 9.72 (s, 1H), MS (ESI-MS): m/z calcd for $C_{28}H_{26}F_3N_5O_3$ [MH]$^+$ 538.20, found 538.30.

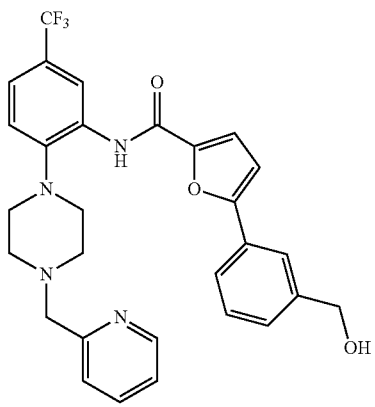 [SMILES: O=C(Nc1cc(C(F)(F)F)ccc1N1CCN(Cc2ccccn2)CC1)c1ccc(-c2cccc(CO)c2)o1]

Compound 38
$^1$H NMR (400 MHz, DMSO) δ 9.62 (s, 1H), 8.61 (s, 1H), 8.50 (d, J = 3.6 Hz, 1H), 7.88 (d, J = 8.4 Hz, 2H), 7.78 (m, 1H), 7.44-7.58 (m, 6H), 7.25-7.30 (m, 2H), 5.42 (t, J = 5.2 Hz, 1H), 4.65 (d, J = 4.4 Hz, 2H), 3.70 (s, 2H), 3.01 (br s, 4H), 2.75 (br s, 4H). MS (ESI-MS): m/z calcd for $C_{29}H_{27}F_3N_4O_3$ [MH]$^+$ 537.20, found 537.42.

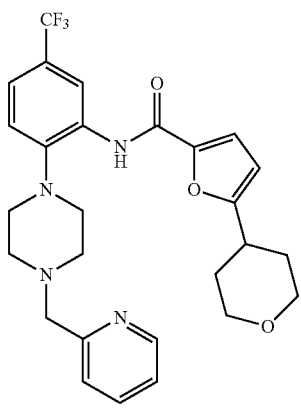 [SMILES: O=C(Nc1cc(C(F)(F)F)ccc1N1CCN(Cc2ccccn2)CC1)c1ccc(C2CCOCC2)o1]

Compound 39
$^1$H NMR (400 MHz, DMSO) δ 9.50 (s, 1H), 8.63 (s, 1H), 8.52 (d, J = 4.0 Hz, 1H), 7.80 (m, 1H), 7.49 (m, 3H), 7.29 (m, 1H), 7.25 (d, J = 3.6 Hz, 1H), 6.47 (d, J = 3.2 Hz, 1H), 4.00 (d, J = 9.6 Hz, 2H), 3.69 (s, 2H), 3.53 (t, J = 10.8 Hz, 2H), 3.10 (m, 1H), 2.96 (br s, 4H), 2.71 (br s, 4H), 2.00 (d, J = 11.2 Hz, 2H), 1.67-1.83 (m, 2H). MS (ESI-MS): m/z calcd for $C_{27}H_{29}F_3N_4O_3$ [MH]$^+$ 515.22, found 515.42

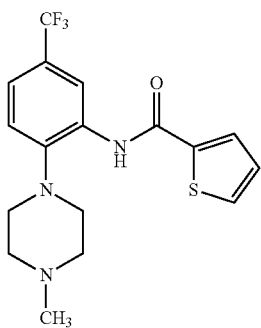 [SMILES: CN1CCN(c2ccc(C(F)(F)F)cc2NC(=O)c2cccs2)CC1]

Compound 40
$^1$H NMR (300 MHz; CDCl$_3$) δ 2.41 (s, 3H), 2.66 (br s, 4H), 2.97 (t, J = 4.7 Hz, 4H), 7.17 (dd, J = 5.0, 3.8 Hz, 1H), 7.27 (d, J = 8.3 Hz, 1H), 7.33 (dd, J = 8.3, 1.8 Hz, 1H), 7.57 (dd, J = 5.0, 1.1 Hz, 1H), 7.67 (dd, J = 3.8, 1.1 Hz, 1H), 8.81 (d, J = 1.8 Hz, 1H), 9.18 (s, 1H)
HRMS (ESI-MS): m/z calcd for $C_{17}H_{19}F_3N_3OS$ (M$^+$ + H) 370.1201, found 370.1192

TABLE 4-continued

Analytical data for synthesized compounds

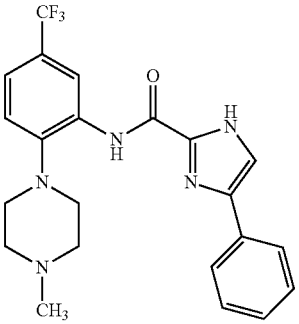 [SMILES: CN1CCN(c2ccc(C(F)(F)F)cc2NC(=O)c2nc(-c3ccccc3)c[nH]2)CC1]

Compound 41
$^1$H NMR (300 MHz; d6-DMSO) δ 2.34 (s, 3H), 2.69 (br s, 4H), 2.95 (m, 4H), 7.26-7.31 (m, 1H), 7.38-7.44 (m, 4H), 7.96-8.00 (m, 3H), 8.72 (br s, 1H), 10.33 (br s, 1H)
HRMS (ESI-MS): m/z calcd for $C_{22}H_{23}F_3N_5O$ ($M^+$ + H) 430.1855, found 430.1832

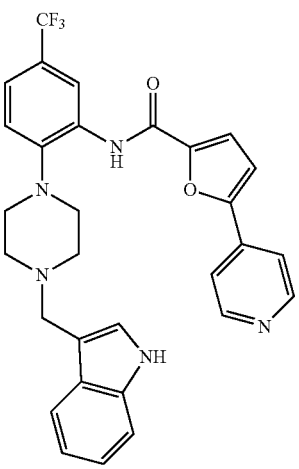 [SMILES: O=C(Nc1cc(C(F)(F)F)ccc1N1CCN(Cc2c[nH]c3ccccc23)CC1)c1ccc(-c2ccncc2)o1]

Compound 42
$^1$H NMR (300 MHz; CDCl$_3$) δ 2.82 (br s, 4H), 2.97 (m, 4H), 3.82 (s, 2H), 7.06 (d, J = 3.7 Hz, 1H), 7.08-7.13 (m, 2H), 7.17-7.23 (m, 1H), 7.30 (d, J = 8.2 Hz, 1H), 7.35-7.40 (m, 3H), 7.72 (d, J = 8.0 Hz, 1H), 7.75-7.77 (m, 2H), 8.30 (s, 1H), 8.78-8.80 (m, 2H), 8.86 (d, J = 1.8 Hz, 1H), 9.68 (s, 1H). HRMS (ESI-MS): m/z calcd for $C_{30}H_{27}F_3N_5O_2$ ($M^+$ + H) 546.2117, found 546.2101

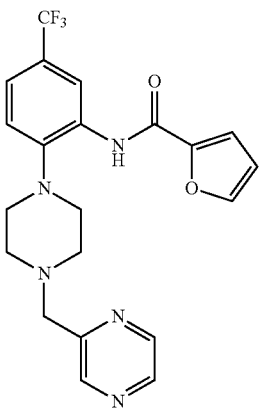 [SMILES: O=C(Nc1cc(C(F)(F)F)ccc1N1CCN(Cc2cnccn2)CC1)c1ccco1]

Compound 43
$^1$H NMR (400 MHz, DMSO) δ 2.71 (br s, 4H), 2.97 (br s, 4H), 3.81 (s, 2H), 6.78-6.77 (dd, J = 3.6, 1.6, Hz, 1H), 7.35 (d, J = 3.2 Hz, 1H), 7.50-7.45 (m, 2H), 8.01 (d, J = 1.2 Hz, 1H), 8.51 (s, 1H), 8.58 (s, 1H), 8.63 (s, 1H), 8.75 (s, 1H), 9.44 (s, 1H),.
MS (ESI-MS): m/z calcd for $C_{21}H_{20}F_3N_5O_2$ $[MH]^+$ 431.16, found 432.37.

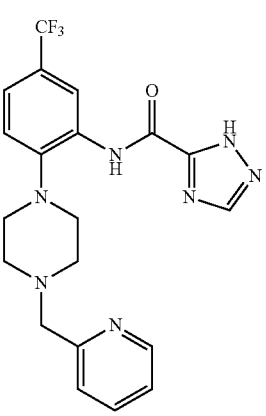 [SMILES: O=C(Nc1cc(C(F)(F)F)ccc1N1CCN(Cc2ccccn2)CC1)c1ncn[nH]1]

Compound 44
$^1$H NMR (400 MHz, DMSO) δ 2.68 (br s, 4H). 2.97 (br s, 4H), 3.71 (s, 2H), 7.30-7.27 (m, 1H), 7.49-7.51 (m, 3H), 7.80 (td, J = 7.6, 2.0 Hz, 1H), 8.52 (d, J = 4.4 Hz, 1H), 8.70 (s, 1H), 8.74 (s, 1H), 10.07 (s, 1H), 14.90 (s, 1H), MS (ESI-MS): m/z calcd for $C_{20}H_{20}F_3N_5O$ $[MH]^+$ 432.17, found 432.37.

TABLE 4-continued

Analytical data for synthesized compounds

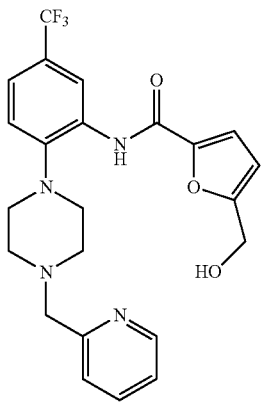 [SMILES: O=C(Nc1cc(C(F)(F)F)ccc1N1CCN(Cc2ccccn2)CC1)c1ccc(CO)o1]

Compound 45
$^1$H NMR (400 MHz, DMSO) δ 2.69 (br s, 4H), 2.93 (br s, 4H), 3.17 (m, 1H), 4.54 (d, J = 4.8 Hz, 2H), 5.62-5.70 (m, 1H), 6.57 (d, J = 3.2 Hz, 1H), 7.24-7.31 (m, 2H), 7.45-7.50 (m, 3H), 7.78-7.79 (m, 1H), 8.50 (s, 2H), 9.47 (s, 1H). MS (ESI-MS): Calcd for $C_{23}H_{23}F_3N_4O_3$ (MH+) 461.17, found 461.36.

REFERENCES

Bressler, S., Bressler, N. M., Clemons, T., Ferris, F. L., Milton, R. C., Klien, R., Klien, B. and Age-Related Eye Dis Study, G. (2004) 'Ocular risk factors for developing neovascular AMD in the fellow eyes of patients with unilateral neovascular AMD', Investigative Ophthalmology & Visual Science, 45, U924-U924.

Ferris, F. L. Fine, S. L. and Hyman, L. (1984) 'Age-related macular degeneration and blindness due to neovascular maculopathy', Archives of Ophthalmology, 102(11), 1640-1642.

Patz, A., Fine, S. L., Finkelstein, D. and Yassur, Y. (1977) 'Diseases of macula—diagnosis and management of choroidal neovascularization', Transactions American Academy of Ophthalmology and Otolaryngology, 83(3), 468-475.

Fine, S. L., Berger, J. W., Maguire, M. G. and Ho, A. C. (2000) 'Drug therapy: Age-related macular degeneration', New England Journal of Medicine, 342(7), 483-492.

Campochiaro, P. A., Nguyen, Q. D., Shah, S. M., Klein, M. L., Holz, E., Frank, R. N., Saperstein, D. A., Gupta, A., Stout, J. T., Macko, J., DiBartolomeo, R. and Wei, L. L. (2006) 'Adenoviral vector-delivered pigment epithelium-derived factor for neovascular age-related macular degeneration: Results of a phase I clinical trial', Human Gene Therapy, 17(2), 167-176.

Dvorak, H. F., Brown, L. F., Detmar, M. and Dvorak, A. M. (1995) 'Vascular-permeability factor vascular endothelial growth-factor, microvascular hyperpermeability, and angiogenesis', American Journal of Pathology, 146(5), 1029-1039.

D'Amore, P. A., Shima, D. T., Adamis, A, P., Yeo, K. T., Yeo. T. K., Allende, R. and Folkman, J. (1994) 'differential regulation of VEGF/VPF and basic FGF by hypoxia', Faseb Journal, 8(4), A116-A116.

Spilsbury, K., Garrett, K. L., Shen, W. Y., Constable, I. J. and Rakoczy, P. E. (2000) 'Overexpression of vascular endothelial growth factor (VEGF) in the retinal pigment epithelium leads to the development of choroidal neovascularization', American Journal of Pathology, 157(1), 135-144.

Anderson, D. H., Mullins, R. F., Hageman, G. S. and Johnson, L. V. (2002) 'Perspective—A role for local inflammation in the formation of drusen in the aging eye', American Journal of Ophthalmology, 134(3), 411-431.

Das, A., Fanslow, W., Cerretti, D., Warren, E., Talarico, N. and McGuire, P. (2003) 'Angiopoietin/Tek interactions regulate MMP-9 expression and retinal neovascularization', Laboratory Investigation, 83(11), 1637-1645.

Leung, D. W., Cachianes, G., Kuang, W. J., Goeddel, D. V. and Ferrara, N. (1989) 'Vascular endothelial growth-factor is a secreted angiogenic mitogen', Science, 246 (4935), 1306-1309.

Jingling, L., Xue, Y., Agarwal, N. and Roque, R. S. (1999) 'Human Muller cells express VEGF183, a novel spliced variant of vascular endothelial growth factor', Iovs, 40(3), 752-759.

Houck, K. A., Ferrara, N., Winer, J., Cachianes, G., Li, B. and Leung, D. W. (1991) 'The vascular endothelial growth-factor family—identification of a 4th molecular-species and characterization of alternative splicing of rna', Molecular Endocrinology, 5(12), 1806-1814.

Mineur, P., Colige, A. C., Deroanne, C. F., Dubail, J., Kesteloot, F., Habraken, Y., Noel, A., Voo, S., Waltenberger, J., Lapiere, C. M., Nusgens, B. V. and Lambert, C. A. (2007) 'Newly identified biologically active and proteolysis-resistant VEGF-A isoform VEGF111 is induced by genotoxic agents', Journal of Cell Biology, 179(6), 1261-1273.

Tischer, E., Gospodarowicz, D., Mitchell, R., Silva, M., Schilling, J., Lau, K., Crisp, T., Fiddes, J. C. and Abraham, J. A. (1989) 'Vascular endothelial growth-factor—a new member of the platelet-derived growth-factor gene family', Biochemical and Biophysical Research Communications, 165(3), 1198-1206.

Neufeld, G., Cohen, T., Gengrinovitch, S. and Poltorak, Z. (1999) 'Vascular endothelial growth factor (VEGF) and its receptors', Faseb Journal, 13(1), 9-22.

Bates, D. O., Cui, T. G., Doughty, J. M., Winkler, M., Sugiono, M., Shields, J. D., Peat, D., Gillatt, D. and Harper, S. J. (2002) 'VEGF(165)b, an inhibitory splice variant of vascular endothelial growth factor, is down-regulated in renal cell carcinoma', Cancer Research, 62(14), 4123-4131.

Woolard, J., Wang, W. Y., Bevan, H. S., Qiu, Y., Morbidelli, L., Pritchard-Jones, R. O., Cui, T. G., Sugiono, M., Waine, E., Perrin, R., Foster, R., Digby-Bell, J., Shields, J. D., Whittles, C. E., Mushens, R. E., Gillatt, D. A., Ziche, M., Harper, S. J. and Bates, D. O. (2004) 'VEGF(165)b, an inhibitory vascular endothelial growth factor splice variant: Mechanism of action, in vivo effect on angiogenesis and endogenous protein expression', *Cancer Research*, 64(21), 7822-7835.

Perth, R. M., Konopatskaya, O., Qin, Y., Harper, S., Bates, D. O. and Churchill, A. J. (2005) 'Diabetic retinopathy is associated with a switch in splicing from anti- to pro-angiogenic isoforms of vascular endothelial growth factor', *Diabetologia*, 48(11), 2422-2427.

Varey, A. H. R., Rennel, E. S., Qiu, Y., Bevan, H. S., Perrin, R. M., Raffy, S., Dixon, A. R., Paraskeva, C., Zaccheo, O., Hassan, A. B., Harper, S. J. and Bates, D. O. (2008) 'VEGF(165)b, an antiangiogenic VEGF-A isoform, binds and inhibits bevacizumab treatment in experimental colorectal carcinoma: balance of pro- and antiangiogenic VEGF-A isoforms has implications for therapy', *British Journal of Cancer*, 98(8), 1366-1379.

Pritchard-Jones, R. O., Dunn, D. B. A., Qiu, Y., Varey, A. H. R., Orlando, A., Rigby, H., Harper, S. J. and Bates, D. O. (2007) 'Expression of VEGF(xxx)b, the inhibitory isoforms of VEGF, in malignant melanoma', *British Journal of Cancer*, 97(2), 223-230.

Hua, J., Spee, C., Kane, S., Rennel, E. S., Magnussen, A. L., Qiu, Y., Varey, A., Dhayade, S., Churchill, A. J., Harper, S. J., Bates, D. O. and Hinton, D. R. (2010) 'Recombinant Human VEGF(165)b Inhibits Experimental Choroidal Neovascularization', *Investigative Ophthalmology & Visual Science*, 51(8), 4282-4288.

Magnussen, A. L., Rennel, E. S., Hua, J., Bevan, H. S., Long, N. B., Lehrling, C., Gammons, M., Floege, J., Harper, S. J., Agostini, H. T., Bates, D. O. and Churchill, A. J. (2010) 'VEGF-A(165)b Is Cytoprotective and Antiangiogenic in the Retina', *Investigative Ophthalmology & Visual Science*, 51(8), 4273-4281.

Gragoudas, E. S. (2004) 'VEGF inhibition study in ocular neovascularization-1 (VISION-1): Efficacy results from phase II/III Macugen (TM) (Pegaptanib sodium) clinical trials', *Iovs*, 45(Suppl. 1), U924.

Rosenfeld, P. J., Rich, R. M. and Lalwani, G. A. (2006) 'Ranibizumab: Phase III clinical trial results', *Ophthalmology clinics of North America*, 19(3), 361-72.

Brown, D. M., Kaiser, P. K., Michels, M., Soubrane, G., Heier, J. S., Kim, R. Y., Sy, J. P., Schneider, S. and Grp, A. S. (2006) 'Ranibizumab versus verteporfin for neovascular age-related macular degeneration', *New England Journal of Medicine*, 355(14), 1432-1444.

Brown, D. M., Michels, M., Kaiser, P. K., Heier, J. S., Sy, J. P. and Ianchulev, T. (2009) 'Ranibizumab versus Verteporfin Photodynamic Therapy for Neovascular Age-Related Macular Degeneration: Two-Year Results of the ANCHOR Study', *Ophthalmology*, 116(1), 57-65.

Schmidt-Erfurth, U., Eldem, B., Guymer, R., Korobelnik, J. F., Schlingemann, R. O., Axer-Siegel, R., Wiedemann, P., Simader, C., Gekkieva, M., Weichselberger, A. and Grp, E. S. (2011) 'Efficacy and Safety of Monthly versus Quarterly Ranibizumab Treatment in Neovascular Age-related Macular Degeneration: The EXCITE Study', *Ophthalmology*, 118(5).

Good, T. J. and Kahook, M. Y. (2010) 'The role of endothelia in the pathophysiology of glaucoma', *Expert Opinion on Therapeutic Targets*, 14(6), 647-654.

Jager, R. D., Aiello, L. P., Patel, S. C. and Cunningham, E. T. (2004) 'Risks of intravitreous injection: A comprehensive review', *Retina—the Journal of Retinal and Vitreous Diseases*, 24(5), 676-698.

Nowak, D. G., Amin, E. M., Rennel, E. S., Hoareau-Aveilla, C., Gammons, M., Damodoran, G., Hagiwara, M., Harper, S. J., Woolard, J., Ladomery, M. R. and Bates, D. O. (2010) 'Regulation of Vascular Endothelial Growth Factor (VEGF) Splicing from Pro-angiogenic to Anti-angiogenic Isoforms a novel therapeutic strategy for angiogenesis', *Journal of Biological Chemistry*, 285(8), 5532-5540.

Amin, E. M., Oltean, S., Hua, J., Gammons, M. V. R., Hamdollah-Zadeh, M., Welsh, G. I., Cheung, M. K., Ni, L., Kase, S., Renne, E. S., Symonds, K. E., Nowak, D. G., Royer-Pokora, B., Salaam, M. A., Hagiwara, M., Schumacher, V. A., Harper, S. J., Hinton, D. R., Bates, D. O. and Ladomery, M. R. (2011) 'WT1 Mutants Reveal SRPK1 to Be a Downstream Angiogenesis Target by Altering VEGF Splicing', *Cancer Cell*, 20(6), 768-780.

Sanford, J. R., Ellis, J. D., Cazalla, D. and Caceres, J. F. (2005a) 'Reversible phosphorylation differentially affects nuclear and cytoplasmic functions of splicing factor 2/alternative splicing factor', *Proceedings of the National Academy of Sciences of the United States of America*, 102(42), 15042-15047.

Nowak, D. G., Woolard, J., Amin, E. M., Konopatskaya, O., Saleem, M. A., Churchill, A. J., Ladomery, M. R., Harper, S. J. and Bates, D. O. (2008) 'Expression of pro- and anti-angiogenic isoforms of VEGF is differentially regulated by splicing and growth factors', *Journal of Cell Science*, 121(20), 3487-3495.

Doukas, J., Mahesh, S., Umeda, N., Kachi, S., Akiyama, H., Yokoi, K., Cao, J., Chen, Z., Dellamary, L., Tam, B., Racanelli-Layton, A., Hood, J., Martin, M., Noronha, G., Soll, R. and Campochiaro, P. A. (2008) 'Topical administration of a multi-targeted kinase inhibitor suppresses choroidal neovascularization and retinal edema', *Journal of Cellular Physiology*, 216(1), 29-37.

Fukuhara, T., Hosoya, T., Shimizu, S., Sumi, K., Oshiro, T., Yoshinaka, Y., Suzuki, M., Yamamoto, N., Herzenberg, L. A. and Hagiwara, M. (2006) 'Utilization of host SR protein kinases and RNA-splicing machinery during viral replication', *Proceedings of the National Academy of Sciences of the United States of America*, 103(30), 11329-11333.

Rennel, E. S., Regula, J. T., Harper, S. J., Thomas, M., Klein, C. and Bates, D. O. (2011) 'A Human Neutralizing Antibody Specific to Ang-2 Inhibits Ocular Angiogenesis', *Microcirculation*, 18(7).

Aubol, B. E., Chakrabarti, S., Ngo, J., Shaffer, J., Nolen, B., Fu, X. D., Ghosh, G. and Adams, J. A. (2003) 'Processive phosphorylation of alternative splicing factor/splicing factor 2', *Proceedings of the National Academy of Sciences of the United States of America*, 100(22), 12601-12606.

Velazquez-Dones, A., Hagopian, J. C., Ma, C. T., Zhong, X. Y., Zhou, H. L., Ghosh, G., Fu, X. D. and Adams, J. A. (2005) 'Mass spectrometric and kinetic analysis of ASF/SF2 phosphorylation by SRPK1 and Clk/Sty', *Journal of Biological Chemistry*, 280(50), 41761-41768.

Ngo, J. C. K., Chakrabarti, S., Ding, J. H., Velazquez-Dones, A., Nolen, B., Aubol, B. E., Adams, J. A., Fu, X. D. and Ghosh, G. (2005) 'Interplay between SRPK and Clk/Sty kinases in phosphorylation of the splicing factor ASF/SF2 is regulated by a docking motif in ASF/SP2', *Molecular Cell*, 20(1), 77-89.

Xu, J., Dou, T., Liu, C., Fu, M., Huang, Y., Gu, S., Zhou, Y. and Xie, Y. (2011) 'The evolution of alternative splicing axons in vascular endothelial growth factor A', *Gene*, 487 (2).

Caires, K. C., de Avila, J. M., Cupp, A. S. and McLean, D. J. (2012) 'VEGFA Family Isoforms Regulate Spermatogonial Stem Cell Homeostasis in Vivo', *Endocrinology*, 153(2).

Zhao, M., Shi, X., Liang, J., Miao, Y., Xie, W., Zhang, Y. and Li, X. (2011) 'Expression of pro- and anti-angiogenic isoforms of VEGF in the mouse model of oxygen-induced retinopathy', *Experimental Eye Research*, 93(6), 921-926.

Harris, S., Craze, M., Newton, J., Fisher, M., Shima, D. T., Tozer, G. M. and Kanthou, C. (2012) 'Do Anti-Angiogenic VEGF (VEGF$_{xxx}$b) Isoforms Exist? A Cautionary Tale', *Plos One*, 7(5).

McFee, R. M., Rozell, T. G. and Cupp, A. S. (2012) 'The balance of proangiogenic and antiangiogenic VEGFA isoforms regulate follicle development', *Cell and Tissue Research*, 349(3).

Ishida, S., Usui, T., Yamashiro, K., Kaji, Y., Amano, S., Ogura, Y., Hida, T., Oguchi, Y., Ambati, J., Miller, J. W., Gragoudas, E. S., Ng, Y. S., D'Amore, P. A., Shima, D. T. and Adamis, A. P. (2003) 'VEGF$_{164}$-mediated inflammation is required for pathological, but not physiological, ischemia-induced retinal neovascularization', *Journal of Experimental Medicine*, 198(3), 483-489.

Geroski, D. H. and Edelhauser, H. F. (2000) 'Drug delivery for posterior segment eye disease', *Investigative Ophthalmology & Visual Science*, 41(5), 961-964.

Keyt, B. A., Nguyen, H. V., Berleau, L. T., Duarte, C. M., Park, J., Chen, H. and Ferrara, N. (1996) 'Identification of vascular endothelial growth factor determinants for binding KDR and FLT-1 receptors —Generation of receptor-selective VEGF variants by site-directed mutagenesis', *Journal of Biological Chemistry*, 271(10), 5638-5646.

Stalmans, I., Ng, Y. S., Rohan, R., Fruttiger, M., Bouche, A., Yuce, A., Fujisawa, H., Hermans, B., Shari, M., Jansen, S., Hicklin, D., Anderson, D. J., Gardiner, T., Hammes, H. P., Moons, L., Dewerchin, M., Collen, D., Carmeliet, P. and D'Amore, P. A. (2002) 'Arteriolar and venular patterning in retinas of mice selectively expressing VEGF isoforms', *Journal of Clinical Investigation*, 109(3).

Gammons, M. V., Dick, A. D., Harper, S. J., Bates, D. O. (2013) SRPK1 Inhibition Modulates VEGF Splicing to Reduce Pathological Neovascularization in a Rat Model of Retinopathy of Prematurity *Invest. Ophthalmol. Vis. Sci.* vol. 54(8) 5797-5806.

Gammons, M. V., Fedorov, O., Ivison, D., Du, C., Clark, T., Hopkins, C., Hagiwara, M., Dick, A. D., Cox, R., Harper, S. J., Hancox, J. C. and Bates, D. O. (2013) Topical Antiangiogenic SRPK1 Inhibitors Reduce Choroidal Neovascularization in Rodent Models of Exudative AMD *Invest. Ophthalmol. Vis. Sci.* 54(9) 6052-6062.

Federov O, Niesen F H, Knapp S. Kinase Inhibitor Selectivity Profiling Using Differential Scanning Fluorimetry. In: Kuster B, ed. Kinase Inhibitors: Methods and Protocols: Springer, 2011:109-18.

Carter J G, Gammons M V, Damodaran G, Churchill A J, Harper S J, Bates D O. (2015) The carboxyl terminus of VEGF-A is a potential target for anti-angiogenic therapy. Angiogenesis 18(1), 23-30.

The invention claimed is:

1. A method of treating pain, comprising administering to a subject in need thereof a compound of Formula (I)

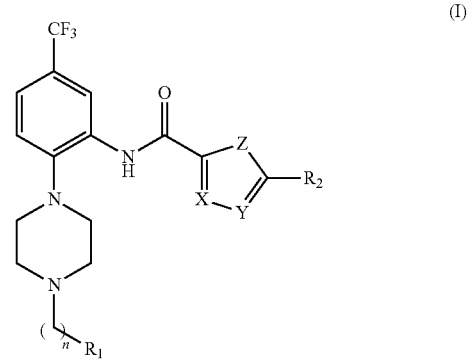

or a pharmaceutically acceptable salt thereof;
wherein:
n=1, 2, 3 or 0;
$R_1$=a 4- to 8-membered carbocyclic group, which may have one or more substituent;
a 4- to 8-membered heterocyclic group comprising one oxygen atom, which may have one or more substituent; a 4- to 8-membered heterocyclic group comprising one nitrogen atom, which may have one or more substituent, a 4- to 8-membered heterocyclic group comprising one nitrogen atom and one oxygen atom which may have one or more substituent; a 4- to 8-membered heterocyclic group comprising two nitrogen atoms which may have one or more substituent; a 4- to 8-membered heterocyclic group comprising three nitrogen atoms which may have one or more substituent, or a condensed aromatic heterocyclic group, which may have one or more substituent;

X=CH, NH or N;
Y=CH, NH or N;
Z=O, S, N or NH; and
$R_2$=H, a $C_{1-6}$ alkyl group; a phenyl group; a 4- to 8-membered heterocyclic group; or a condensed aromatic heterocyclic group, each of which may have one or more substituent.

2. A method according to claim 1, wherein
n=1, 2, 3 or 0;
$R_1$=a 4- to 8-membered carbocyclic group, which may have one or more substituent;
 a 4- to 8-membered heterocyclic group having one nitrogen atom, which may have one or more substituent, a 4- to 8-membered heterocyclic group comprising one nitrogen atom and one oxygen atom which may have one or more substituent, or a 4- to 8-membered heterocyclic group comprising two nitrogen atoms which may have one or more substituent;
X=CH or N;
Y=CH or N;
Z=O, S or NH; and
$R_2$=a phenyl group; a 4- to 8-membered heterocyclic group or a condensed aromatic heterocyclic group.

3. A method according to claim 1, wherein $R_1$ represents a 4- to 8- membered heterocyclic group comprising one nitrogen atom, which may have one or more substituent.

4. A method according to claim 1, wherein $R_1$ represents a 6-membered heteroaromatic group comprising one nitrogen atom, which may have one or more substituent.

5. A method according to claim 1, wherein $R_1$ represents a 2-, 3- or 4-pyridyl group, each of which may have one or more substituent.

6. A method according to claim 1, wherein $R_1$ represents a pyrimidinyl group, which may have one or more substituent.

7. A method according to claim 1, wherein $R_1$ represents a 4- to 8-membered carbocyclic group, which may have one or more substituent.

8. A method according to claim 1, wherein $R_1$ represents a phenyl group, which may have one or more substituent.

9. A method according to claim 1, wherein $R_2$ represents a nitrogen- or oxygen-containing 4- to 8-membered heteroaromatic ring, which may have one or more substituent.

10. A method according to claim 1, wherein $R_2$ represents a nitrogen-containing 4- to 8-membered heteroaromatic ring, which may have one or more substituent.

11. A method according to claim 1, wherein $R_2$ represents a 2- or 3- or 4-pyridyl group, each of which may have one or more substituent.

12. A method according to claim 1, wherein $R_2$ represents an oxygen-containing 4- to 8- membered heterocyclic ring, which may have one or more substituent.

13. A method according to claim 1, wherein $R_2$ represents a 4- to 8-membered carbocyclic group, which may have one or more substituent.

14. A method according to claim 1, wherein $R_2$ represents a phenyl group, which may have one or more substituent.

15. A method according to claim 1, wherein $R_2$ represents H, or $C_{1-6}$ alkyl which may have one or more substituent.

16. A method according to claim 1, wherein $R_2$ represents a methyl group, which may have one or more substituent.

17. A method according to claim 1, wherein $R_2$ represents a tetrahydropyranyl group, which may have one or more substituent.

18. A method according to claim 1, wherein:
X=Y=CH and Z=O;
X=Y=CH and Z=S;
X=Y=N and Z=O; or
X=N, Y=CH, and Z=O.

19. A method according to claim 1, wherein n=1 or 2.

20. A method according to claim 1, wherein the pain comprises non-inflammatory neuropathic or nociceptive pain.

\* \* \* \* \*

```
SEQUENCE LISTING

<160> NUMBER OF SEQ ID NOS: 1

<210> SEQ ID NO 1
<211> LENGTH: 29
<212> TYPE: PRT
<213> ORGANISM: Artificial Sequence
<220> FEATURE:
<223> OTHER INFORMATION: SRSF1 RS PEPTIDE

<400> SEQUENCE: 1

Arg Ser Pro Ser Tyr Gly Arg Ser Arg Ser Arg Ser Arg Ser
1               5                   10                  15

Arg Ser Arg Ser Arg Ser Asn Ser Arg Ser Arg Ser Tyr
                20                  25
```